United States Patent
Lawson et al.

(10) Patent No.: US 9,801,872 B2
(45) Date of Patent: Oct. 31, 2017

(54) PYRIDINYL AND FUSED PYRIDINYL TRIAZOLONE DERIVATIVES

(71) Applicant: Takeda Pharmaceutical Company Limited, San Diego, CA (US)

(72) Inventors: John David Lawson, Carlsbad, CA (US); Mark Sabat, San Diego, CA (US); Nicholas Scorah, San Diego, CA (US); Christopher Smith, San Diego, CA (US); Phong H. Vu, San Diego, CA (US); Haixia Wang, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/197,051

(22) Filed: Jun. 29, 2016

(65) Prior Publication Data
US 2016/0310483 A1 Oct. 27, 2016

Related U.S. Application Data

(62) Division of application No. 14/203,366, filed on Mar. 10, 2014, now Pat. No. 9,402,841.

(60) Provisional application No. 61/776,445, filed on Mar. 11, 2013.

(51) Int. Cl.
| | |
|---|---|
| *A61K 31/44* | (2006.01) |
| *A61K 31/4725* | (2006.01) |
| *A61K 31/4375* | (2006.01) |
| *A61K 31/4439* | (2006.01) |
| *A61K 31/519* | (2006.01) |
| *C07D 401/14* | (2006.01) |
| *C07D 471/04* | (2006.01) |
| *C07D 401/04* | (2006.01) |
| *C07D 403/14* | (2006.01) |

(52) U.S. Cl.
CPC ...... *A61K 31/4725* (2013.01); *A61K 31/4375* (2013.01); *A61K 31/4439* (2013.01); *A61K 31/519* (2013.01); *C07D 401/04* (2013.01); *C07D 401/14* (2013.01); *C07D 403/14* (2013.01); *C07D 471/04* (2013.01)

(58) Field of Classification Search
None
See application file for complete search history.

(56) References Cited

U.S. PATENT DOCUMENTS

2014/0256734 A1 9/2014 Lawson et al.

FOREIGN PATENT DOCUMENTS

| WO | WO/99/54286 | 10/1999 |
|---|---|---|
| WO | WO/02/50071 A1 | 6/2002 |
| WO | WO/2007/087068 A2 | 8/2007 |
| WO | WO/2007/147771 A2 | 12/2007 |
| WO | WO/2008/033834 A1 | 3/2008 |
| WO | WO/2008/039218 A2 | 4/2008 |
| WO | WO/2008/121742 A2 | 10/2008 |
| WO | WO/2009/077334 A1 | 6/2009 |
| WO | WO/2009/098144 A1 | 8/2009 |
| WO | WO/2009/156284 A1 | 12/2009 |
| WO | WO/2010/000633 A1 | 1/2010 |
| WO | WO/2010/006947 A1 | 1/2010 |
| WO | WO/2010/056875 A1 | 5/2010 |
| WO | WO/2010/068788 A1 | 6/2010 |
| WO | WO/2010/068810 A2 | 6/2010 |
| WO | WO/2011/143495 A1 | 11/2011 |
| WO | WO/2011/153553 A2 | 12/2011 |
| WO | WO/2012/052167 A1 | 4/2012 |
| WO | WO/2012/064972 A2 | 5/2012 |

OTHER PUBLICATIONS

Browning, JL. et al. B Cells move to centre stage. Nature. 2006, vol. 5, p. 564.*
Seda, V. et al. B-cell receptor signaling and its crosstalk with other pathways in normal and malignant cells. Eur. J. Haematology. 2015, vol. 94, p. 200.*
Davis, R. Eric et al. "Chronic active B-cell-receptor signalling in diffuse large B-cell lymphoma" Nature, 2010, vol. 463, p. 88-92.
Edwards, Jonathan C.W. et al. "Efficacy of B-Cell—Targeted Therapy with Rituximab in Patients with Rheumatoid Arthritis" N Engl J Med 2004;350:2572-81.
Favas, C. et al. "B-cell-depletion therapy in SIE—what are the current prospects for its acceptance?" 2009, Nat. Rev. Rheumatol. 5:711-16.
Hauser, Stephen et al. "B-Cell Depletion with Rituximab in Relapsing—Remitting Multiple Sclerosis" N Engl J Med 2008;358:676-88.
Honigberg, Lee A. et al. "The Bruton tyrosine kinase inhibitor PCI-32765 blocks B-cell activation and is efficacious in models of autoimmune disease and B-cell malignancy" Proc. Natl. Acad. Sci. USA 107(29): 13075-80 (2010).

(Continued)

*Primary Examiner* — Noble Jarrell
*Assistant Examiner* — Ben S Michelson
(74) *Attorney, Agent, or Firm* — Matthew J. Russo

(57) ABSTRACT

Disclosed are compounds of Formula 1,

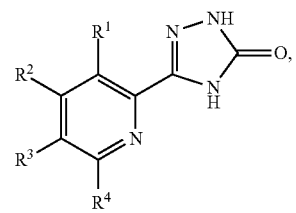

or pharmaceutically acceptable salts thereof, wherein $R^1$, $R^2$, $R^3$, and $R^4$ are defined in the specification. This disclosure also relates to materials and methods for preparing compounds of Formula 1, to pharmaceutical compositions which contain them, and to their use for treating Type I hypersensitivity reactions, autoimmune diseases, inflammatory disorders, cancer, non-malignant proliferative disorders, and other conditions associated with BTK.

33 Claims, No Drawings

(56) References Cited

OTHER PUBLICATIONS

Jansson, L. et al. "Genes on the X chromosome affect development of collagen-induced arthritis in mice" Clinical & Experimental Immunology; v:94 i:3 p. 459-65; Dec. 1993.

Khan, Wasif N. et al. "Defective B cell development and function in Btk-deficient mice" Immunity; v:3 i:3 p. 283-299; Sep. 1995.

Küppers, Ralf et al. "Mechanisms of B-cell lymphoma pathogenesis" 2005, Nat. Rev. Cancer v5, p. 251-62.

Lindvall, Jessica M. et al. "Bruton's tyrosine kinase: cell biology, sequence conservation, mutation spectrum, siRNA modifications, and expression profiling" Immunological Reviews, 2005, vol. 203: 200-215.

Rosen, Fred S. et al. "The primary immunodeficiencies" The New England Journal of Medicine, 1995, v333, n7, p. 431-440.

Satterthwaite, Anne B. et al. "The role of Bruton's tyrosine kinase in B-cell development and function: a genetic perspective" Immunological Reviews, 2000, vol. 175, pp. 120-127.

Shlomchik, Mark J. et al. "The Role of B Cells in Ipr/Ipr-induced Autoimmunity" J. Exp. Med., 1994, vol. 180, p. 1295-1306.

* cited by examiner

PYRIDINYL AND FUSED PYRIDINYL TRIAZOLONE DERIVATIVES

FIELD OF THE INVENTION

This invention relates to pyridinyl and fused pyridinyl triazolone derivatives, which are inhibitors of Bruton's tyrosine kinase (BTK), to pharmaceutical compositions which contain them, and to the use of the inhibitors to treat diseases, disorders, and conditions associated with BTK.

BACKGROUND OF THE INVENTION

BTK is a member of the TEC family of non-receptor protein tyrosine kinases, and it is involved in the regulation of B-cell development, activation, and survival through B-cell antigen receptor (BCR) signaling. See W. N. Khan et al., *Immunity* 3:283-299 (1995); and A. B. Satterthwaite and O. N. Witte, *Immunol. Rev.* 175:120-127 (2000). Mutation of the gene encoding BTK in humans leads to a condition known as X-linked agammaglobulinemia (XLA), which is characterized by reduced immune function, including impaired maturation of B cells, decreased levels of immunoglobulin and peripheral B cells, diminished T-cell independent immune response, and attenuated calcium mobilization following BCR stimulation. See F. S. Rosen et al., *N. Engl. J. Med.* 333(7):431-440 (1995); and J. M. Lindvall et al., *Immunol. Rev.* 203:200-215 (2005).

BTK's key role in B-cell development and the BCR signaling pathway suggests that inhibition of BTK may provide therapeutic benefit for the treatment of lymphoma, inflammatory disorders, and autoimmune diseases, among others. Clinical studies involving the depletion of mature B cells via treatment with rituximab indicate that rheumatoid arthritis, systemic lupus erythematosus (SLE), and multiple sclerosis may result from the over expression of B cells. See J. C. Edwards et al., *N. Engl. J. Med.* 350:2572-81 (2004); C. Favas and D. A. Isenberg *Nat. Rev. Rheumatol.* 5:711-16 (2009); and S. L. Hauser et al. *N. Engl. J. Med.* 358:676-88 (2008). Other studies suggest that the BCR pathway may be involved in the survival of tumor cells in non-Hodgkin lymphoma and diffuse large B-cell lymphoma. See R. Küppers, *Nat. Rev. Cancer* 5:251-62 (2005); and R. E. Davis et al., *Nature* 463:88-92 (2010). In preclinical studies, BTK-deficient mice have demonstrated decreased disease progression in murine models of SLE and resistance to collagen-induced arthritis. See M. J. Shlomchik et al., *J. Exp. Med.* 180:1295-1306 (1994); and L. Jansson and R. Holmdahl, *Clin. Exp. Immunol.* 94(3):459-65 (1993). Furthermore, a selective irreversible BTK inhibitor has been shown to completely suppress collagen-induced arthritis in mice, to inhibit autoantibody production and the development of kidney disease in a mouse model for SLE, and to induce objective clinical responses in dogs with spontaneous B-cell non-Hodgkin lymphoma. See L. A. Honigberg et al., *Proc. Natl. Acad. Sci. USA* 107(29):13075-80 (2010).

Certain inhibitors of Bruton's tyrosine kinase are described in WO 99/54286 A2, WO 2002/50071 A1, WO 2007/087068 A2, WO 2008/039218 A2, WO 2008/121742 A2, WO 2007/147771 A2, WO 2009/077334 A1, WO 2009/098144 A1, WO 2009/156284 A1, WO 2010/000633 A1, WO 2010/006947 A1, WO 2008/033834 A1, WO 2010/056875 A1, WO 2010/068788 A1, and WO 2010/068810 A2.

SUMMARY OF THE INVENTION

This invention provides pyridinyl and fused pyridinyl triazolone derivatives and pharmaceutically acceptable salts thereof. This invention also provides pharmaceutical compositions which contain the triazolone derivatives and provides for their use to treat diseases, disorders and conditions associated with BTK.

One aspect of the invention provides compounds of Formula 1:

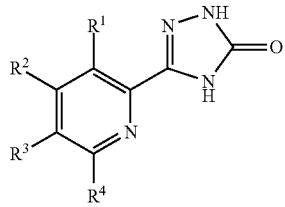

a tautomer thereof or a pharmaceutically acceptable salt of the compound or tautomer, wherein:

$R^1$ is selected from hydrogen, halo, —CN, $C_{1-4}$ alkyl, $C_{1-4}$ haloalkyl, and —$OR^{14}$;

$R^2$ and $R^3$ are each independently selected from hydrogen, halo, —CN, $R^6$, and $R^7$, or $R^2$ and $R^3$, together with carbon atoms to which they are attached, form a benzene ring or a pyridine ring in which the benzene ring is optionally substituted with from one to four substituents independently selected from halo, —CN, $R^6$, and $R^7$, and the pyridine ring is optionally substituted with from one to three substituents independently selected from halo, —CN, $R^6$, and $R^7$;

$R^4$ has the formula

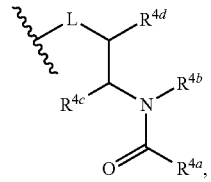

in which ⌇ indicates a point of attachment;

L is selected from —O—, —$CH_2O$—, and —$N(R^{4e})$—;

$R^{4a}$ is selected from —$CH_2R^5$ and ethenyl optionally substituted with from one to three substituents independently selected from halo, cyano, and $R^7$; and (a) $R^{4c}$ is hydrogen, $R^{4e}$ is selected from hydrogen and $C_{1-4}$ alkyl when L is —$N(R^{4e})$—, and $R^{4b}$ and $R^{4d}$, together with a nitrogen atom and carbon atoms to which $R^{4b}$, $R^{4c}$, and $R^{4d}$ are respectively attached, form a pyrrolidine ring or a piperidine ring, each ring optionally substituted with from one to six substituents independently selected from halo, $C_{1-4}$ alkyl, and $C_{1-4}$ haloalkyl; or (b) $R^{4b}$ is selected from hydrogen and $C_{1-4}$ alkyl, $R^{4d}$ is hydrogen, L is —$N(R^{4e})$—, and $R^{4c}$ and $R^{4e}$, together with the carbon atoms and a nitrogen atom to which $R^{4c}$, $R^{4d}$, and $R^{4e}$ are respectively attached, form a pyrrolidine ring or a piperidine ring, each ring optionally substituted with from one to six substituents independently selected from halo, $C_{1-4}$ alkyl, and $C_{1-4}$ haloalkyl; or (c) $R^{4d}$ is hydrogen, $R^{4e}$ is selected from hydrogen and $C_{1-4}$ alkyl when L is —$N(R^{4e})$—, and $R^{4b}$ and $R^{4c}$, together with the nitrogen and carbon atoms to which $R^{4b}$ and $R^{4c}$ are respectively attached, form pyrrolidine ring or a piperidine ring, each ring optionally substituted with from one to six substituents independently selected from halo, $C_{1-4}$ alkyl, and $C_{1-4}$ haloalkyl;

$R^5$ is selected from hydrogen, halo, and $C_{1-4}$ alkyl;

each $R^6$ is independently selected from —$OR^8$, —$N(R^8)R^9$, —$NR^8C(O)R^9$, —$NHC(O)NR^8R^9$, —$NR^8C(O)NHR^9$, —$C(O)R^8$, —$C(O)OR^8$, —$C(O)N(R^8)R^9$, —$C(O)N(R^8)OR^9$, —$C(O)N(R^8)S(O)_2R^7$, —$N(R^8)S(O)_2R^7$, —$SR^8$, —$S(O)R^7$, —$S(O)_2R^7$, and —$S(O)_2N(R^8)R^9$;

each $R^7$ is independently selected from
- (a) $C_{1-6}$ alkyl, $C_{2-6}$ alkenyl, and $C_{2-6}$ alkynyl, each optionally substituted with from one to five substituents independently selected from halo, oxo, —CN, and $R^{10}$; and
- (b) $C_{3-10}$ cycloalkyl-$(CH_2)_m$—, $C_{6-14}$ aryl-$(CH_2)_m$—, $C_{2-6}$ heterocyclyl-$(CH_2)_m$—, and $C_{1-9}$ heteroaryl-$(CH_2)_m$—, each optionally substituted with from one to five substituents independently selected from halo, oxo, —CN, $R^{10}$, and $C_{1-6}$ alkyl optionally substituted with from one to five substituents independently selected from halo, oxo, —CN, and $R^{10}$;

each $R^8$ and $R^9$ is independently selected from
- (a) hydrogen;
- (b) $C_{1-6}$ alkyl, $C_{2-6}$ alkenyl, and $C_{2-6}$ alkynyl, each optionally substituted with from one to five substituents independently selected from halo, oxo, —CN, and $R^{10}$; and
- (c) $C_{3-10}$ cycloalkyl-$(CH_2)_m$—, $C_{6-14}$ aryl-$(CH_2)_m$—, $C_{2-6}$ heterocyclyl-$(CH_2)_m$—, and $C_{1-9}$ heteroaryl-$(CH_2)_m$—, each optionally substituted with from one to five substituents independently selected from halo, oxo, —CN, $R^{10}$, and $C_{1-6}$ alkyl optionally substituted with from one to five substituents independently selected from halo, oxo, —CN, and $R^{10}$;

each $R^{10}$ is independently selected from —$OR^{11}$, —$N(R^{11})R^{12}$, —$N(R^{11})C(O)R^{12}$, —$NHC(O)NR^{11}R^{12}$, —$NR^{11}C(O)NHR^{12}$, —$C(O)R^{11}$, —$C(O)OR^{11}$, —$C(O)N(R^{11})R^{12}$, —$C(O)N(R^{11})OR^{12}$, —$C(O)N(R^{11})S(O)_2R^{13}$, —$NR^{11}S(O)_2R^{13}$, —$SR^{11}$, —$S(O)R^{13}$, —$S(O)_2R^{13}$, and —$S(O)_2N(R^{11})R^{12}$;

each $R^{11}$ and $R^{12}$ is independently selected from
- (a) hydrogen; and
- (b) $C_{1-6}$ alkyl and $C_{3-10}$ cycloalkyl-$(CH_2)_m$—, each optionally substituted with from one to five substituents independently selected from halo, oxo, —CN, —OH, and —$NH_2$;

each $R^{13}$ is independently selected from $C_{1-6}$ alkyl and $C_{3-10}$ cycloalkyl-$(CH_2)_m$—, each optionally substituted with from one to five substituents independently selected from halo, oxo, —CN, —OH, and —$NH_2$;

each $R^{14}$ is independently selected from hydrogen, $C_{1-4}$ alkyl, and $C_{1-4}$ haloalkyl; and each m is independently selected from 0, 1, 2, 3, and 4;

wherein each heteroaryl and heterocyclyl of $R^7$, $R^8$, and $R^9$ independently has one to four heteroatoms, each of the heteroatoms independently selected from N, O, and S.

Another aspect of the invention provides a compound which is selected from the group of compounds described in the examples, tautomers thereof, stereoisomers of the example compounds and their tautomers, and pharmaceutically acceptable salts of any of the aforementioned example compounds, tautomers, and stereoisomers.

A further aspect of the invention provides a pharmaceutical composition which includes a compound of Formula 1, a tautomer thereof or a pharmaceutically acceptable salt of the compound or tautomer as defined above, or a compound as defined in the immediately preceding paragraph; and a pharmaceutically acceptable excipient.

An additional aspect of the invention provides a compound of Formula 1, a tautomer thereof or a pharmaceutically acceptable salt of the compound or tautomer as defined above, or a compound selected from the group of compounds as defined above, for use as a medicament.

Another aspect of the invention provides a use of a compound of Formula 1, a tautomer thereof or a pharmaceutically acceptable salt of the compound or tautomer as defined above, or a compound selected from the group of compounds as defined above, for the manufacture of a medicament for the treatment of a condition associated with BTK.

An additional aspect of the invention provides a method for inhibiting BTK in a subject, the method comprising administering to the subject a compound of Formula 1, a tautomer thereof or a pharmaceutically acceptable salt of the compound or tautomer as defined above, or a compound selected from the group of compounds as defined above.

A further aspect of the invention provides a method of treating a disease, disorder or condition associated with BTK in a subject, the method comprising administering to the subject an effective amount of a compound of Formula 1, a tautomer thereof or a pharmaceutically acceptable salt of the compound or tautomer as defined above, or a compound selected from the group of compounds as defined above.

An additional aspect of the invention provides a method of treating a disease, disorder or condition in a subject, the method comprising administering to the subject an effective amount of a compound of Formula 1, a tautomer thereof or a pharmaceutically acceptable salt of the compound or tautomer as defined above, or a compound selected from the group of compounds as defined above, wherein the disease, disorder or condition is selected from Type I hypersensitivity reactions, autoimmune diseases, inflammatory disorders, cancer, and non-malignant proliferative disorders.

Another aspect of the invention provides a method of treating a disease, disorder or condition in a subject, the method comprising administering to the subject an effective amount of a compound of Formula 1, a tautomer thereof or a pharmaceutically acceptable salt of the compound or tautomer as defined above, or a compound selected from the group of compounds as defined above, wherein the disease, disorder or condition is selected from allergic rhinitis, asthma, atopic dermatitis, rheumatoid arthritis, multiple sclerosis, systemic lupus erythematosus, lupus nephritis, psoriasis, immune thrombocytopenic purpura, inflammatory bowel disease, chronic obstructive pulmonary disease, Sjögren's syndrome, ankylosing spondylitis, Behcet's disease, pemphigus vulgaris, idiopathic plasmacytic lymphadenopathy, atherosclerosis, myocardial infarction, and thrombosis.

Another aspect of the invention provides a method of treating a disease, disorder or condition in a subject, the method comprising administering to the subject an effective amount of a compound of Formula 1, a tautomer thereof or a pharmaceutically acceptable salt of the compound or tautomer as defined above, or a compound selected from the group of compounds as defined above, wherein the disease, disorder or condition is selected from B-cell lymphoma, chronic lymphocytic leukemia, and multiple myeloma.

A further aspect of the invention provides a combination of an effective amount of a compound of Formula 1, a tautomer thereof or a pharmaceutically acceptable salt of the compound or tautomer as defined above, or a compound selected from the group of compounds as defined above, and at least one additional pharmacologically active agent.

DETAILED DESCRIPTION OF THE INVENTION

Unless otherwise indicated, this disclosure uses definitions provided below.

"Substituted," when used in connection with a chemical substituent or moiety (e.g., a $C_{1-6}$ alkyl group), means that one or more hydrogen atoms of the substituent or moiety have been replaced with one or more non-hydrogen atoms or groups, provided that valence requirements are met and that a chemically stable compound results from the substitution.

"About" or "approximately," when used in connection with a measurable numerical variable, refers to the indicated value of the variable and to all values of the variable that are within the experimental error of the indicated value or within ±10 percent of the indicated value, whichever is greater.

"Alkyl" refers to straight chain and branched saturated hydrocarbon groups, generally having a specified number of carbon atoms (e.g., $C_{1-4}$ alkyl refers to an alkyl group having 1 to 4 (i.e., 1, 2, 3 or 4) carbon atoms, $C_{1-6}$ alkyl refers to an alkyl group having 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms. Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one or more halogen atoms, where alkyl, alkenyl, and alkynyl are defined above, and generally having a specified number of carbon atoms. Examples of haloalkyl groups include fluoromethyl, difluoromethyl, trifluoromethyl, chloromethyl, dichloromethyl, trichloromethyl, and the like.

"Cycloalkyl" refers to saturated monocyclic and bicyclic hydrocarbon groups, generally having a specified number of carbon atoms that comprise the ring or rings (e.g., $C_{3-10}$ cycloalkyl refers to a cycloalkyl group having 3 to 10 carbon atoms as ring members). Bicyclic hydrocarbon groups may include spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached through any ring atom unless such attachment would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like.

"Cycloalkylidene" refers to divalent monocyclic cycloalkyl groups, where cycloalkyl is defined above, which are attached through a single carbon atom of the group, and generally having a specified number of carbon atoms that comprise the ring (e.g., $C_{3-6}$ cycloalkylidene refers to a cycloalkylidene group having 3 to 6 carbon atoms as ring members). Examples include cyclopropylidene, cyclobutylidene, cyclopentylidene, and cyclohexylidene.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include spiro, fused, or bridged rings. Similarly, the cycloalkenyl group may be attached through any ring atom, and when stated, may include one or more non-hydrogen substituents unless such attachment or substitution would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo[2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The group may be attached through any ring atom unless such attachment would violate valence requirements. Examples of aryl groups include phenyl, cyclobutabenzenyl, indenyl, naphthalenyl, benzocycloheptanyl, biphenylenyl, fluorenyl, groups derived from cycloheptatriene cation, and the like.

"Arylene" refers to divalent aryl groups, where aryl is defined above. Examples of arylene groups include phenylene (i.e., benzene-1,2-diyl).

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-6}$ heterocyclyl refers to a heterocyclyl group having 2 to 6 carbon atoms and 1 to 4 heteroatoms as ring members). As with bicyclic cycloalkyl groups, bicyclic heterocyclyl groups may include spiro rings, fused rings, and bridged rings. The heterocyclyl group may be attached through any ring atom unless such attachment would violate valence requirements or result in a chemically unstable compound. Examples of monocyclic heterocyclyl groups include oxiranyl, thiiranyl, aziridinyl (e.g., aziridin-1-yl and aziridin-2-yl), oxetanyl, thietanyl, azetidinyl, tetrahydrofuranyl, tetrahydrothiopheneyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridine, 1,2,3,4-tetrahydropyridinyl, and 1,2,5,6-tetrahydropyridinyl.

"Heterocycle-diyl" refers to heterocyclyl groups which are attached through two ring atoms of the group, where heterocyclyl is defined above. They generally have a specified number of carbon atoms in their ring or rings (e.g., $C_{2-6}$ heterocycle-diyl refers to a heterocycle-diyl group having 2 to 6 carbon atoms and 1 to 4 heteroatoms as ring members). Examples of heterocycle-diyl groups include the multivalent analogs of the heterocycle groups described above, such as morpholine-3,4-diyl, pyrrolidine-1,2-diyl, 1-pyrrolidinyl-2-ylidene, 1-pyridinyl-2-ylidene, 1-(4H)-pyrazolyl-5-ylidene, 1-(3H)-imidazolyl-2-ylidene, 3-oxazolyl-2-ylidene, 1-piperidinyl-2-ylidene, 1-piperazinyl-6-ylidene, and the like.

"Heteroaromatic" and "heteroaryl" may be used interchangeably and refer to unsaturated monocyclic aromatic groups and to polycyclic groups having at least one aromatic ring, each of the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-9}$ heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached through any ring atom unless such attachment would violate valence requirements or result in a chemically unstable compound. Examples of heteroaryl groups include monocyclic groups such as pyrrolyl (e.g., pyrrol-1-yl, pyrrol-2-yl, and pyrrol-3-yl), furanyl, thiopheneyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothiopheneyl, benzo[c]thiopheneyl, indolyl, 3H-indolyl, isoindolyl, 1H-isoindolyl, indolinyl, isoindolinyl, benzimidazolyl, indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, and pyrimido[4,5-d]pyrimidinyl.

"Heteroarylene" refers to heteroaryl groups which are attached through two ring atoms of the group, where heteroaryl is defined above. They generally have a specified number of carbon atoms in their ring or rings (e.g., $C_{3-5}$ heteroarylene refers to a heteroarylene group having 3 to 5 carbon atoms and 1 to 4 heteroatoms as ring members). Examples of heteroarylene groups include the multivalent analogs of the heteroaryl groups described above, such as pyridine-2,3-diyl, pyridine-3,4-diyl, pyrazole-4,5-diyl, pyrazole-3,4-diyl, and the like.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2^-$ and $OH^-$ can be made better leaving groups by treatment with an acid. Common electrofugal leaving groups include the proton, $CO_2$, and metals.

"Opposite enantiomer" refers to a molecule that is a non-superimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refer to those substances which are suitable for administration to subjects.

"Treating" refers to reversing, alleviating, inhibiting the progress of, or preventing a disease, disorder or condition to which such term applies, or to reversing, alleviating, inhibiting the progress of, or preventing one or more symptoms of such disorder, disease or condition.

"Treatment" refers to the act of "treating," as defined immediately above.

"Drug," "drug substance," "active pharmaceutical ingredient," and the like, refer to a compound (e.g., compounds of Formula 1, including subgeneric compounds and compounds specifically named in the specification) that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Condition associated with BTK" and similar phrases relate to a disease, disorder or condition in a subject for which inhibition of BTK may provide a therapeutic or prophylactic benefit.

The following abbreviations are used throughout the specification: Ac (acetyl); ACN (acetonitrile); AIBN (azo-bis-isobutyronitrile); API (active pharmaceutical ingredient); aq (aqueous); Boc (tert-butoxycarbonyl); Cbz (carbobenzyloxy); CDI (1,1'-carbonyldiimidazole); dba (dibenzylideneacetone); DBU (1,8-diazabicyclo[5.4.0]undec-1(7)-ene); DCC (1,3-dicyclohexylcarbodiimide); DCM (dichloromethane); DIPEA (N,N-diisopropylethylamine, Hünig's Base); DMA (N,N-dimethylacetamide); DMAP (4-dimethylaminopyridine); DMARD (disease modifying antirheumatic drug); DME (1,2-dimethoxyethane); DMF (N,N-dimethylformamide); DMSO (dimethylsulfoxide); DPPA (diphenylphosphoryl azide); dppf (1,1'-bis(diphenylphosphino)ferrocene); DTT (dithiothreitol); EDA ethoxylated dodecyl alcohol, Brj®35); EDC (N-(3-dimethylaminopropyl)-N'-ethylcarbodiimide); EDTA (ethylenediaminetetraacetic acid); ee (enantiomeric excess); eq (equivalents); Et (ethyl); $Et_3N$ (triethyl-amine); EtOAc (ethyl acetate); EtOH (ethanol); 5-FAM (5-carboxyfluorescein); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); HOAc (acetic acid); HOBt (1H-benzo[d][1,2,3]triazol-1-ol); $IC_{50}$ (concentration at 50% inhibition); IPA (isopropanol); IPAc (isopropyl acetate); IPE (isopropylether); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); NaOt-Bu (sodium tertiary butoxide); NMM (N-methylmorpholine); NMP (1-methyl-2-pyrrolidinone); PE (petroleum ether); Ph (phenyl); $pIC_{50}$ ($-\log_{10}(IC_{50})$, where $IC_{50}$ is given in molar (M) units); Pr (propyl); i-Pr (isopropyl); PTFE (polytetrafluoroethylene); RT (room temperature, approximately 20° C. to 25° C.); TCEP (tris(2-carboxyethyl)phosphine); Tf (trifluoromethylsulfonyl); TFA (trifluoroacetic acid); TFAA (2,2,2-trifluoroacetic anhydride); THF (tetrahydrofuran); TMS (trimethylsilyl); and Tris buffer (2-amino-2-hydroxymethyl-propane-1,3-diol buffer).

As described, below, this disclosure concerns compounds of Formula 1, tautomers thereof, and pharmaceutically acceptable salts thereof. This disclosure also concerns materials and methods for preparing compounds of Formula 1, pharmaceutical compositions which contain them, and the use of compounds of Formula 1 and their pharmaceutically acceptable salts (optionally in combination with other pharmacologically active agents) for treating Type I hypersensitivity reactions, autoimmune diseases, inflammatory disorders, cancer, non-malignant proliferative disorders, and other diseases, disorders or conditions associated with BTK.

In addition to the specific compounds in the examples, compounds of Formula 1 include those in which: (i) $R^1$ is selected from hydrogen, halo, methyl, and $—OCH_3$; (ii) $R^1$ is selected from hydrogen, halo, and methyl; (iv) $R^1$ is selected from hydrogen and methyl; or (v) $R^1$ is hydrogen.

In addition, or as an alternative, to one of embodiments (i)-(v) in the immediately preceding paragraph, compounds of Formula 1 include those in which: (vi) $R^2$ and $R^3$ are each independently selected from hydrogen, halo, and methyl; (vii) $R^2$ and $R^3$ are each independently selected from hydrogen, fluoro, chloro, and methyl; (viii) $R^2$ is methyl and $R^3$ is hydrogen; (ix) $R^2$ is hydrogen and $R^3$ is methyl; or (x) $R^2$ and $R^3$ are each hydrogen.

In addition, or as an alternative, to one of embodiments (i)-(v) above, compounds of Formula 1 include those in which $R^2$ and $R^3$, together with the carbon atoms to which they are attached, form a benzene ring, and: (xi) the benzene ring is optionally substituted with from one to four substituents independently selected from halo, —CN, $R^6$, and $R^7$; (xii) the benzene ring is optionally substituted with from one to four substituents independently selected from halo and $C_{1-6}$ alkyl; (xiii) the benzene ring is optionally substituted with from one to four substituents independently selected from fluoro, chloro, and methyl; (xiv) the benzene ring is optionally substituted with one to two substituents independently selected from fluoro, chloro, and methyl; or (xv) the benzene ring is unsubstituted.

In addition, or as an alternative, to one of embodiments (i)-(v) above, compounds of Formula 1 include those in which $R^2$ and $R^3$, together with the carbon atoms to which they are attached, form a pyridine ring, and: (xvi) the pyridine ring is optionally substituted with from one to three substituents independently selected from halo, —CN, $R^6$, and $R^7$; (xvii) the pyridine ring is optionally substituted with from one to three substituents independently selected from halo and $C_{1-6}$ alkyl; (xviii) the pyridine ring is optionally substituted with from one to three substituents independently selected from fluoro, chloro, and methyl; (xix) the pyridine ring is optionally substituted with one or two substituents independently selected from fluoro, chloro, and methyl; or (xx) the pyridine ring is unsubstituted.

In addition, or as an alternative, to one of embodiments (i)-(v) above, compounds of Formula 1 include those in which $R^2$ and $R^3$, together with the carbon atoms to which they are attached, form a pyridine ring having a nitrogen ring atom that is directly bonded to the carbon atom attached to $R^3$, and: (xxi) the pyridine ring is optionally substituted with from one to three substituents independently selected from halo, —CN, $R^6$, and $R^7$; (xxii) the pyridine ring is optionally substituted with from one to three substituents independently selected from halo and $C_{1-6}$ alkyl; (xxiii) the pyridine ring is optionally substituted with from one to three substituents independently selected from fluoro, chloro, and methyl; (xxiv) the pyridine ring is optionally substituted with one or two substituents independently selected from fluoro, chloro, and methyl; or (xxv) the pyridine ring is unsubstituted.

In addition, or as an alternative, to one of embodiments (i)-(v) above, or to one of embodiments (vi)-(xxv) in the preceding paragraphs, compounds of Formula 1 include those in which L is —N($R^{4e}$)—, $R^{4c}$ is hydrogen, and $R^{4b}$ and $R^{4d}$, together with the nitrogen atom and the carbon atoms to which $R^{4b}$, $R^{4c}$, and $R^{4d}$ are respectively attached, form a pyrrolidine ring, and: (xxvi) $R^{4e}$ is selected from hydrogen and $C_{1-4}$ alkyl, and the pyrrolidine ring is optionally substituted with from one to six substituents independently selected from halo, $C_{1-4}$ alkyl, and $C_{1-4}$ haloalkyl; (xxvii) $R^{4e}$ is selected from hydrogen and $C_{1-4}$ alkyl, and the pyrrolidine ring is optionally substituted with from one to four substituents independently selected from halo, $C_{1-4}$ alkyl, and $C_{1-4}$ haloalkyl; (xxviii) $R^{4e}$ is hydrogen and the pyrrolidine ring is optionally substituted with from one to four substituents independently selected from halo, $C_{1-4}$ alkyl, and $C_{1-4}$ haloalkyl; (xxix) $R^{4e}$ is hydrogen and the pyrrolidine ring is optionally substituted with one or two substituents independently selected from halo, $C_{1-4}$ alkyl, and $C_{1-4}$ haloalkyl; or (xxx) $R^{4e}$ is hydrogen and the pyrrolidine ring is unsubstituted.

In addition, or as an alternative, to one of embodiments (i)-(v) above, or to one of embodiments (vi)-(xxv) in the preceding paragraphs, compounds of Formula 1 include those in which L is —N($R^{4e}$)—, $R^{4c}$ is hydrogen, and $R^{4b}$ and $R^{4d}$, together with the nitrogen atom and the carbon atoms to which $R^{4b}$, $R^{4c}$, and $R^{4d}$ are respectively attached, form a piperidine ring, and: (xxxi) $R^{4e}$ is selected from hydrogen and $C_{1-4}$ alkyl, and the piperidine ring is optionally substituted with from one to six substituents independently selected from halo, $C_{1-4}$ alkyl, and $C_{1-4}$ haloalkyl; (xxxii) $R^{4e}$ is selected from hydrogen and $C_{1-4}$ alkyl, and the piperidine ring is optionally substituted with from one to four substituents independently selected from halo, $C_{1-4}$ alkyl, and $C_{1-4}$ haloalkyl; (xxxiii) $R^{4e}$ is hydrogen and the piperidine ring is optionally substituted with from one to four substituents independently selected from halo, $C_{1-4}$ alkyl, and $C_{1-4}$ haloalkyl; (xxxiv) $R^{4e}$ is hydrogen and the piperidine ring is optionally substituted with one or two substituents independently selected from halo, $C_{1-4}$ alkyl, and $C_{1-4}$ haloalkyl; or (xxxv) $R^{4e}$ is hydrogen and the piperidine ring is unsubstituted.

In addition, or as an alternative, to one of embodiments (i)-(v) above, or to one of embodiments (vi)-(xxv) in the preceding paragraphs, compounds of Formula 1 include those in which L is —N($R^{4e}$)—, $R^{4d}$ is hydrogen, and $R^{4c}$ and $R^{4e}$, together with the carbon atoms and the nitrogen atom to which $R^{4c}$, $R^{4d}$, and $R^{4e}$ are respectively attached, form a pyrrolidine ring, and: (xxxvi) $R^{4b}$ is selected from hydrogen and $C_{1-4}$ alkyl, and the pyrrolidine ring is optionally substituted with from one to six substituents independently selected from halo, $C_{1-4}$ alkyl, and $C_{1-4}$ haloalkyl; (xxxvii) $R^{4b}$ is selected from hydrogen and $C_{1-4}$ alkyl, and the pyrrolidine ring is optionally substituted with from one to four substituents independently selected from halo, $C_{1-4}$ alkyl, and $C_{1-4}$ haloalkyl; (xxxviii) $R^{4b}$ is hydrogen and the pyrrolidine ring is optionally substituted with from one to four substituents independently selected from halo, $C_{1-4}$ alkyl, and $C_{1-4}$ haloalkyl; (xxxix) $R^{4b}$ is hydrogen and the pyrrolidine ring is optionally substituted with one or two substituents independently selected from halo, $C_{1-4}$ alkyl, and $C_{1-4}$ haloalkyl; or (xl) $R^{4b}$ is hydrogen and the pyrrolidine ring is unsubstituted.

In addition, or as an alternative, to one of embodiments (i)-(v) above, or to one of embodiments (vi)-(xxv) in the preceding paragraphs, compounds of Formula 1 include those in which L is —N($R^{4e}$)—, $R^{4d}$ is hydrogen, and $R^{4c}$ and $R^{4e}$, together with the carbon atoms and the nitrogen atom to which $R^{4c}$, $R^{4d}$, and $R^{4e}$ are respectively attached, form a piperidine ring, and: (xli) $R^{4b}$ is selected from hydrogen and $C_{1-4}$ alkyl, and the piperidine ring is optionally substituted with from one to six substituents independently selected from halo, $C_{1-4}$ alkyl, and $C_{1-4}$ haloalkyl; (xlii) $R^{4b}$ is selected from hydrogen and $C_{1-4}$ alkyl, and the piperidine ring is optionally substituted with from one to four substituents independently selected from halo, $C_{1-4}$ alkyl, and $C_{1-4}$ haloalkyl; (xliii) $R^{4b}$ is hydrogen and the piperidine ring is optionally substituted with from one to four substituents independently selected from halo, $C_{1-4}$ alkyl, and $C_{1-4}$ haloalkyl; (xliv) $R^{4b}$ is hydrogen and the piperidine ring is optionally substituted with one or two substituents independently selected from halo, $C_{1-4}$ alkyl, and $C_{1-4}$ haloalkyl; or (xlv) $R^{4b}$ is hydrogen and the piperidine ring is unsubstituted.

In addition, or as an alternative, to one of embodiments (i)-(v) above, or to one of embodiments (vi)-(xxv) in the preceding paragraphs, compounds of Formula 1 include those in which L is —N($R^{4e}$)—, $R^{4d}$ is hydrogen, and $R^{4b}$ and $R^{4c}$, together with the nitrogen and carbon atoms to which $R^{4b}$ and $R^{4c}$ are respectively attached, form a pyrrolidine ring, and: (xlvi) $R^{4e}$ is selected from hydrogen and $C_{1-4}$ alkyl, and the pyrrolidine ring is optionally substituted with from one to six substituents independently selected from halo, $C_{1-4}$ alkyl, and $C_{1-4}$ haloalkyl; (xlvii) $R^{4e}$ is selected from hydrogen and $C_{1-4}$ alkyl, and the pyrrolidine ring is optionally substituted with from one to four substituents independently selected from halo, $C_{1-4}$ alkyl, and $C_{1-4}$ haloalkyl; (xlviii) $R^{4e}$ is hydrogen and the pyrrolidine ring is optionally substituted with from one to four substituents independently selected from halo, $C_{1-4}$ alkyl, and $C_{1-4}$ haloalkyl; (xlix) $R^{4e}$ is hydrogen and the pyrrolidine ring is optionally substituted with one or two substituents independently selected from halo, $C_{1-4}$ alkyl, and $C_{1-4}$ haloalkyl; or (l) $R^{4e}$ is hydrogen and the pyrrolidine ring is unsubstituted.

In addition, or as an alternative, to one of embodiments (i)-(v) above, or to one of embodiments (vi)-(xxv) in the preceding paragraphs, compounds of Formula 1 include those in which L is —N($R^{4e}$)—, $R^{4d}$ is hydrogen, and $R^{4b}$ and $R^{4c}$, together with the nitrogen and carbon atoms to which $R^{4b}$ and $R^{4c}$ are respectively attached, form a piperidine ring, and: (li) $R^{4e}$ is selected from hydrogen and $C_{1-4}$ alkyl, and the piperidine ring is optionally substituted with from one to six substituents independently selected from halo, $C_{1-4}$ alkyl, and $C_{1-4}$ haloalkyl; (lii) $R^{4e}$ is selected from hydrogen and $C_{1-4}$ alkyl, and the piperidine ring is optionally substituted with from one to four substituents independently selected from halo, $C_{1-4}$ alkyl, and $C_{1-4}$ haloalkyl; (liii) $R^{4e}$ is hydrogen and the piperidine ring is optionally substituted with from one to four substituents independently selected from halo, $C_{1-4}$ alkyl, and $C_{1-4}$ haloalkyl; (liv) $R^{4e}$ is hydrogen and the piperidine ring is optionally substituted with one or two substituents independently selected from halo, $C_{1-4}$ alkyl, and $C_{1-4}$ haloalkyl; or (lv) $R^{4e}$ is hydrogen and the piperidine ring is unsubstituted.

In addition, or as an alternative, to one of embodiments (i)-(v) above, or to one of embodiments (vi)-(xxv) in the preceding paragraphs, compounds of Formula 1 include those in which L is —O—, $R^{4c}$ is hydrogen, and $R^{4b}$ and $R^{4d}$, together with the nitrogen atom and the carbon atoms to which $R^{4b}$, $R^{4c}$, and $R^{4d}$ are respectively attached, form a pyrrolidine ring, and: (lvi) the pyrrolidine ring is optionally substituted with from one to six substituents independently selected from halo, $C_{1-4}$ alkyl, and $C_{1-4}$ haloalkyl; (lvii) the pyrrolidine ring is optionally substituted with from one to four substituents independently selected from halo, $C_{1-4}$ alkyl, and $C_{1-4}$ haloalkyl; (lviii) the pyrrolidine ring is optionally substituted with from one to three substituents independently selected from halo, $C_{1-4}$ alkyl, and $C_{1-4}$ haloalkyl; (lix) the pyrrolidine ring is optionally substituted with one or two substituents independently selected from halo, $C_{1-4}$ alkyl, and $C_{1-4}$ haloalkyl; or (lx) the pyrrolidine ring is unsubstituted.

In addition, or as an alternative, to one of embodiments (i)-(v) above, or to one of embodiments (vi)-(xxv) in the preceding paragraphs, compounds of Formula 1 include those in which L is —O—, $R^{4c}$ is hydrogen, and $R^{4b}$ and $R^{4d}$, together with the nitrogen atom and the carbon atoms to which $R^{4b}$, $R^{4c}$, and $R^{4d}$ are respectively attached, form a piperidine ring, and: (lxi) the piperidine ring is optionally substituted with from one to six substituents independently selected from halo, $C_{1-4}$ alkyl, and $C_{1-4}$ haloalkyl; (lxii) the piperidine ring is optionally substituted with from one to four substituents independently selected from halo, $C_{1-4}$ alkyl, and $C_{1-4}$ haloalkyl; (lxiii) the piperidine ring is optionally substituted with from one to three substituents independently selected from halo, $C_{1-4}$ alkyl, and $C_{1-4}$ haloalkyl; (lxiv) the piperidine ring is optionally substituted with one or two substituents independently selected from halo, $C_{1-4}$ alkyl, and $C_{1-4}$ haloalkyl; or (lxv) the piperidine ring is unsubstituted.

In addition, or as an alternative, to one of embodiments (i)-(v) above, or to one of embodiments (vi)-(xxv) in the preceding paragraphs, compounds of Formula 1 include those in which L is —O—, $R^{4d}$ is hydrogen, and $R^{4b}$ and $R^{4c}$, together with the nitrogen and carbon atoms to which $R^{4b}$ and $R^{4c}$ are respectively attached, form a pyrrolidine ring, and: (lxvi) the pyrrolidine ring is optionally substituted with from one to six substituents independently selected from halo, $C_{1-4}$ alkyl, and $C_{1-4}$ haloalkyl; (lxvii) the pyrrolidine ring is optionally substituted with from one to four substituents independently selected from halo, $C_{1-4}$ alkyl, and $C_{1-4}$ haloalkyl; (lxviii) the pyrrolidine ring is optionally substituted with from one to three substituents independently selected from halo, $C_{1-4}$ alkyl, and $C_{1-4}$ haloalkyl; (lxix) the pyrrolidine ring is optionally substituted with one or two substituents independently selected from halo, $C_{1-4}$ alkyl, and $C_{1-4}$ haloalkyl; or (lxx) the pyrrolidine ring is unsubstituted.

In addition, or as an alternative, to one of embodiments (i)-(v) above, or to one of embodiments (vi)-(xxv) in the preceding paragraphs, compounds of Formula 1 include those in which L is —O—, $R^{4d}$ is hydrogen, and $R^{4b}$ and $R^{4c}$, together with the nitrogen and carbon atoms to which $R^{4b}$ and $R^{4c}$ are respectively attached, form a piperidine ring, and: (lxxi) the piperidine ring is optionally substituted with from one to six substituents independently selected from halo, $C_{1-4}$ alkyl, and $C_{1-4}$ haloalkyl; (lxxii) the piperidine ring is optionally substituted with from one to four substituents independently selected from halo, $C_{1-4}$ alkyl, and $C_{1-4}$ haloalkyl; (lxxiii) the piperidine ring is optionally substituted with from one to three substituents independently selected from halo, $C_{1-4}$ alkyl, and $C_{1-4}$ haloalkyl; (lxxiv) the piperidine ring is optionally substituted with one or two substituents independently selected from halo, $C_{1-4}$ alkyl, and $C_{1-4}$ haloalkyl; or (lxxv) the piperidine ring is unsubstituted.

In addition, or as an alternative, to one of embodiments (i)-(v) above, or to one of embodiments (vi)-(xxv) in the preceding paragraphs, compounds of Formula 1 include those in which L is —CH$_2$O—, $R^{4c}$ is hydrogen, and $R^{4b}$ and $R^{4d}$, together with the nitrogen atom and the carbon atoms to which $R^{4b}$, $R^{4c}$, and $R^{4d}$ are respectively attached, form a pyrrolidine ring, and: (lxxvi) the pyrrolidine ring is optionally substituted with from one to six substituents independently selected from halo, $C_{1-4}$ alkyl, and $C_{1-4}$ haloalkyl; (lxxvii) the pyrrolidine ring is optionally substituted with from one to four substituents independently selected from halo, $C_{1-4}$ alkyl, and $C_{1-4}$ haloalkyl; (lxxviii) the pyrrolidine ring is optionally substituted with from one to three substituents independently selected from halo, $C_{1-4}$ alkyl, and $C_{1-4}$ haloalkyl; (lxxix) the pyrrolidine ring is optionally substituted with one or two substituents independently selected from halo, $C_{1-4}$ alkyl, and $C_{1-4}$ haloalkyl; or (lxxx) the pyrrolidine ring is unsubstituted; wherein in embodiments (lxxvi)-(lxxx), the O atom of L is directly bonded to the carbon atom attached to $R^{4d}$.

In addition, or as an alternative, to one of embodiments (i)-(v) above, or to one of embodiments (vi)-(xxv) in the preceding paragraphs, compounds of Formula 1 include those in which L is —CH$_2$O—, $R^{4c}$ is hydrogen, and $R^{4b}$ and $R^{4d}$, together with the nitrogen atom and the carbon atoms to which $R^{4b}$, $R^{4c}$, and $R^{4d}$ are respectively attached, form a piperidine ring, and: (lxxxi) the piperidine ring is optionally substituted with from one to six substituents independently selected from halo, $C_{1-4}$ alkyl, and $C_{1-4}$ haloalkyl; (lxxxii) the piperidine ring is optionally substituted with from one to four substituents independently selected from halo, $C_{1-4}$ alkyl, and $C_{1-4}$ haloalkyl; (lxxxiii) the piperidine ring is optionally substituted with from one to three substituents independently selected from halo, $C_{1-4}$ alkyl, and $C_{1-4}$ haloalkyl; (lxxxiv) the piperidine ring is optionally substituted with one or two substituents independently selected from halo, $C_{1-4}$ alkyl, and $C_{1-4}$ haloalkyl; or (lxxxv) the piperidine ring is unsubstituted; wherein in embodiments (lxxxi)-(lxxxv), the O atom of L is directly bonded to the carbon atom attached to $R^{4d}$.

In addition, or as an alternative, to one of embodiments (i)-(v) above, or to one of embodiments (vi)-(xxv) in the preceding paragraphs, compounds of Formula 1 include those in which L is —CH$_2$O—, $R^{4d}$ is hydrogen, and $R^{4b}$ and $R^{4c}$, together with the nitrogen and carbon atoms to which $R^{4b}$ and $R^{4c}$ are respectively attached, form a pyrrolidine ring, and: (lxxxvi) the pyrrolidine ring is optionally substituted with from one to six substituents independently selected from halo, $C_{1-4}$ alkyl, and $C_{1-4}$ haloalkyl; (lxxxvii) the pyrrolidine ring is optionally substituted with from one to four substituents independently selected from halo, $C_{1-4}$ alkyl, and $C_{1-4}$ haloalkyl; (lxxxviii) the pyrrolidine ring is optionally substituted with from one to three substituents independently selected from halo, $C_{1-4}$ alkyl, and $C_{1-4}$ haloalkyl; (lxxxix) the pyrrolidine ring is optionally substituted with one or two substituents independently selected from halo, $C_{1-4}$ alkyl, and $C_{1-4}$ haloalkyl; or (xc) the pyrrolidine ring is unsubstituted; wherein in embodiments (lxxxvi)-(xc), the O atom of L is directly bonded to the carbon atom attached to $R^{4d}$.

In addition, or as an alternative, to one of embodiments (i)-(v) above, or to one of embodiments (vi)-(xxv) in the preceding paragraphs, compounds of Formula 1 include those in which L is —CH$_2$O—, $R^{4d}$ is hydrogen, and $R^{4b}$ and $R^{4c}$, together with the nitrogen and carbon atoms to which $R^{4b}$ and $R^{4c}$ are respectively attached, form a piperidine ring, and: (xci) the piperidine ring is optionally substituted with from one to six substituents independently selected from halo, $C_{1-4}$ alkyl, and $C_{1-4}$ haloalkyl; (xcii) the piperidine ring is optionally substituted with from one to four substituents independently selected from halo, $C_{1-4}$ alkyl, and $C_{1-4}$ haloalkyl; (xciii) the piperidine ring is optionally substituted with from one to three substituents independently selected from halo, $C_{1-4}$ alkyl, and $C_{1-4}$ haloalkyl; (xciv) the piperidine ring is optionally substituted with one or two substituents independently selected from halo, $C_{1-4}$ alkyl, and $C_{1-4}$ haloalkyl; or (xcv) the piperidine ring is unsubstituted; wherein in embodiments (xci)-(xcv), the O atom of L is directly bonded to the carbon atom attached to $R^{4d}$.

In addition, or as an alternative, to one of embodiments (i)-(v) above, to one of embodiments (vi)-(xxv) above, or to one of embodiments (xxvi)-(xcv) in the preceding paragraphs, compounds of Formula 1 include those in which: (xcvi) $R^{4a}$ is ethenyl optionally substituted with from one to three substituents independently selected from halo, cyano, and $R^7$; (xcvii) $R^{4a}$ is ethenyl optionally substituted with from one to three methyl groups; (xcviii) $R^{4a}$ is ethenyl optionally substituted with one or two substituents independently selected from halo, cyano, and $R^7$; (xcix) $R^{4a}$ is ethenyl optionally substituted with one or two methyl groups; or (c) $R^{4a}$ is ethenyl.

In addition, or as an alternative, to one of embodiments (i)-(v) above, to one of embodiments (vi)-(xxv) above, to one of embodiments (xxvi)-(xcv) above, and to one of embodiments (xcvi)-(c) in the immediately preceding paragraph, compounds of Formula 1 include those in which: (ci) each m is independently selected from 0, 1, 2, and 3; (cii) each m is independently selected from 0, 1, and 2; (ciii) each m is independently selected from 0 and 1; or (civ) each m is 0.

Compounds of Formula 1, including embodiments (i) through (civ) described in the preceding paragraphs and all compounds specifically named in the examples, may exist as salts, complexes, solvates, hydrates, and liquid crystals. Likewise, compounds of Formula 1 that are salts may exist as complexes, solvates, hydrates, and liquid crystals.

Compounds of Formula 1 may form pharmaceutically acceptable complexes, salts, solvates and hydrates. These salts include acid addition salts (including di-acids) and base salts. Pharmaceutically acceptable acid addition salts include salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include salts derived from bases, including metal cations, such as an alkali or alkaline earth metal cation, as well as amines. Examples of suitable metal cations include sodium, potassium, magnesium, calcium, zinc, and aluminum. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2002).

Pharmaceutically acceptable salts may be prepared using various methods. For example, a compound of Formula 1 may be reacted with an appropriate acid or base to give the desired salt. Alternatively, a precursor of the compound of Formula 1 may be reacted with an acid or base to remove an acid- or base-labile protecting group or to open a lactone or lactam group of the precursor. Additionally, a salt of the compound of Formula 1 may be converted to another salt (or free form) through treatment with an appropriate acid or base or through contact with an ion exchange resin. Following reaction, the salt may be isolated by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., ethanol). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896. For a general review of multi-component complexes, see J. K. Haleblian, *J. Pharm. Sci.* (1975) 64(8):1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., —COO$^-$Na$^+$, —COO$^-$K$^+$, —SO$_3^-$Na$^+$) or polar non-ionic moiety (such as —N$^-$N$^+$(CH$_3$)$_3$). See, e.g., N. H. Hartshorne and A. Stuart, *Crystals and the Polarizing Microscope* (4th ed, 1970).

Each compound of Formula 1 may exist as polymorphs, stereoisomers, tautomers, or some combination thereof, may be isotopically-labeled, may result from the administration of a prodrug, or form a metabolite following administration.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Compounds of Formula 1 may exist as stereoisomers that result from the presence of one or more stereogenic centers, one or more double bonds, or both. The stereoisomers may be pure, substantially pure, or mixtures. Such stereoisomers may also result from acid addition or base salts in which the counter-ion is optically active, for example, when the counter-ion is D-lactate or L-lysine.

Compounds of Formula 1 may exist as tautomers, which are isomers resulting from tautomerization. Examples of tautomeric isomerism include imine-enamine, keto-enol, oxime-nitroso, and amide-imidic acid tautomerism. The triazolone moiety of Formula 1 may exist, for example, in the following tautomeric forms:

or derivative) using, for example, chiral high pressure liquid chromatography (HPLC). Alternatively, the racemate (or a racemic precursor) may be reacted with a suitable optically active compound, for example, an alcohol, or, in the case where the compound of Formula 1 contains an acidic or basic moiety, an acid or base such as tartaric acid or 1-phenylethylamine. The resulting diastereomeric mixture may be separated by chromatography, fractional crystallization, etc., and the appropriate diastereoisomer converted to the compound having the requisite stereochemical configuration. For a further discussion of techniques for separating stereoisomers, see E. L. Eliel and S. H. Wilen, *Stereochemistry of Organic Compounds* (1994).

Compounds of Formula 1 may possess isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^2$H and $^3$H; isotopes of carbon, such as $^{11}$C, $^{13}$C and $^{14}$C; isotopes of nitrogen, such as $^{13}$N and $^{15}$N; isotopes of oxygen, such as $^{15}$O, $^{17}$O and $^{18}$O; isotopes of sulfur, such as $^{35}$S; isotopes of fluorine, such as $^{18}$F; isotopes of chlorine, such as $^{36}$Cl, and isotopes of iodine, such as $^{123}$I and $^{125}$I. Use of isotopic variations (e.g., deuterium, $^2$H) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3$H, or $^{14}$C), which may be useful in drug and/or substrate tissue distribution studies. Substitution with positron emitting isotopes, such as $^{11}$C, $^{18}$F, $^{15}$O and $^{13}$N, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations* (1999), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical

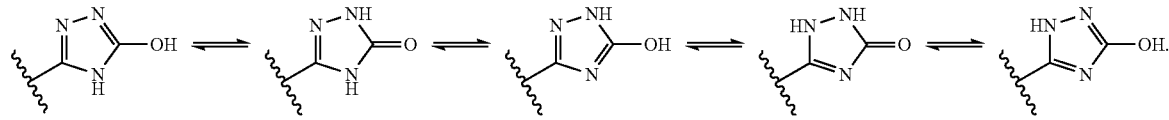

Compounds of Formula 1 may exhibit more than one type of isomerism.

Geometrical (cis/trans) isomers may be separated by conventional techniques such as chromatography and fractional crystallization.

Conventional techniques for preparing or isolating a compound having a specific stereochemical configuration include chiral synthesis from a suitable optically pure precursor or resolution of the racemate (or the racemate of a salt transformations (e.g., an alcohol from the hydrolysis of an ester, CO$_2$ from the decarboxylation of a di-acid, etc.). In addition, in some instances, reaction intermediates may be used in subsequent steps without isolation or purification (i.e., in situ).

In some of the reaction schemes and examples below, certain compounds may be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxyethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

In the schemes, below, substituent identifiers (e.g., $R^1$, $R^2$, $R^3$, etc.) are as defined above for Formula 1. As mentioned earlier, however, some of the starting materials and intermediates may include protecting groups, which are removed prior to the final product. In such cases, the substituent identifier refers to moieties defined in Formula 1 and to those moieties with appropriate protecting groups. For example, a starting material or intermediate in the schemes may include a substituent identifier that is a moiety having a potentially reactive amine. In such cases, the substituent identifier would include the moiety with or without, say, a Boc or Cbz group attached to the amine.

Schemes A and B depict general methods for preparing compounds of Formula 1 in which L is —O— or —N($R^{4e}$)—. As shown in Scheme A, a dihalopyridine derivative (A1) is reacted with an alcohol (A2) or an amine (A3) in the presence of a nonnucleophilic or inorganic base (e.g., NaH, $Et_3N$, $Cs_2CO_3$, etc.). In Formula A1, X is halo (typically Cl or Br), and in Formula A2 and A3, PG is an amine protective group, such as Boc. The reaction is carried out in a compatible solvent (e.g., NMP, DMF, THF, etc.) and at a temperature which may range from RT to about 140° C. The resulting intermediate (A4, in which $L^1$ is —O— or —N($R^{4e}$)—) is reacted with zinc cyanide in the presence of a palladium catalyst (e.g., Pd(PPh$_3$)$_4$) and solvent (e.g., DMF, DMA, etc.) and at elevated temperature (e.g., about 150-165° C.). The resulting nitrile (A5) is combined with ethyl hydrazinecarboxylate in a compatible solvent (e.g., NMP) and is heated (e.g., at about 175° C.) to give a triazolone intermediate (A6). Subsequent removal of the amine protective group (e.g., via treatment with an acid when PG is Boc) and reaction with an acyl chloride (A7) in the presence of a nonnucleophilic base (e.g., 2,6-dimethyl-pyridine) and a compatible solvent (e.g., DCM, NMP, DMSO, etc.) give the desired compound of Formula 1A.

Scheme A

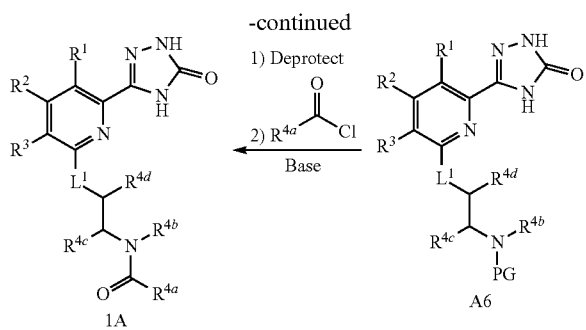

Scheme B provides an alternative method for installing the triazolone moiety. As in Scheme A, a dihalopyridine derivative (A1) is reacted with an alcohol (A2) or an amine (A3) in the presence of a nonnucleophilic or inorganic base, and the resulting intermediate (A4) is reacted with zinc cyanide in the presence of a palladium catalyst and solvent. In contrast to Scheme A, the resulting nitrile (A5) is combined with hydrazine hydrate in a compatible solvent (e.g., MeOH) and is heated at elevated temperature (e.g., reflux) to give a picolinimidohydrazide intermediate (B1). The picolinimidohydrazide derivative (B1) is subsequently reacted with 1,1'-carbonyldiimidazole (CDI) in a compatible solvent (e.g., dioxane) and at elevated temperature (e.g., reflux) to give a triazolone intermediate (A6). As in Scheme A, the protective group (PG) is removed and the resulting amine (not shown) is reacted with an acyl chloride (A7) in the presence of a nonnucleophilic base and a compatible solvent to give the desired compound of Formula 1A.

Scheme C depicts a general method for preparing compounds of Formula 1 in which L is —CH$_2$O—. As shown in Scheme C, a picolinic acid derivative (C1) is reacted with methanol and sulfuric acid at elevated temperature (e.g., about 65° C.). The resulting methyl picolinate derivative (C2) is activated via treatment with m-chloroperoxybenzoic acid in a compatible solvent (e.g., DCM) to give and N-oxide intermediate (C3) which is subsequently reacted with phosphoryl trichloride at elevated temperature (e.g., about 100° C.). The resulting methyl 6-chloropicolinate derivative (C4) is treated with sodium borohydride and methanol to give a (6-chloropyridin-2-yl)methanol derivative (C5) which is reacted with zinc cyanide in the presence of a palladium catalyst (e.g. Pd$_2$(dba)$_3$), an optional ligand (e.g., XPhos) and solvent (e.g., DMF, DMA, etc.) at elevated temperature (e.g., about 150-165° C.). The resulting 6-(hydroxymethyl)picolinonitrile derivative (C6) is reacted with tribromophosphine in a compatible solvent (e.g., THF) to give a brominated intermediate (C7) which is reacted with an alcohol (A2) in the presence of a base to give a nitrile (C8) in which L$^2$ is —CH$_2$O—. As in Scheme A, the nitrile (C8) is combined with ethyl hydrazinecarboxylate in a compatible solvent and is heated to give a triazolone intermediate (C9). Subsequent removal of the amine protective group and reaction with an acyl chloride (A7) in the presence of a nonnucleophilic base and a compatible solvent gives the desired compound of Formula 1B.

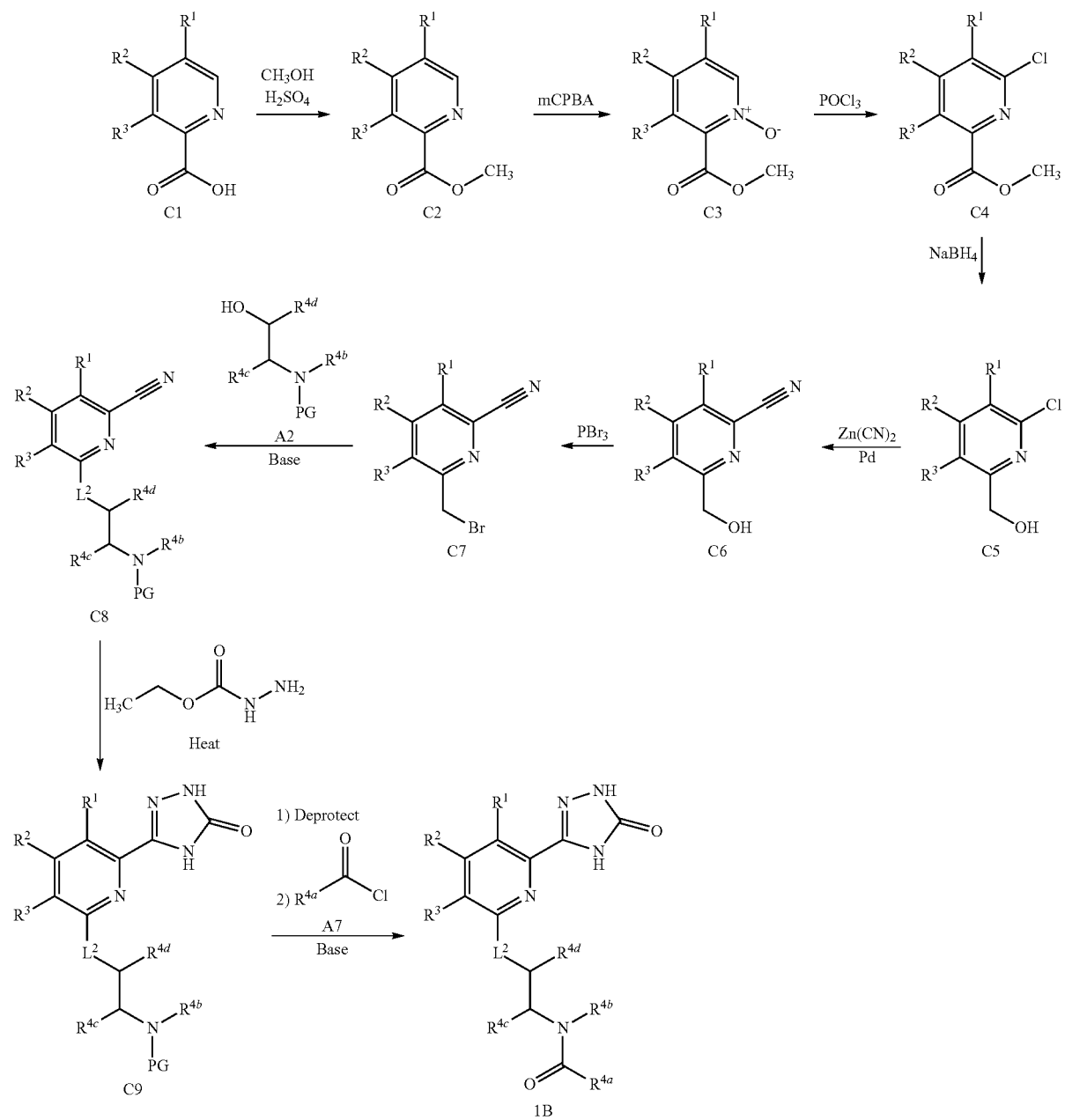

The methods depicted in Schemes A, B, and C may be varied as desired. For example, additional protecting groups may be added or removed at various steps in the routes. The intermediates may be further elaborated via, for example, alkylation, acylation, hydrolysis, oxidation, reduction, amidation, sulfonation, alkynation, and the like to give the desired final product. Furthermore, any racemic intermediate may be optionally purified by chiral column chromatography (e.g., supercritical fluid chromatography) or by derivatization with optically-pure reagents as described above, to give a desired stereoisomer.

Compounds of Formula 1, which include compounds named in the examples, and their pharmaceutically acceptable complexes, salts, solvates and hydrates, should be assessed for their biopharmaceutical properties, such as solubility and solution stability across pH, permeability, and the like, to select an appropriate dosage form and route of administration. Compounds that are intended for pharmaceutical use may be administered as crystalline or amorphous products, and may be obtained, for example, as solid plugs, powders, or films by methods such as precipitation, crystallization, freeze drying, spray drying, evaporative drying, microwave drying, or radio frequency drying.

Compounds of Formula 1 may be administered alone or in combination with one another or with one or more pharmacologically active compounds which are different than the compounds of Formula 1. Generally, one or more these compounds are administered as a pharmaceutical composition (a formulation) in association with one or more pharmaceutically acceptable excipients. The choice of excipients depends on the particular mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

Compounds of Formula 1 may be administered orally. Oral administration may involve swallowing in which case the compound enters the bloodstream via the gastrointestinal tract. Alternatively or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets, Vol.* 1-3 (2d ed., 1990); and D. K. Parikh & C. K. Parikh, *Handbook of Pharmaceutical Granulation Technology*, Vol. 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include anti-oxidants, colorants, flavorants and flavor enhancers, preservatives, salivary stimulating agents, cooling agents, co-solvents (including oils), emollients, bulking agents, anti-foaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14.

Compounds of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula 1 may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula 1 may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic)acid (PGLA) microspheres.

Compounds of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol.

Topical formulations may also include penetration enhancers. See, e.g., Finnin and Morgan, *J. Pharm. Sci.* 88(10): 955-958 (1999).

Other means of topical administration include delivery by electroporation, iontophoresis, phonophoresis, sonophoresis and microneedle or needle-free (e.g. Powderject™ and Bioject™) injection. Formulations for topical administration may be formulated to be immediate or modified release as described above.

Compounds of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3,3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 µg to about 20 mg of the API per actuation and the actuation volume may vary from about 1 µL to about 100 µL. A typical formulation may comprise one or more compounds of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 µg to about 1000 µg of the API. The overall daily dose will typically range from about 100 µg to about 10 mg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

Compounds of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinylalcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 91/11172, WO 94/02518, and WO 98/55148.

As noted above, one or more compounds of Formula 1, including compounds specifically named in the examples, and their pharmaceutically active complexes, salts, solvates and hydrates, may be combined with each other or with one or more other active pharmaceutically active compounds to treat various diseases, disorders or conditions. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

As noted above, the compounds of Formula 1 may be used to treat diseases, disorders or conditions for which inhibition of BTK is indicated. Such diseases, disorders or conditions generally relate to any unhealthy or abnormal state in a subject for which the inhibition of BTK provides a therapeutic benefit. More particularly, such diseases, disorders or conditions may involve the immune system and inflammation, including Type I hypersensitivity (allergic) reactions (allergic rhinitis, allergic asthma, and atopic dermatitis); autoimmune diseases (rheumatoid arthritis, multiple sclerosis, systemic lupus erythematosus, psoriasis, lupus nephritis, immune thrombocytopenic purpura, Sjögren's syndrome, ankylosing spondylitis, and Behcet's disease); inflammatory bowel disease; inflammation of the lung (chronic obstructive pulmonary disease), atherosclerosis, thrombosis, and myocardial infarction. The compounds of Formula 1 may also be used to treat diseases, disorders or conditions related to abnormal cell growth, including hematological malignancies, such as acute myeloid leukemia, B-cell chronic lymphocytic leukemia, B-cell lymphoma (e.g., mantle cell lymphoma), T-cell lymphoma (e.g., peripheral T-cell lymphoma), and multiple myeloma, as well as epithelial cancers (i.e., carcinomas), such as lung cancer (small cell lung cancer and non-small cell lung cancer), pancreatic cancer, and colon cancer.

In addition to the hematological malignancies and epithelial cancers noted above, the compounds of Formula 1 may also be used to treat other types of cancer, including leukemia (chronic myelogenous leukemia and chronic lymphocytic leukemia); breast cancer, genitourinary cancer, skin cancer, bone cancer, prostate cancer, and liver cancer; brain cancer; cancer of the larynx, gall bladder, rectum, parathyroid, thyroid, adrenal, neural tissue, bladder, head, neck, stomach, bronchi, and kidneys; basal cell carcinoma, squamous cell carcinoma, metastatic skin carcinoma, osteosarcoma, Ewing's sarcoma, veticulum cell sarcoma, and Kaposi's sarcoma; myeloma, giant cell tumor, islet cell tumor, acute and chronic lymphocytic and granulocytic tumors, hairy-cell tumor, adenoma, medullary carcinoma, pheochromocytoma, mucosal neuromas, intestinal ganglioneuromas, hyperplastic corneal nerve tumor, marfanoid habitus tumor, Wilms' tumor, seminoma, ovarian tumor, leiomyomatertumor, cervical dysplasia, neuroblastoma, retinoblastoma, myelodysplastic syndrome, rhabdomyosarcoma, astrocytoma, non-Hodgkin's lymphoma, malignant hypercalcemia, polycythermia vera, adenocarcinoma, glioblastoma multiforma, glioma, lymphomas, and malignant melanomas, among others.

In addition to cancer, the compounds of Formula 1 may also be used to treat other diseases, disorders or conditions related to abnormal cell growth, including non-malignant proliferative diseases such as benign prostatic hypertrophy, restinosis, hyperplasia, synovial proliferation disorder, idiopathic plasmacytic lymphadenopathy, retinopathy or other neovascular disorders of the eye, among others.

The compounds of Formula 1 may also be used to treat autoimmune diseases, disorders or conditions in addition to those listed above. Such diseases, disorders or conditions include Crohns disease, dermatomyositis, diabetes mellitus type 1, Goodpasture's syndrome, Graves' disease, Guillain-Barré syndrome, Hashimoto's disease, mixed connective tissue damage, myasthenia gravis, narcolepsy, pemphigus vulgaris, pernicious anemia, polymyositis, primary biliary cirrhosis, temporal arteritis, ulcerative colitis, vasculitis, and Wegener's granulomatosis, among others.

The compounds of Formula 1 may be used to treat inflammatory diseases, disorders or conditions including asthma, chronic inflammation, chronic prostatitis, glomerulonephritis, hypersensitivities, inflammatory bowel diseases (ulcerative colitis in addition to Crohn's disease), pelvic inflammatory disease, reperfusion injury, transplant rejection, vasculitis, and systemic inflammatory response syndrome.

The compounds of Formula 1 may also be used to treat specific diseases or conditions that may fall within one or more general disorders described above, including arthritis. In addition to rheumatoid arthritis, Sjögren's syndrome, systemic lupus erythematosus, SLE in children and adolescents, compounds of Formula 1 may also be used to treat other arthritis diseases, including ankylosing spondylitis, avascular necrosis, Behcet's disease, bursitis, calcium pyrophosphate dihydrate crystal deposition disease (pseudo gout), carpal tunnel syndrome, Ehlers-Danlos syndrome, fibromyalgia, Fifth disease, giant cell arteritis, gout, juvenile dermatomyositis, juvenile rheumatoid arthritis, juvenile spondyloarthopathy, Lyme disease, Marfan syndrome, myositis, osteoarthritis, osteogenesis imperfect, osteoporosis, Paget's disease, psoriatic arthritis, Raynaud's phenomenon, reactive arthritis, reflex sympathetic dystrophy syndrome, scleroderma, spinal stenosis, Still's disease, and tendinitis, among others.

The claimed and disclosed compounds may be combined with one or more other pharmacologically active compounds or therapies for the treatment of one or more diseases, disorders or conditions for which BTK is indicated, including those involving the immune system, inflammation, and abnormal cell growth. For example, compounds of Formula 1, which include compounds specifically named in the examples, and their pharmaceutically acceptable complexes, salts, solvates and hydrates, may be administered simultaneously, sequentially or separately in combination with one or more compounds or therapies for treating arthritis, including rheumatoid arthritis and osteoarthritis, or for treating cancer, including hematological malignancies, such as acute myeloid leukemia, B-cell chronic lymphocytic leukemia, B-cell lymphoma, T-cell lymphoma, multiple myeloma, and carcinomas, such as lung cancer, pancreatic cancer, and colon cancer. Such combinations may offer significant therapeutic advantages, including fewer side effects, improved ability to treat underserved patient populations, or synergistic activity.

For example, when used to treat arthritis, the compounds of Formula 1 may be combined with one or more nonsteroidal anti-inflammatory drugs (NSAIDs), analgesics, corticosteroids, biological response modifiers, and protein-A immunoadsorption therapy. Alternatively or additionally, when treating rheumatoid arthritis, the compounds of Formula 1 may be combined with one or more disease modifying antirheumatic drugs (DMARDs), and when treating osteoarthritis, the compounds of Formula 1 may be combined with one or more osteoporosis agents.

Representative NSAIDs include apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac. Representative analgesics include acetaminophen and morphine sulfate, as well as codeine, hydrocodone, oxycodone, propoxyphene, and tramadol, all with or without acetaminophen. Representative corticosteroids include betamethasone, cortisone acetate, dexamethasone, hydrocortisone, methylprednisolone, prednisolone, and prednisone. Representative biological response modifiers include TNF-α inhibitors, such as adalimumab, etanercept, and infliximab; selective B-cell inhibitors, such as rituximab; IL-1 inhibitors, such as anakinra, and selective costimulation modulators, such as abatacept.

Representative DMARDs include auranofin (oral gold), azathioprine, chlorambucil, cyclophosamide, cyclosporine, gold sodium thiomalate (injectable gold), hydroxychloroquine, leflunomide, methotrexate, minocycline, myophenolate mofetil, penicillamine, sulfasalazine, and JAK3 inhibitor (e.g., tofacitinib). Representative osteoporosis agents include bisphosphonates, such as alendronate, ibandronate, risedronate, and zoledronic acid; selective estrogen receptor modulators, such as droloxifene, lasofoxifene, and raloxifene; hormones, such as calcitonin, estrogens, and parathyroid hormone; and immunosuppressant agents such as azathioprine, cyclosporine, and rapamycin.

Particularly useful combinations for treating rheumatoid arthritis include a compound of Formula 1 and methotrexate; a compound of Formula 1 and one or more biological response modifiers, such as lefluonomide, etanercept, adalimumab, and infliximab; or a compound of Formula 1, methotrexate, and one or more biological response modifiers, such as lefluonomide, etanercept, adalimumab, and infliximab.

For the treatment of thrombis and restenosis, the compounds of Formula 1 may be combined with one or more cardiovascular agents such as calcium channel blockers, statins, fibrates, beta-blockers, ACE inhibitors, and platelet aggregation inhibitors.

The compounds of Formula 1 may also be combined with one or more compounds or therapies for treating cancer. These include chemotherapeutic agents (i.e., cytotoxic or antineoplastic agents) such as alkylating agents, antibiotics, antimetabolic agents, plant-derived agents, and topoisomerase inhibitors, as well as molecularly targeted drugs which block the growth and spread of cancer by interfering with specific molecules involved in tumor growth and progression. Molecularly targeted drugs include both small molecules and biologics.

Representative alkylating agents include bischloroethylamines (nitrogen mustards, e.g., chlorambucil, cyclophosphamide, ifosfamide, mechlorethamine, melphalan, and uracil mustard); aziridines (e.g., thiotepa); alkyl alkone sulfonates (e.g., busulfan); nitrosoureas (e.g., carmustine, lomustine, and streptozocin); nonclassical alkylating agents (e.g., altretamine, dacarbazine, and procarbazine); and platinum compounds (e.g., carboplatin, cisplatin, nedaplatin, oxaliplatin, satraplatin, and triplatin tetranitrate).

Representative antibiotic agents include anthracyclines (e.g., aclarubicin, amrubicin, daunorubicin, doxorubicin, epirubicin, idarubicin, pirarubicin, valrubicin, and zorubicin); anthracenediones (e.g., mitoxantrone and pixantrone); and streptomyces (e.g., actinomycin, bleomycin, dactinomycin, mitomycin C, and plicamycin).

Representative antimetabolic agents include dihydrofolate reductase inhibitors (e.g., aminopterin, methotrexate, and pemetrexed); hymidylate synthase inhibitors (e.g., raltitrexed and pemetrexed); folinic acid (e.g., leucovorin); adenosine deaminase inhibitors (e.g., pentostatin); halogenated/ribonucleotide reductase inhibitors (e.g., cladribine, clofarabine, and fludarabine); thiopurines (e.g., thioguanine and mercaptopurine); thymidylate synthase inhibitors (e.g., fluorouracil, capecitabine, tegafur, carmofur, and floxuridine); DNA polymerase inhibitors (e.g., cytarabine); ribonucleotide reductase inhibitors (e.g., gemcitabine); hypomethylating agent (e.g., azacitidine and decitabine); and ribonucleotide reductase inhibitor (e.g., hydroxyurea); and an asparagine depleter (e.g., asparaginase)

Representative plant-derived agents include vinca alkaloids (e.g., vincristine, vinblastine, vindesine, vinzolidine, and vinorelbine), podophyllotoxins (e.g., etoposide and teniposide), and taxanes (e.g., docetaxel, larotaxel, ortataxel, paclitaxel, and tesetaxel).

Representative type I topoisomerase inhibitors include camptothecins, such as belotecan, irinotecan, rubitecan, and topotecan. Representative type II topoisomerase inhibitors include amsacrine, etoposide, etoposide phosphate, and teniposide, which are derivatives of epipodophyllotoxins.

Molecularly targeted therapies include biologic agents such as cytokines and other immune-regulating agents. Useful cytokines include interleukin-2 (IL-2, aldesleukin), interleukin 4 (IL-4), interleukin 12 (IL-12), and interferon, which includes more than 23 related subtypes. Other cytokines include granulocyte colony stimulating factor (CSF) (e.g., filgrastim) and granulocyte macrophage colony stimulating factor (GM-CSF or CSF2) (e.g., sargramostim, namimulab). Other immuno-modulating agents include bacillus Calmette-Guerin, levamisole, and octreotide; monoclonal antibodies against tumor antigens, such as trastuzumab and rituximab; and cancer vaccines, which induce an immune response to tumors.

In addition, molecularly targeted drugs that interfere with specific molecules involved in tumor growth and progression include inhibitors of epidermal growth factor (EGF), transforming growth factor-alpha (TGF$_\alpha$), TGF$_\beta$, heregulin, insulin-like growth factor (IGF), fibroblast growth factor (FGF), keratinocyte growth factor (KGF), colony stimulating factor (CSF), erythropoietin (EPO), interleukin-2 (IL-2), nerve growth factor (NGF), platelet-derived growth factor (PDGF), hepatocyte growth factor (HGF), vascular endothelial growth factor (VEGF), angiopoietin, epidermal growth factor receptor (EGFR), human epidermal growth factor receptor 2 (HER2), HER4, insulin-like growth factor 1 receptor (IGF1R), IGF2R, fibroblast growth factor 1 receptor (FGF1R), FGF2R, FGF3R, FGF4R, vascular endothelial growth factor receptor (VEGFR), tyrosine kinase with immunoglobulin-like and epidermal growth factor-like domains 2 (Tie-2), platelet-derived growth factor receptor (PDGFR), Abl, Bcr-Abl, Raf, FMS-like tyrosine kinase 3 (FLT3), c-Kit, Src, protein kinase c (PKC), tropomyosin receptor kinase (Trk), Ret, mammalian target of rapamycin (mTOR), Aurora kinase, polo-like kinase (PLK), mitogen activated protein kinase (MAPK), mesenchymal-epithelial transition factor (c-MET), cyclin-dependant kinase (CDK), Akt, extracellular signal-regulated kinases (ERK), poly (ADP) ribose polymerase (PARP), and the like.

Specific molecularly targeted drugs include selective estrogen receptor modulators, such as tamoxifen, toremifene, fulvestrant, and raloxifene; antiandrogens, such as bicalutamide, nilutamide, megestrol, and flutamide; and aromatase inhibitors, such as exemestane, anastrozole, and letrozole. Other specific molecularly targeted drugs include agents which inhibit signal transduction, such as imatinib, dasatinib, nilotinib, trastuzumab, gefitinib, erlotinib, cetuximab, lapatinib, panitumumab, and temsirolimus; agents that induce apoptosis, such as bortezomib; agents that block angiogenesis, such as bevacizumab, sorafenib, and sunitinib; agents that help the immune system destroy cancel cells, such as rituximab and alemtuzumab; and monoclonal antibodies which deliver toxic molecules to cancer cells, such as gemtuzumab ozogamicin, tositumomab, 131I-tositumoab, and ibritumomab tiuxetan.

Biological Activity

The activity of compounds as BTK inhibitors may be determined by a variety of methods, including in vitro and in vivo methods. The following in vitro assay measures a test compound's ability to inhibit BTK-mediated phosphorylation of a FAM-labeled substrate, 5-FAM-EEPLYWSF-PAKKK-NH$_2$.

Purified BTK may be obtained as follows (Clone SBVC-1603_9P is used). A cDNA sequence encoding residues 382 to 659 of human BTK is cloned into the vector pSXB4. This construct engineers an in-frame translational fusion with the Glutathione-S-Transferase (GST) protein for use in affinity purification. The fusion protein derived from this construct contains a protease recognition sequence to liberate the BTK from the GST affinity tag. High-titer baculoviral stocks, generated using the Bac-to-Bac® system (Invitrogen), are used to express the recombinant protein in *Spodoptera frugiperda* Sf9 cells in 10 L Wave bags. Recombinant proteins are isolated from cellular extracts by passage over Glutathione Sepharose 4B (GE Healthcare) and the BTK moiety is released from the GST affinity tag by treatment with PreScission protease. The BTK recombinant protein is further purified by size exclusion chromatography (HiLoad 16/60 Superdex 200, GE Healthcare) in a buffer containing 20 mM Hepes (pH 7.4), 50 mM NaCl, 10 mM MgCl$_2$, 0.25 mM TCEP and 0.1 mM EDTA. The purity of the fractions is assessed by SDS PAGE and the peak protein fractions are pooled and concentrated using Amicon Ultra-15 Centrifugal Filter Devices (Millipore).

The inhibitory properties of compounds relative to BTK is determined using a black 384-well-plate format in a buffer which contains 50 mM Hepes, 10 mM NaCl, 10 mM MgCl$_2$, 0.2 mM EDTA, 0.01% Brij35®, 1 mM DTT, and 0.1 mg/mL BSA at pH 7.3. The test compound is prepared in DMSO using 2-fold serial dilutions for 11 data points, which are added to the buffer so that each dilution contains 3% DMSO. To initiate the assay, 5 µL of 3 µM 5FAM-EEPLYWSF-PAKKK-NH$_2$ (in buffer), 5 µL of diluted test compound (3% DMSO in buffer), and 5 µL of 9 nM BTK and 150 µM ATP in buffer are combined in each well. The reaction mixtures are incubated at room temperature for 60 minutes and then quenched by adding 25 µL of 50 mM EDTA. To quantify the fluorescent-labeled substrate and product following reaction, the test plate is loaded on a Caliper LC-3000, which measures percent of conversion by microfluidic-based separation. Corresponding IC$_{50}$ values are calculated by non-linear curve fitting of the compound concentrations and percent of inhibition to the standard IC$_{50}$ equation and reported as pIC$_{50}$, i.e., $-\log(\text{IC}_{50})$, where IC$_{50}$ is molar concentration at 50% inhibition.

EXAMPLES

The following examples are intended to be illustrative and non-limiting, and represent specific embodiments of the present invention.

$^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: CDCl₃ (deuterochloroform), DMSO-d₆ (deuterodimethylsulfoxide), CD₃OD (deuteromethanol), CD₃CN (deuteroacetonitrile), and THF-d₈ (deuterotetrahydrofuran). The mass spectra (M+H) were recorded using either electrospray ionization (ESI-MS) or atmospheric pressure chemical ionization (APCI-MS).

Where indicated, products of certain preparations and examples are purified by mass-triggered HPLC (Pump: Waters™ 2525; MS: ZQ™; Software: MassLynx™), flash chromatography or preparative thin layer chromatography (TLC). Reverse phase chromatography is typically carried out on a column (e.g., Gemini™ 5 μm C18 110 Å, Axia™, 30×75 mm, 5 μm) under acidic conditions ("acid mode") eluting with ACN and water mobile phases containing 0.035% and 0.05% trifluoroacetic acid (TFA), respectively, or under basic conditions ("basic mode") eluting with water and 20/80 (v/v) water/acetonitrile mobile phases, both containing 10 mM NH₄HCO₃. Preparative TLC is typically carried out on silica gel 60 F₂₅₄ plates. After isolation by chromatography, the solvent is removed and the product is obtained by drying in a centrifugal evaporator (e.g., GeneVac™), rotary evaporator, evacuated flask, etc. Reactions in an inert (e.g., nitrogen) or reactive (e.g., H₂) atmosphere are typically carried out at a pressure of about 1 atmosphere (14.7 psi).

PREPARATION x1

(R)-3-(1-(pyrrolidin-3-yloxy)isoquinolin-3-yl)-1H-1,2,4-triazol-5(4H)-one

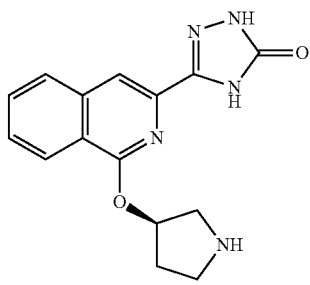 [SMILES: O=c1[nH]nc(-c2cc3ccccc3c(O[C@@H]3CCNC3)n2)[nH]1]

STEP A: (R)-tert-butyl 3-((3-cyanoisoquinolin-1-yl)oxy)pyrrolidine-1-carboxylate

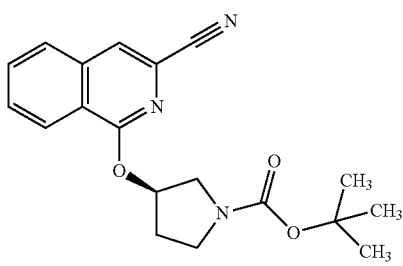 [SMILES: CC(C)(C)OC(=O)N1CC[C@@H](Oc2nc(C#N)cc3ccccc23)C1]

A mixture of (R)-tert-butyl 3-hydroxypyrrolidine-1-carboxylate (496 mg, 2.65 mmol) in NMP (4 mL) at 0° C. was treated with NaH (106 mg, 2.65 mmol) and stirred for 1 hour. Next, 1-chloroisoquinoline-3-carbonitrile (500 mg, 2.65 mmol) was added and the reaction mixture was stirred at RT for 15 minutes and then heated at 140° C. for 15 minutes in a microwave reactor. The crude reaction mixture, which contained the title compound, was used directly in the next step.

STEP B: (R)-tert-butyl 3-((3-(5-oxo-4,5-dihydro-1H-1,2,4-triazol-3-yl)isoquinolin-1-yl)oxy)pyrrolidine-1-carboxylate

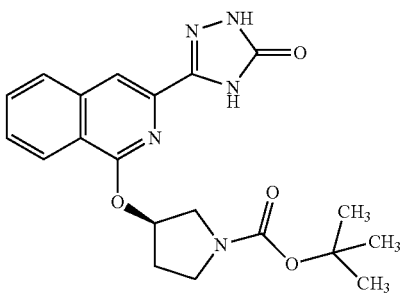 [SMILES: CC(C)(C)OC(=O)N1CC[C@@H](Oc2nc(-c3n[nH]c(=O)[nH]3)cc3ccccc23)C1]

To crude (R)-tert-butyl 3-((3-cyanoisoquinolin-1-yl)oxy)pyrrolidine-1-carboxylate was added ethyl hydrazinecarboxylate (1.104 g, 10.60 mmol). The reaction mixture was heated at 175° C. overnight and was subsequently cooled and diluted with EtOAc. The organic phase was washed with brine, dried over Na₂SO₄, and concentrated to give the title compound, which was used directly in the next step.

STEP C: (R)-3-(1-(pyrrolidin-3-yloxy)isoquinolin-3-yl)-1H-1,2,4-triazol-5(4H)-one To crude (R)-tert-butyl 3-((3-(5-oxo-4,5-dihydro-1H-1,2,4-triazol-3-yl)isoquinolin-1-yl)oxy)pyrrolidine-1-carboxylate was added a minimal amount of NMP and TFA (2 mL). The solution was stirred at RT for 10 minutes and concentrated. The crude product was purified by preparative HPLC eluting with a gradient of 15-22% ACN in water (acid mode) to give the title compound (229 mg, 29% over 3 steps).

PREPARATION x2

(S)-tert-butyl 3-((3-cyanoisoquinolin-1-yl)amino)pyrrolidine-1-carboxylate

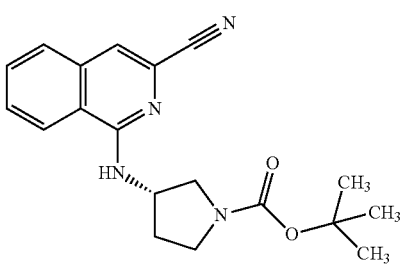

A mixture of (S)-tert-butyl 3-aminopyrrolidine-1-carboxylate (434 mg, 2.333 mmol) in NMP (2.5 mL) at 0° C. was treated with NaH (93 mg, 2.333 mmol) and stirred for 1 hour. Next, 1-chloroisoquinoline-3-carbonitrile (400 mg, 2.121 mmol) was added and the reaction mixture was stirred at RT for 15 minutes and then heated at 140° C. for 15 minutes in a microwave reactor. The crude reaction mixture, which contained the title compound, was used without further purification. ESI-MS m/z [M+H]+ 339.4.

PREPARATION x3

(S)-3-(1-(pyrrolidin-3-ylamino)isoquinolin-3-yl)-1H-1,2,4-triazol-5(4H)-one

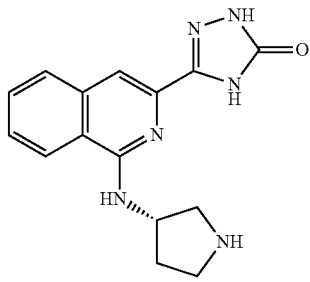 [SMILES: O=c1[nH]nc(-c2cc3ccccc3c(N[C@H]3CCNC3)n2)[nH]1]

STEP A: (S)-tert-butyl 3-((3-(5-oxo-4,5-dihydro-1H-1,2,4-triazol-3-yl)isoquinolin-1-yl)amino)pyrrolidine-1-carboxylate

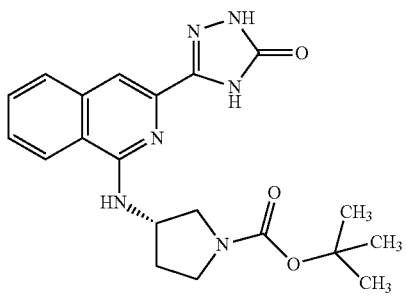 [SMILES: CC(C)(C)OC(=O)N1CC[C@H](Nc2nc(-c3n[nH]c(=O)[nH]3)cc3ccccc23)C1]

To a crude reaction mixture containing (S)-tert-butyl 3-((3-cyanoisoquinolin-1-yl)amino)pyrrolidine-1-carboxylate (717 mg) was added NMP (2 mL) and ethyl hydrazinecarboxylate (883 mg, 8.484 mmol). The reaction mixture was heated at 175° C. overnight and was subsequently cooled, diluted with EtOAc, and washed with aqueous NH4Cl. The organic layer was separated and concentrated to give the title compound, which was used directly in the next step.

STEP B: (S)-3-(1-(pyrrolidin-3-ylamino)isoquinolin-3-yl)-1H-1,2,4-triazol-5(4H)-one To crude (S)-tert-butyl 3-((3-(5-oxo-4,5-dihydro-1H-1,2,4-triazol-3-yl)isoquinolin-1-yl)amino)pyrrolidine-1-carboxylate was added DCM (3 mL) and TFA (1 mL). The mixture was stirred for 1 hour and concentrated. The crude product was purified by preparative HPLC eluting with a gradient of 5-30% ACN in water (acid mode) to give the title compound (8 mg).

PREPARATION x4

1-(bromomethyl)isoquinoline-3-carbonitrile

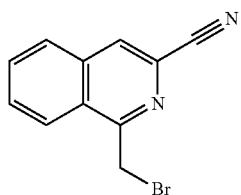 [SMILES: N#Cc1cc2ccccc2c(CBr)n1]

STEP A: Methyl isoquinoline-1-carboxylate

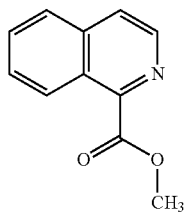

To a solution of isoquinoline-1-carboxylic acid (10 g, 57.74 mmol) in MeOH (150 mL) was added concentrated sulfuric acid (15 mL) at 0° C. The mixture was warmed to 65° C. and stirred at 65° C. for 24 hours. After cooling to RT, the reaction mixture was partitioned between DCM and saturated aqueous NaHCO3. The organic layer was separated and dried over Na2SO4, and the solvent was evaporated under reduced pressure to give the title compound as a yellow oil (11.2 g, 100%). ESI-MS m/z [M+H]+ 188.

STEP B: 1-(methoxycarbonyl)isoquinoline 2-oxide

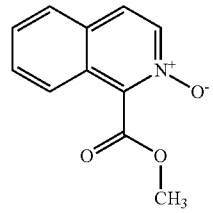

To a suspension of methyl isoquinoline-1-carboxylate (11.2 g, 59.8 mmol) in DCM (150 mL) was added 3-chloroperoxybenzoic acid (15.5 g, 89.7 mmol) at 0° C. The mixture was warmed to RT and was stirred at RT for 24 hours. The reaction was quenched with saturated aqueous NaHCO3 and the mixture was extracted with DCM. The organic layer was separated and dried over Na2SO4, and the solvent was evaporated under reduced pressure. The crude product was purified by silica gel chromatography eluting with petroleum ether and EtOAc (1:1) to give the title compound as a white solid (9.5 g, 78%). ESI-MS m/z [M+H]+ 204.

STEP C: Methyl 3-chloroisoquinoline-1-carboxylate

A mixture of 1-(methoxycarbonyl)isoquinoline 2-oxide (9.5 g, 46.75 mmol) and POCl$_3$ (50 mL) was heated at 100° C. for 4 hours. The reaction mixture was subsequently cooled and concentrated, and the crude product was purified by silica gel chromatography eluting with petroleum ether and EtOAc (15:1) to give the title compound as a white solid (5.1 g, 49%). ESI-MS m/z [M+H]$^+$ 222.

STEP D: (3-chloroisoquinolin-1-yl)methanol

To a solution of methyl 3-chloroisoquinoline-1-carboxylate (5.1 g, 23.0 mmol) in MeOH (50 mL) was added NaBH$_4$ (2.17 g, 57.5 mmol). The reaction mixture was stirred at RT for 2 hours. The reaction was quenched with saturated aqueous NH$_4$Cl and the mixture was extracted with EtOAc. The organic layer was separated and dried over Na$_2$SO$_4$, and the solvent was evaporated under reduced pressure to give the title compound as a yellow solid (3.94 g, 88%). ESI-MS m/z [M+H]$^+$ 194.

STEP E:
1-(hydroxymethyl)isoquinoline-3-carbonitrile

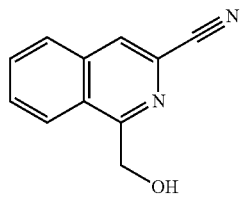 [SMILES: N#Cc1cc2ccccc2c(CO)n1]

A suspension of (3-chloroisoquinolin-1-yl)methanol (1.0 g, 5.17 mmol), zinc cyanide (672 mg, 5.68 mmol), Pd$_2$(dba)$_3$ (190 mg, 0.21 mmol), XPhos (241 mg, 0.52 mmol) in DMF (15 mL) was heated at 150° C. for 1 hour under a nitrogen atmosphere in a microwave reactor. The reaction mixture was subsequently diluted with water and extracted with EtOAc. The organic layer was separated and dried over Na$_2$SO$_4$, and the solvent was evaporated under reduced pressure. The crude product was purified by silica gel chromatography eluting with petroleum ether and EtOAc (4:1) to give the title compound as a yellow solid (330 mg, 34%). ESI-MS m/z [M+H]$^+$ 185.1.

STEP F:
1-(bromomethyl)isoquinoline-3-carbonitrile

A suspension of 1-(hydroxymethyl)isoquinoline-3-carbonitrile (0.150 g, 0.814 mmol) in THF (0.8 mL) and treated with PBr$_3$ (0.814 mL, 0.814 mmol). The reaction mixture was stirred at RT for 2 hours, then poured over ice and neutralized with saturated aqueous NaHCO$_3$. The mixture was warmed to RT and extracted with EtOAc (20 mL). The organic phase was separated, dried over MgSO$_4$, filtered, and concentrated in vacuo to give the title compound as a yellow solid. The crude product was dried under high vacuum and used without further purification (0.15 g, 75%). ESI-MS m/z [M+H]$^+$ 247.5.

PREPARATION x5

1-chloro-8-fluoroisoquinoline-3-carbonitrile

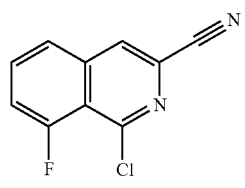 [SMILES: N#Cc1cc2cccc(F)c2c(Cl)n1]

STEP A: methyl 2-bromo-6-fluorobenzoate

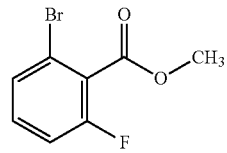

To a solution 2-bromo-6-fluorobenzoic acid (50 g, 0.229 mol) and potassium carbonate (31.6 g, 0.229 mol) in N,N-dimethylformamide (250 mL) was added dropwise methyl iodide (51.83 g, 0.365 mol) over a 30 minute period. The reaction mixture was stirred at RT for 3.5 hours. The resulting mixture was diluted with water (500 mL) and extracted with EtOAc (3×300 mL). The combined organic layers were washed with 1M aqueous HCl (100 mL), dried over anhydrous Na$_2$SO$_4$, filtered, and concentrated under reduced pressure to give the title compound (53 g, 99.7%).

STEP B: methyl 2-fluoro-6-vinylbenzoate

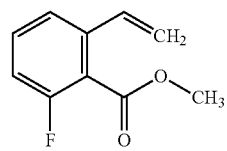

To a solution of methyl 2-bromo-6-fluorobenzoate (53 g, 0.228 mol) and potassium trifluoro(vinyl)borate (33.63 g, 0.251 mol) in dioxane and H$_2$O (3:1, 600 mL) was added Pd(dppf)Cl$_2$ (5 g, 6.84 mmol) and sodium carbonate (69 g, 0.684 mol) at RT. The reaction mixture was heated at 100° C. for 12 hours under a nitrogen atmosphere. The mixture was concentrated in vacuo, diluted with water, and extracted with EtOAc (3×200 mL). The combined organic layers were washed with brine, dried over anhydrous Na$_2$CO$_3$, filtered, and concentrated. The crude product was purified by column chromatography eluting with a gradient of EtOAc (1-100%) and PE to give the title compound (31.4 g, 76.5%). $^1$H NMR (400 MHz, CDCl$_3$) δ ppm 7.45-7.36 (m, 2H), 7.03-7.02 (m, 1H), 6.88-6.81 (m, 1H), 5.77-5.73 (m, 1H), 5.41-5.39 (d, J=10.8 Hz, 1H), 3.95 (s, 3H).

STEP C: methyl 2-fluoro-6-formylbenzoate

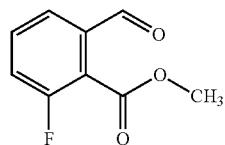

Into a solution of methyl 2-fluoro-6-vinylbenzoate (31 g, 0.172 mol) in dry dichloromethane (300 mL) was bubbled O$_3$ at −78° C. over a 30 minute period. Next, nitrogen gas was bubbled into the solution until it turned colorless. Dimethylsulfane (84.13 g, 1.36 mol) was added dropwise to the solution, which was subsequently warmed to RT and stirred for 2 hours. The mixture was then washed with water (30 mL) and extracted with DCM (3×300 mL). The combined organic layers were dried over Na$_2$SO$_4$ and concentrated. The crude product was purified by column chromatography eluting with a gradient of EtOAc (10-100%) and PE to give the title compound (21 g, 67%). $^1$H NMR (400 MHz, CDCl$_3$) δ ppm 10.01 (s, 1H), 7.65-7.63 (d, J=7.6 Hz, 1H), 7.56-7.53 (dd, J$_1$=5.2 Hz, J$_2$=8.0 Hz, 1H), 7.35-7.30 (t, J=8.4 Hz, 1H), 3.94 (s, 3H).

STEP D: (Z)-methyl 2-fluoro-6-((5-oxo-2-phenyloxazol-4(5H)-ylidene)methyl) benzoate

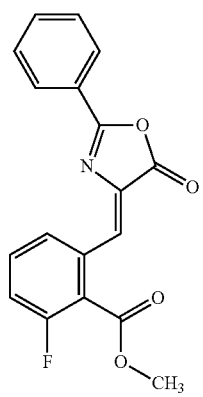 [SMILES: COC(=O)c1c(F)cccc1/C=C1\N=C(c2ccccc2)OC1=O]

This step was performed in five separate batches. For each batch, a solution of methyl 2-fluoro-6-formylbenzoate (3 g, 16.5 mmol), 2-benzamidoacetic acid (3.6, 20 mmol) and sodium acetate (1.62 g, 19.7 mmol) in acetic anhydride (30 mL) was heated at 100° C. in a microwave reactor (100 W, 150 psi) under nitrogen atmosphere for 2 hours. The reaction mixtures were diluted with EtOAc (100 mL) and washed with saturated aqueous Na$_2$CO$_3$. The combined organic layers were concentrated in vacuo to give the title compound as a brown solid, which was used without further purification (15 g). ESI-MS m/z [M+H]$^+$ 326.2.

STEP E: methyl 8-fluoro-1-oxo-1,2-dihydroisoquinoline-3-carboxylate

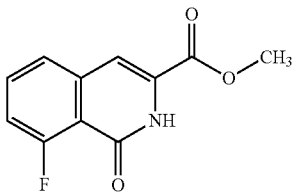 [SMILES: COC(=O)c1cc2cccc(F)c2c(=O)[nH]1]

A solution of crude (Z)-methyl 2-fluoro-6-((5-oxo-2-phenyloxazol-4(5H)-ylidene)methyl) benzoate (15 g) and potassium hydroxide (2.58 g, 46 mmol) in acetic anhydride (150 mL) was heated at 100° C. for 2 hours. The solvent was removed in vacuo, and the residue was diluted with water (30 mL). The resulting mixture was neutralized with 1M aqueous HCl (100 mL) and filtered. The solids were dried in vacuo to give 8-fluoro-1-oxo-1,2-dihydroisoquinoline-3-carboxylic acid (4 g, ESI-MS m/z [M+H]$^+$ 208.0) which was converted to the methyl ester as described, below. The filtrate was concentrated under reduced pressure to give crude product which was purified by column chromatography eluting with a gradient of EtOAc (30-100%) and PE to give a first batch of the title compound (2 g, 19.6%). ESI-MS m/z [M+H]$^+$ =222.1.

To a solution of 8-fluoro-1-oxo-1,2-dihydroisoquinoline-3-carboxylic acid (4 g, 19.3 mmol) in MeOH (100 mL) was added SOCl$_2$ (20 mL) at 0° C. The reaction mixture was stirred at RT for 30 minutes and then heated to reflux for 5 hours. The reaction mixture was subsequently concentrated in vacuo. The crude product was purified by column chromatography eluting with petroleum ether and ethyl acetate (PE/EtOAc=1:1-1:2 gradient) to give a second batch of the title compound (3 g, 80%). $^1$H NMR (400 MHz, DMSO-d$_6$) δ ppm 11.19 (s, 1H), 7.79-7.71 (m, 2H), 7.42-7.38 (m, 2H), 3.89 (s, 3H).

STEP F: 8-fluoro-1-oxo-1,2-dihydroisoquinoline-3-carboxamide

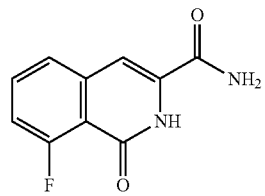 [SMILES: NC(=O)c1cc2cccc(F)c2c(=O)[nH]1]

To a vessel containing NH$_3$/MeOH (140 mL) was added methyl 8-fluoro-1-oxo-1,2-dihydroisoquinoline-3-carboxylate (5 g, 15 mmol). The vessel was sealed and the solution was stirred at RT for 30 minutes and then heated to reflux for 2 hours. The reaction mixture was concentrated in vacuo to give the title compound, which was used without further purification (5 g, 85%). $^1$H NMR (400 MHz, DMSO-$d_6$) δ ppm 10.26 (s, 1H), 8.32 (s, 1H), 7.92 (s, 1H), 7.82-7.81 (m, 1H), 7.61-7.59 (d, J=8.0 Hz, 1H), 7.41-7.35 (m, 1H).

STEP G:
1-chloro-8-fluoroisoquinoline-3-carbonitrile

A solution of 8-fluoro-1-oxo-1,2-dihydroisoquinoline-3-carboxamide (5 g, 5.5 mmol) in POCl$_3$(46.23 g) was heated to reflux for 4 hours and was subsequently concentrated in vacuo. The crude product was purified by column chromatography eluting with petroleum ether and ethyl acetate (PE/EtOAc=5:1-2:1 gradient) to give the title compound (3.2 g, 35%). ESI-MS m/z [M+H]$^+$ 207.1.

PREPARATION x6

1,7-dichloroisoquinoline-3-carbonitrile

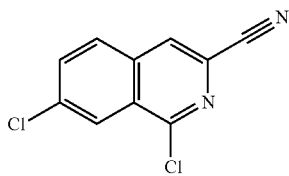 [SMILES: N#Cc1cc2ccc(Cl)cc2c(Cl)n1]

STEP A: methyl 5-chloro-2-vinylbenzoate

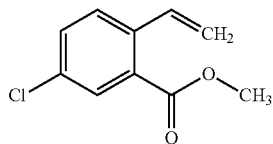

A stirred suspension of methyl 2-bromo-5-chlorobenzoate (10 g, 40.08 mmol), potassium trifluoro(vinyl)borate (8.05 g, 60.12 mmol), Pd(dppf)Cl$_2$ (1.64 g, 2.0 mmol) and sodium carbonate (8.5 g, 80.16 mmol) in dioxane (150 mL) and water (15 mL) was refluxed for 8 hours under a nitrogen atmosphere. After cooling to RT, the mixture was filtered, concentrated, and the crude product was purified by column chromatography eluting with petroleum ether and ethyl acetate (PE/EtOAc=100:1-50:1 gradient) to give the title compound (31.4 g, 76.4%). $^1$H NMR (400 MHz, CDCl$_3$) δ ppm 7.80 (d, J=2.0 Hz, 1H), 7.45 (d, J=8.0 Hz, 1H), 7.31-7.39 (m, 2H), 5.57 (d, J=17.6 Hz, 1H), 5.31 (d, J=10.8 Hz, 1H), 3.83 (s, 3H).

STEP B: methyl 5-chloro-2-formylbenzoate

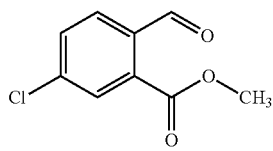

Into a solution of methyl 5-chloro-2-vinylbenzoate (16.3 g, 82.89 mmol) in dry DCM (250 mL) was bubbled O$_3$ at −78° C. over a 30 minute period. Next, nitrogen gas was bubbled into the solution until it turned colorless. Dimethylsulfane (10.3 g, 165.79 mmol) was added dropwise. The resulting mixture was warmed to RT, stirred for 2 hours, and concentrated. The crude product was purified by silica gel column chromatography eluting with petroleum ether and ethyl acetate (PE/EtOAc=40:1) to give the title compound as a white solid (10 g, 60%). $^1$H NMR (400 MHz, CDCl$_3$) δ ppm 10.52 (s, 1H), 7.89 (d, J=2.0 Hz, 1H), 7.84 (d, J=8.0 Hz, 1H), 7.55 (dd, J=8.0 Hz and 2.0 Hz, 1H), 3.93 (s, 3H).

STEP C: ethyl 7-chloro-1-oxo-1,2-dihydroisoquinoline-3-carboxylate

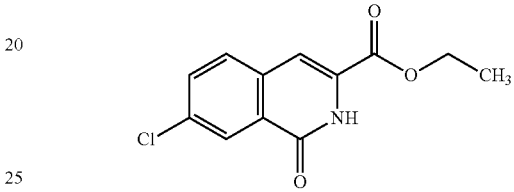

To a stirred mixture of NaH (1.81 g, 30.3 mmol) in DMF (20 mL) was added a solution of methyl 5-chloro-2-formylbenzoate (5.0 g, 25 mmol) and ethyl 2-isocyanoacetate (2.85 g, 25 mmol) in DMF (60 mL) at 40° C. over a 20 minute period. The reaction mixture was stirred at 20° C. for 2 hours. Its pH was adjusted to 7.0 with acetic acid (10%) and the mixture was extracted with DCM (3×200 mL). The organic layers were combined, washed with brine (200 mL), dried over Na$_2$SO$_4$, and concentrated. The crude product was purified by silica gel column chromatography eluting with petroleum ether and ethyl acetate (PE/EtOAc=15:1-5:1 gradient) to give the title compound (2.0 g, 31%). ESI-MS m/z [M+H]$^+$ 252.1.

STEP D: 7-chloro-1-oxo-1,2-dihydroisoquinoline-3-carboxamide

Ethyl 7-chloro-1-oxo-1,2-dihydroisoquinoline-3-carboxylate (580 mg, 2.30 mmol) was dissolved in NH$_3$/MeOH (4.0M, 15 mL) and the reaction mixture was stirred at RT overnight. The solvent was removed in vacuo. The resulting residue was washed with petroleum ether and dried to give the title compound (200 mg, 38%). ESI-MS m/z [M+H]$^+$ 223.1.

STEP E: 1,7-dichloroisoquinoline-3-carbonitrile

A solution of 7-chloro-1-oxo-1,2-dihydroisoquinoline-3-carboxamide (550 mg, 2.46 mmol) in POCl$_3$(10 mL) was heated to reflux for 6 hours. The solvent was subsequently removed in vacuo and the crude product was purified by column chromatography eluting with petroleum ether and ethyl acetate (PE/EA=30:1) to give the title compound (450 mg, 81.8%). $^1$H NMR (400 MHz, CDCl$_3$) δ ppm 8.35 (d, J=1.6 Hz, 1H), 8.02 (s, 1H), 7.85 (d, J=8.0 Hz, 1H), 7.80 (dd, J=1.6 Hz and 8.0 Hz, 1H).

PREPARATION x7

1,8-dichloroisoquinoline-3-carbonitrile

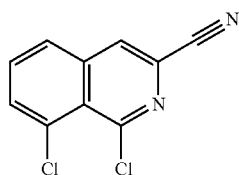 [SMILES: N#Cc1cc2cccc(Cl)c2c(Cl)n1]

STEP A: methyl 2-bromo-6-chlorobenzoate

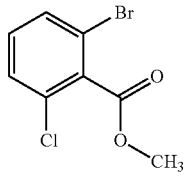

To a solution 2-bromo-6-chlorobenzoic acid (9.5 g, 0.041 mol) and potassium carbonate (8.6 g, 0.061 mol) in N,N-dimethylformamide (50 mL) was added methyl iodide (11.2 g, 0.081 mol) dropwise over a 10 minute period. The reaction mixture was stirred at RT for 3.5 hours and was subsequently diluted with water (500 mL). The aqueous phase was back-extracted with EtOAc (3×300 mL). The organic layers were combined, washed with 1M HCl aq (100 mL), dried over anhydrous Na$_2$SO$_4$, filtered, and concentrated under reduced pressure to give the title compound (10.0 g, 99.4%). $^1$H NMR (400 MHz, CDCl$_3$) δ ppm 7.413 (d, J=8 Hz, 1H), 7.29 (d, J=8 Hz, 1H), 7.137 (t, J=8 Hz, 1H), 3.9 (s, 3H).

STEP B: methyl 2-chloro-6-vinylbenzoate

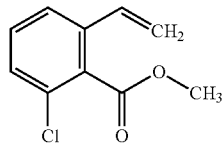

To a solution of methyl 2-bromo-6-chlorobenzoate (7.5 g, 0.03 mol) and potassium trifluoro(vinyl)borate (6.07 g, 0.045 mol) in dioxane and H$_2$O (10:1, 100 mL) was added Pd(dppf)Cl$_2$ (739 mg, 0.906 mmol), and sodium carbonate (6.4 g, 0.06 mol) at RT. The reaction mixture was heated at 100° C. for 12 hours under a nitrogen atmosphere. The mixture was subsequently concentrated in vacuo and diluted with water. The aqueous phase was extracted with EtOAc (3×100 mL). The organic layers were combined, washed with brine, dried over anhydrous Na$_2$CO$_3$, filtered, and concentrated. The crude product was purified by column chromatography eluting with a gradient of EtOAc (0-90%) and PE to give the title compound (6.7 g, 85%). $^1$H NMR (400 MHz, CDCl$_3$) δ ppm 7.39-7.41 (m, 1H), 7.22-7.26 (m, 2H), 6.55-6.62 (m, 1H), 5.68 (d, J=17.2 Hz, 1H), 5.31 (d, J=11.2 Hz, 1H).

STEP C: methyl 2-chloro-6-formylbenzoate

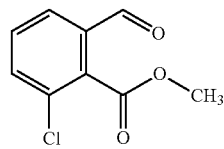

Into a solution of methyl 2-chloro-6-vinylbenzoate (6.7 g, 34 mmol) in dry DCM (100 mL) was bubbled O$_3$ at −78° C. over a 30 minute period. Next, nitrogen gas was bubbled into the solution until the solution was colorless. Dimethylsulfane (4.3 g, 68 mmol) was added dropwise and the resulting mixture was warmed to RT and stirred for 2 hours. The reaction mixture was subsequently washed with water (30 mL) and extracted with DCM (3×100 mL). The organic layers were combined, dried over Na$_2$SO$_4$, and concentrated. The crude product was purified by column chromatography eluting with a gradient of EtOAc (0-90%) and PE to give the title compound (3.8 g, 56%). $^1$H NMR (400 MHz, CDCl$_3$) δ ppm 9.89 (s, 1H), 7.728 (d, J=7.2 Hz, 1H), 7.606 (d, J=8.0 Hz, 1H), 7.489 (t, J=8.0 Hz, 1H), 3.95 (s, 3H).

STEP D: ethyl 8-chloro-1-oxo-1,2-dihydroisoquinoline-3-carboxylate

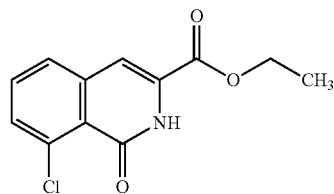 [SMILES: CCOC(=O)c1cc2cccc(Cl)c2c(=O)[nH]1]

To a solution of NaH (652.8 mg, 16.32 mmol) in DMF (20 mL) was added methyl 2-chloro-6-formylbenzoate (2.7 g, 13.6 mmol) and ethyl 2-isocyanoacetate (1.55 g, 13.6 mmol) in DMF (5 mL) at 40° C. over a 20 minute period. The reaction mixture was stirred at 20° C. for an additional 30 minutes. The reaction mixture was subsequently diluted with EtOAc (100 mL) and washed with saturated aqueous Na$_2$CO$_3$. The organic phase was concentrated in vacuo. The crude product was purified by column chromatography eluting with a gradient of EtOAc (0-90%) and PE to give the title compound (0.5 g, 15.6%). ESI-MS m/z [M+H]$^+$ 252.1.

STEP E: 8-chloro-1-oxo-1,2-dihydroisoquinoline-3-carboxamide

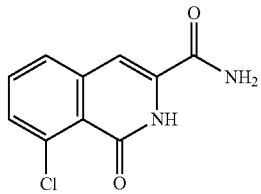

To a vessel containing NH₃/MeOH (10 mL) was added ethyl 8-chloro-1-oxo-1,2-dihydroisoquinoline-3-carboxylate (500 mg, 1.99 mmol). The vessel was sealed and the resulting solution was stirred at RT for 1 hour. The reaction mixture was subsequently concentrated in vacuo to give the title compound, which was used without further purification (0.5 g, 98%). ESI-MS m/z [M+H]⁺ 223.1.

STEP F: 1,8-dichloroisoquinoline-3-carbonitrile

A solution of 8-chloro-1-oxo-1,2-dihydroisoquinoline-3-carboxamide (0.5 g, 1.99 mmol) in POCl₃ (10 mL) was heated to reflux for 4 hours. The reaction mixture was subsequently concentrated in vacuo and the crude product was purified by column chromatography eluting with petroleum ether and ethyl acetate (PE/EtOAc=5:1-2:1 gradient) to give the title compound (200 mg, 40%). ESI-MS m/z [M+H]⁺ 223.1.

PREPARATION x8

1-chloro-8-methoxyisoquinoline-3-carbonitrile

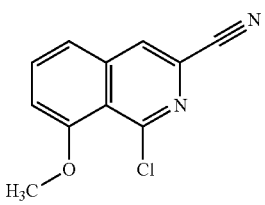

STEP A: methyl 2-bromo-6-methoxybenzoate

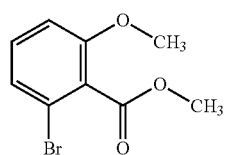

To a mixture of 2-bromo-6-methoxybenzoic acid (40 g, 0.176 mol) in DMF (300 mL) was added K₂CO₃ (24.8 g, 0.176 mol) and CH₃I (37 g, 0.264 mol). The mixture was stirred at RT overnight. The reaction was quenched with 1M HCl aq and the mixture was extracted with EtOAc (3×300 mL). The organic phase was dried over MgSO₄ and concentrated in vacuo to give the title compound (41 g, 99%).

STEP B: methyl 2-methoxy-6-vinylbenzoate

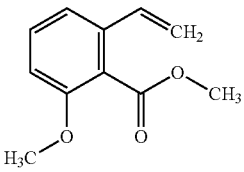

To a mixture of methyl 2-bromo-6-methoxybenzoate (30 g, 0.12 mol) and potassium trifluoro(vinyl)borate (18 g, 0.13 mol) in dioxane and H₂O (5:1, 360 mL) was added Pd(dppf)Cl₂ (2.63 g, 0.0036 mol) and Na₂CO₃ (25.4 g, 0.24 mol) at RT. The reaction mixture was heated at 100° C. for 12 hours under a nitrogen atmosphere. The mixture was subsequently concentrated in vacuo, diluted with water, and extracted with EtOAc (3×100 mL). The organic layers were combined, washed with brine, dried over anhydrous Na₂CO₃, filtered, and concentrated. The crude product was purified by column chromatography eluting with a gradient of petroleum ether (1-2%) and EtOAc to give the title compound (22 g, 95%). ¹H NMR (400 MHz, CDCl₃) δ ppm 7.33 (t, J=8.0 Hz, 1H), 7.18 (d, J=8.0 Hz, 1H), 6.85 (d, J=8.0 Hz, 1H), 6.67 (dd, J=11.0, 17.4 Hz, 1H), 5.75 (d, J=17.4 Hz, 1H), 5.35 (d, J=11.0 Hz, 1H), 3.93 (s, 3H), 3.84 (s, 3H); ESI-MS m/z [M+H]⁺ 193.

STEP C: methyl 2-formyl-6-methoxybenzoate

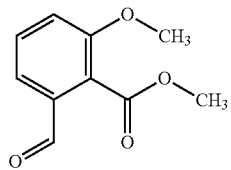

Into a solution of methyl 2-methoxy-6-vinylbenzoate (22 g, 0.11 mol) in anhydrous DCM (400 mL) was bubbled O₃ at −78° C. over a 30 minute period. Next, nitrogen gas was bubbled into the solution until it turned colorless. Dimethylsulfane (20 mL) was added dropwise and the resulting mixture was warmed to RT and stirred for 2 hours. The mixture was washed with water (30 mL) and the aqueous layer was extracted with DCM (3×100 mL). The organic layers were combined, dried over Na₂SO₄, and concentrated. The crude product was purified by column chromatography eluting with a gradient of EtOAc (0-90%) and PE to give the title compound (11.8 g, 53.6%). ¹H NMR (400 MHz, CDCl₃) δ ppm 9.97 (s, 1H), 7.56 (t, J=8.0 Hz, 1H), 7.47 (d, J=8.0 Hz, 1H), 7.22 (d, J=8.0 Hz, 1H), 3.98 (s, 3H), 3.90 (s, 3H).

STEP D: (Z)-methyl 2-methoxy-6-((5-oxo-2-phenyloxazol-4(5H)-ylidene)methyl)benzoate

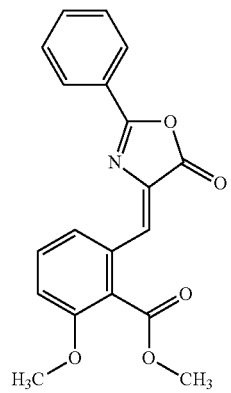 [SMILES: COC(=O)c1c(/C=C2\N=C(c3ccccc3)OC2=O)cccc1OC]

To a solution of methyl 2-formyl-6-methoxybenzoate (1.6 g, 8.24 mmol) in acetic anhydride (10 mL) was added 2-benzamidoacetic acid (1.77 g, 9.88 mmol) and NaOAc (810 mg, 9.88 mmol). The mixture was heated at 100° C. in a microwave reactor. The reactant mixture was partitioned between EtOAc (30 mL) and H$_2$O (50 mL). The organic layer was washed with saturated aqueous Na$_2$CO$_3$ (5×30 mL), dried over Na$_2$SO$_4$, and concentrated to give the title compound (7 g). ESI-MS m/z [M+H]$^+$ 338.1.

STEP E: methyl 8-methoxy-1-oxo-1,2-dihydroisoquinoline-3-carboxylate

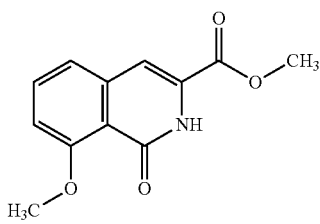 [SMILES: COC(=O)c1cc2cccc(OC)c2c(=O)[nH]1]

To a solution of (Z)-methyl 2-methoxy-6-((5-oxo-2-phenyloxazol-4(5H)-ylidene)methyl)benzoate (4.2 g, 12.45 mmol) in MeOH (50 mL) was added KOH (2.1 g, 37.35 mmol). The reaction mixture was heated to reflux for 1 hour. The solvent was subsequently removed and the residue was partitioned between water (30 mL) and EtOAc (20 mL). The aqueous layer was extracted with EtOAc (3×20 mL). The organic layers were combined, concentrated in vacuo, adjusted to pH=3 with a 4M solution of HCl in MeOH, and concentrated. The resulting brown solid which was purified by column chromatography eluting with petroleum ether and ethyl acetate (PE/EtOAc=5:1-1:1 gradient) to give the title compound (1 g, 26.3% over 2 steps). $^1$H NMR (400 MHz, CDCl$_3$) δ ppm 8.55 (s, 1H), 7.58 (t, 1H, J=8.0 Hz), 7.12 (d, 1H, J=8.0 Hz), 6.97 (d, 1H, J=8.0 Hz), 6.67 (s, 1H), 4.01 (s, 3H).

STEP F: 8-methoxy-1-oxo-1,2-dihydroisoquinoline-3-carboxamide

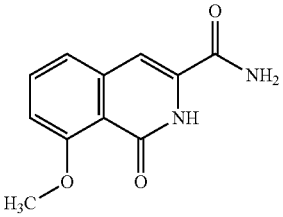 [SMILES: COc1cccc2cc(C(N)=O)[nH]c(=O)c12]

To a vessel containing NH$_3$/MeOH (20 mL) was added methyl 8-methoxy-1-oxo-1,2-dihydroisoquinoline-3-carboxylate (800 mg, 3.43 mmol). The vessel was sealed and the solution was stirred at 50° C. for 16 hours. The reaction mixture was subsequently concentrated in vacuo to give the title compound, which was used without further purification (800 mg). $^1$H NMR (400 MHz, DMSO-d$_6$) δ ppm 8.22 (s, 1H), 7.80 (s, 1H), 7.66 (t, 1H, J=8.0 Hz), 7.19-7.22 (m, 2H), 7.09 (d, J=8.0 Hz, 1H), 3.85 (s, 3H); ESI-MS m/z [M+H]$^+$ 219.

STEP G: 1-chloro-8-methoxyisoquinoline-3-carbonitrile

A solution of 8-methoxy-1-oxo-1,2-dihydroisoquinoline-3-carboxamide (800 mg, 3.66 mmol) in POCl$_3$ (40 mL) was heated to reflux for 1 hour. The reaction mixture was subsequently concentrated in vacuo to give the title compound (660 mg, 82%). $^1$H NMR (400 MHz, CDCl$_3$) δ ppm 7.98 (s, 1H), 7.78 (t, 1H, J=8.0 Hz), 7.48 (d, 1H, J=8.0 Hz), 7.20 (d, 1H, J=8.0 Hz), 4.05 (s, 3H); ESI-MS m/z [M+H]$^+$ 219.

Example 1

(R)-3-(1-((1-methacryloylpyrrolidin-3-yl)oxy)isoquinolin-3-yl)-1H-1,2,4-triazol-5(4H)-one

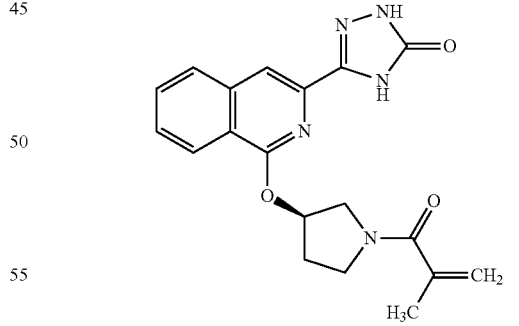

To a solution of (R)-3-(1-(pyrrolidin-3-yloxy)isoquinolin-3-yl)-1H-1,2,4-triazol-5(4H)-one (30 mg, 0.101 mmol) in DCM (3 mL) was added 2,6-dimethylpyridine (0.023 mL, 0.202 mmol) at 0° C. followed by methacryloyl chloride (21.10 mg, 0.202 mmol). The reaction mixture was stirred at RT overnight, which resulted in little conversion of the starting material. The reaction mixture was subsequently treated with excess 2,6-dimethylpyridine and methacryloyl chloride, stirred for 30 minutes, and concentrated. The residue was treated with MeOH and the crude product purified by preparative HPLC eluting with a gradient of 25-45% ACN in water (acid mode) to give a TFA salt of the title compound (6 mg, 16%). ¹H NMR (400 MHz, DMSO-$d_6$) (rotamers were observed) δ ppm 1.83 (s, 1.5 H), 1.89 (s, 1.5H), 2.10-2.75 (m, 2 H), 3.50-4.24 (m, 4 H), 5.10-5.40 (m, 2 H), 6.14 (d, J=12.38 Hz, 1 H), 7.62-7.70 (m, 1 H), 7.81 (t, J=7.58 Hz, 1 H), 7.98 (s, 1 H), 8.01 (d, J=8.08 Hz, 1 H), 8.11-8.22 (m, 1 H), 11.80 (s, 1 H), 12.04 (d, J=14.40 Hz, 1 H); ESI-MS m/z [M+H]⁺ 366.5.

Example 2

(R)-3-(1-((1-acryloylpyrrolidin-3-yl)oxy)isoquinolin-3-yl)-1H-1,2,4-triazol-5(4H)-one

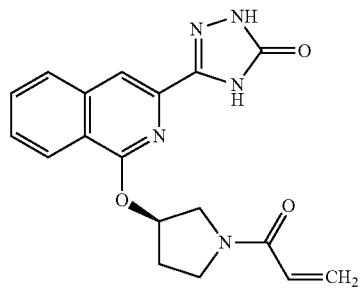 [SMILES: C=CC(=O)N1CC[C@@H](Oc2nc(-c3n[nH]c(=O)[nH]3)cc3ccccc23)C1]

To a solution of (R)-3-(1-(pyrrolidin-3-yloxy)isoquinolin-3-yl)-1H-1,2,4-triazol-5(4H)-one (11 mg, 0.037 mmol) in DCM (3 mL) was added 2,6-dimethylpyridine (5.80 μL, 0.050 mmol) at 0° C. followed by acryloyl chloride (8.08 μL, 0.100 mmol). The reaction mixture was stirred at RT overnight, forming a white solid. The solids were filtered and dried to give the title compound (4 mg, 23%). ¹H NMR (400 MHz, CD₃CN) δ ppm 2.22-2.51 (m, 2 H), 3.09-3.17 (m, 1 H), 3.68-3.91 (m, 2 H), 3.94 (br s, 1 H), 4.06 (d, J=12.13 Hz, 1 H), 5.60-5.76 (m, 1 H), 5.98 (br s, 1 H), 6.06 (br s, 1 H), 7.47-7.62 (m, 1 H), 7.62-7.74 (m, 1 H), 7.79 (d, J=7.58 Hz, 1 H), 7.92 (d, J=3.79 Hz, 1 H), 8.15 (d, J=8.08 Hz, 1 H); ESI-MS m/z [M+H]⁺ 352.0.

Example 3

(R,E)-3-(1-((1-(but-2-enoyl)pyrrolidin-3-yl)oxy)isoquinolin-3-yl)-1H-1,2,4-triazol-5(4H)-one

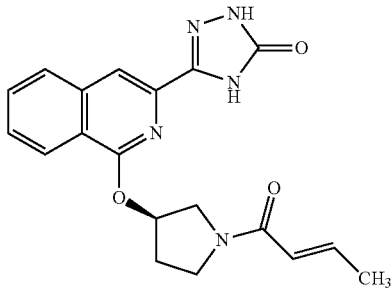 [SMILES: C/C=C/C(=O)N1CC[C@@H](Oc2nc(-c3n[nH]c(=O)[nH]3)cc3ccccc23)C1]

To a solution of (R)-3-(1-(pyrrolidin-3-yloxy)isoquinolin-3-yl)-1H-1,2,4-triazol-5(4H)-one (30 mg, 0.101 mmol) in DCM (3 mL) was added 2,6-dimethylpyridine (0.016 mL, 0.136 mmol) at 0° C. followed by (E)-but-2-enoyl chloride (28.5 mg, 0.273 mmol). The reaction mixture was stirred at RT overnight, which resulted in little conversion of the starting material. The reaction mixture was subsequently treated with excess 2,6-dimethylpyridine and (E)-but-2-enoyl chloride, stirred for 30 minutes, and concentrated. The reaction was quenched with MeOH and the crude product purified by preparative HPLC eluting with a gradient of 25-45% ACN in water (acid mode) to give a TFA salt of the title compound (10 mg, 20%). ¹H NMR (400 MHz, DMSO-$d_6$) (rotamers were observed) δ ppm 1.81 (d, J=1.52 Hz, 1.5H), 1.86 (d, J=1.52 Hz, 1.5H), 2.19-2.70 (m, 2 H), 3.59-4.11 (m, 4 H), 6.14 (m, 0.5 H), 6.22 (m, 0.5 H), 6.27 (dd, J=15.16 Hz, 1.77 Hz, 0.5 H), 6.37 (dd, J=15.16, 1.77 Hz, 0.5 H), 6.63-6.77 (m, 1 H), 7.61-7.70 (m, 1 H), 7.77-7.84 (m, 1 H), 7.99 (d, J=3.03 Hz, 1 H), 8.02 (d, J=9.09 Hz, 1 H), 8.16 (d, J=8.34 Hz, 1 H), 11.80 (br s, 1 H), 12.05 (d, J=4.04 Hz, 1H); ESI-MS m/z [M+H]⁺ 366.5.

Example 4

N-(1-(3-(5-oxo-4,5-dihydro-1H-1,2,4-triazol-3-yl)isoquinolin-1-yl)pyrrolidin-3-yl)acrylamide

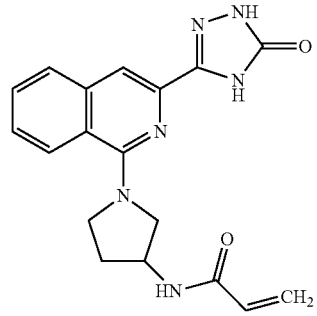 [SMILES: C=CC(=O)NC1CCN(c2nc(-c3n[nH]c(=O)[nH]3)cc3ccccc23)C1]

STEP A: tert-butyl (1-(3-cyanoisoquinolin-1-yl)pyrrolidin-3-yl)carbamate

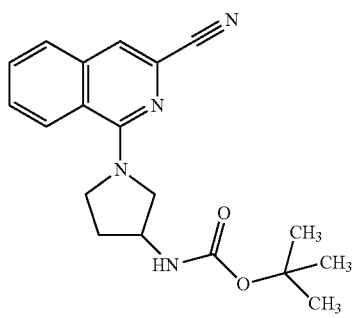 [SMILES: CC(C)(C)OC(=O)NC1CCN(c2nc(C#N)cc3ccccc23)C1]

A mixture of 1-chloroisoquinoline-3-carbonitrile (438 mg, 2.322 mmol), tert-butyl pyrrolidin-3-ylcarbamate (519 mg, 2.79 mmol) and Et₃N (0.653 mL, 4.64 mmol) in NMP (3 mL) was heated at 160° C. for 30 minutes in a microwave reactor. The crude reaction mixture, which contained the title compound, was used directly in the next step.

STEP B: 3-(1-(3-aminopyrrolidin-1-yl)isoquinolin-3-yl)-1H-1,2,4-triazol-5(4H)-one

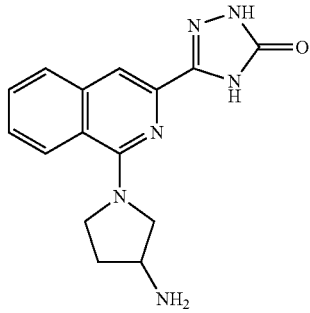 [SMILES: NC1CCN(c2nc(-c3n[nH]c(=O)[nH]3)cc3ccccc23)C1]

To a crude reaction mixture containing tert-butyl (1-(3-cyanoisoquinolin-1-yl)pyrrolidin-3-yl)carbamate (786 mg) was added ethyl hydrazinecarboxylate (242 mg, 2.323 mmol) in NMP (5 mL). The resulting suspension was heated at 175° C. overnight and was subsequently cooled, diluted with MeOH, and filtered. The crude product was purified using mass-triggered HPLC eluting with a gradient of 20-45% ACN in water (acid mode). The product-containing fractions were concentrated to give the title compound (117 mg, 17.0% over 2 steps). ESI-MS m/z [M+H]$^+$ 297.5.

STEP C: N-(1-(3-(5-oxo-4,5-dihydro-1H-1,2,4-triazol-3-yl)isoquinolin-1-yl)pyrrolidin-3-yl)acrylamide To a solution of tert-butyl (1-(3-(5-oxo-4,5-dihydro-1H-1,2,4-triazol-3-yl)isoquinolin-1-yl)pyrrolidin-3-yl)carbamate (80 mg, 0.202 mmol) in DCM (3 mL) was added 2,6-dimethylpyridine (0.023 mL, 0.202 mmol) at 0° C. followed by acryloyl chloride (0.033 mL, 0.404 mmol). The reaction mixture was stirred at RT overnight and was subsequently concentrated and partition between EtOAc and water. The organic phase was dried over Na$_2$SO$_4$, concentrated, and filtered. The crude product was purified using mass-triggered HPLC eluting with a gradient of 15-40% ACN in water (acid mode). The product-containing fractions were concentrated to give a TFA salt of the title compound (1 mg, 1.4%). $^1$H NMR (400 MHz, CD3OD) δ ppm 3.45 (br s, 1 H), 3.61 (br s, 1 H), 3.85 (br s, 1 H), 4.03 (br s, 1 H), 4.13 (br s, 1 H), 4.28 (br s, 1 H), 4.58 (br s, 1 H), 5.67 (br s, 1 H), 6.27 (br s, 2 H), 7.56 (br s, 1 H), 7.66 (br s, 2 H), 7.82 (br s, 1 H), 8.33 (br s, 1 H); ESI-MS m/z [M+H]$^+$ 351.4.

Example 5

(S)-3-(1-((1-acryloylpyrrolidin-3-yl)oxy)isoquinolin-3-yl)-1H-1,2,4-triazol-5(4H)-one

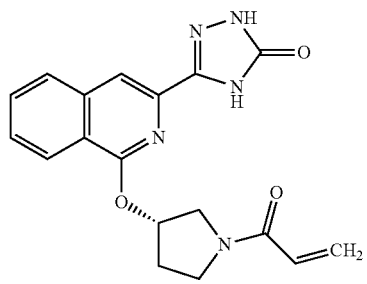 [SMILES: C=CC(=O)N1CC[C@H](Oc2nc(-c3n[nH]c(=O)[nH]3)cc3ccccc23)C1]

STEP A: (S)-tert-butyl 3-((3-chloroisoquinolin-1-yl)oxy)pyrrolidine-1-carboxylate

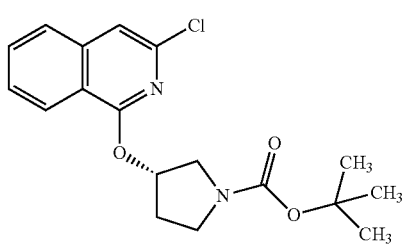 [SMILES: CC(C)(C)OC(=O)N1CC[C@H](Oc2nc(Cl)cc3ccccc23)C1]

To (S)-tert-butyl 3-hydroxypyrrolidine-1-carboxylate (1.134 g, 6.06 mmol) in NMP (10 mL) at 0° C. was added NaH (60%) (202 mg, 5.05 mmol). The mixture was stirred for 5 minutes and 1,3-dichloroisoquinoline (1.000 g, 5.05 mmol) was added. The reaction mixture was stirred at RT for 5 minutes and then heated at 135° C. for 30 minutes in a microwave reactor. The mixture was diluted with water (400 mL) and extracted with EtOAc (3×125 mL). The organic layers were combined, washed with brine, dried over Na$_2$SO$_4$, filtered, and concentrated in vacuo. The crude product was purified by silica column chromatography eluting with a gradient of 25-50% EtOAc in hexane to give the title compound (5.29 g, 75%). $^1$H NMR (500 MHz, DMSO-d$_6$) δ ppm 1.40 (d, J=14.16 Hz, 9 H), 2.12-2.34 (m, 2 H), 3.42-3.58 (m, 3 H), 3.69 (td, J=12.33, 4.64 Hz, 1 H), 5.63-5.76 (m, 1 H), 7.59 (s, 1 H), 7.64 (ddd, J=8.30, 7.08, 1.22 Hz, 1 H), 7.81 (td, J=7.57, 1.46 Hz, 1 H), 7.87-7.92 (m, 1 H), 8.11-8.19 (m, 1 H); ESI-MS m/z [M+H-tert-butyl]$^+$ 293.5.

STEP B: (S)-tert-butyl 3-((3-cyanoisoquinolin-1-yl)oxy)pyrrolidine-1-carboxylate

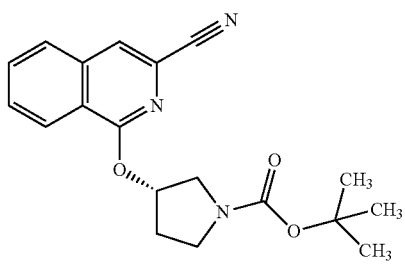 [SMILES: CC(C)(C)OC(=O)N1CC[C@H](Oc2nc(C#N)cc3ccccc23)C1]

A solution of (S)-tert-butyl 3-((3-chloroisoquinolin-1-yl)oxy)pyrrolidine-1-carboxylate (4.430 g, 12.70 mmol), zinc cyanide (2.980 g, 25.40 mmol) and Pd(PPh$_3$)$_4$ (1.468 g, 1.27 mmol) in DMF (36.3 mL) was heated at 160° C. for 20 minutes in a microwave reactor. The reaction mixture was filtered, diluted with water (400 mL) and extracted with EtOAc (2×100 mL). The organic layers were combined, washed with brine, dried over Na$_2$SO$_4$, and concentrated in vacuo. The crude product was purified by silica column chromatography to give the title compound as a white-to-pale-yellow solid (3.570 g, 83%). $^1$H NMR (500 MHz, DMSO-d$_6$) δ ppm 1.40 (d, J=13.18 Hz, 9 H), 2.23 (d, J=11.23 Hz, 2 H), 3.42-3.59 (m, 3 H), 3.65-3.75 (m, 1 H), 5.68-5.80 (m, 1 H), 7.82-7.89 (m, 1 H), 7.91-7.98 (m, 1 H), 8.06 (d, J=8.79 Hz, 1 H), 8.21-8.30 (m, 2 H); ESI-MS m/z [M+H-tert-butyl]$^+$ 284.6.

STEP C: (S)-tert-butyl 3-((3-(5-oxo-4,5-dihydro-1H-1,2,4-triazol-3-yl)isoquinolin-1-yl)oxy)pyrrolidine-1-carboxylate

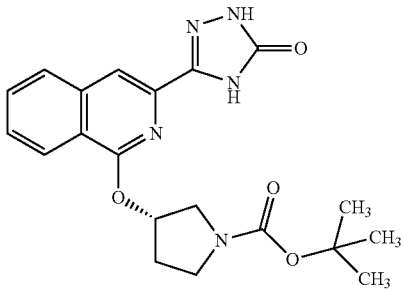 [SMILES: CC(C)(C)OC(=O)N1CC[C@H](Oc2nc(-c3n[nH]c(=O)[nH]3)cc3ccccc23)C1]

(S)-tert-Butyl 3-((3-cyanoisoquinolin-1-yl)oxy)pyrrolidine-1-carboxylate (4.670 g, 13.76 mmol), ethyl hydrazinecarboxylate (7.160 g, 68.80 mmol), DBU (1.037 mL, 6.88 mmol) and NMP (34.6 mL) were mixed in a 200 mL high pressure reaction vessel. The resulting suspension was heated at 170° C. overnight and was then cooled to room temperature. Crushed ice was added and the mixture was stirred. A yellow precipitate was collected by vacuum filtration, washed with additional water, and dried in a vacuum oven at 45° C. overnight to give the title compound, which was used in the next step without further purification (5.47 g). $^1$H NMR (500 MHz, DMSO-$d_6$) δ ppm 1.33-1.51 (m, 9 H), 2.09-2.38 (m, 2 H), 3.39-3.60 (m, 3 H), 3.75 (dd, J=12.20, 4.88 Hz, 1 H), 6.03-6.22 (m, 1 H), 7.62-7.71 (m, 1 H), 7.81 (td, J=7.57, 1.46 Hz, 1 H), 7.95-8.05 (m, 1 H), 8.11-8.29 (m, 2 H), 11.78 (s, 1 H), 12.03 (br s, 1 H).

STEP D: (S)-3-(1-(pyrrolidin-3-yloxy)isoquinolin-3-yl)-1H-1,2,4-triazol-5(4H)-one

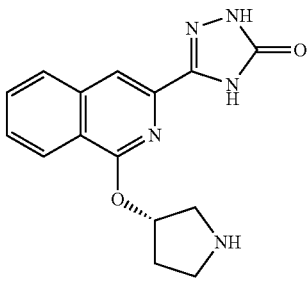 [SMILES: O=c1[nH]nc(-c2cc3ccccc3c(O[C@H]3CCNC3)n2)[nH]1]

To a 200 mL round-bottom flask charged with crude (S)-tert-butyl 3-((3-(5-oxo-4,5-dihydro-1H-1,2,4-triazol-3-yl)isoquinolin-1-yl)oxy)pyrrolidine-1-carboxylate (5.47 g) and dioxane (27.5 mL) was added 4M HCl in dioxane (13.76 mL, 55.1 mmol). The suspension was stirred at RT with periodic monitoring by HPLC. Upon completion, the reaction mixture was concentrated in vacuo to give an HCl salt of the title compound as a light tan powder that was dried and used without further purification. ESI-MS m/z [M+H]$^+$ 298.6.

STEP E: (S)-3-(1-((1-acryloylpyrrolidin-3-yl)oxy)isoquinolin-3-yl)-1H-1,2,4-triazol-5(4H)-one To a suspension of (S)-3-(1-(pyrrolidin-3-yloxy)isoquinolin-3-yl)-1H-1,2,4-triazol-5(4H)-one hydrochloride (4.29 g) in DCM (48.1 mL) was added 2,6-dimethylpyridine (3.19 mL, 27.4 mmol). Upon cooling the suspension to 0° C., acryloyl chloride (1.3 mL, 15.9 mmol) was added drop-wise. The reaction mixture was stirred for 15 minutes and warmed to RT over a period of 90 minutes. Additional 2,6-dimethylpyridine (1.68 mL, 14.43 mmol) and acryloyl chloride (0.469 mL, 5.77 mmol) were added and the mixture was stirred until HPLC indicated the reaction was completed. The product was collected by vacuum filtration, washed with DCM, and dried to give title compound as a pale yellow solid (1.929 g, 39.9% over 3 steps). $^1$H NMR (500 MHz, DMSO-$d_6$) δ ppm 2.16-2.43 (m, 2 H), 3.58-3.73 (m, 1 H), 3.74-3.91 (m, 2 H), 4.10 (dd, J=11.72, 4.88 Hz, 1 H), 5.60-5.74 (m, 1 H), 6.10-6.25 (m, 2 H), 6.53-6.73 (m, 1 H), 7.62-7.69 (m, 1 H), 7.77-7.85 (m, 1 H), 7.95-8.05 (m, 2 H), 8.17 (d, J=8.30 Hz, 1 H), 11.78 (s, 1 H), 12.03 (d, J=13.18 Hz, 1 H); ESI-MS m/z [M+H]$^+$ 352.6.

Example 6

(S)-3-(1-(((1-acryloylpyrrolidin-2-yl)methyl)amino)isoquinolin-3-yl)-1H-1,2,4-triazol-5(4H)-one

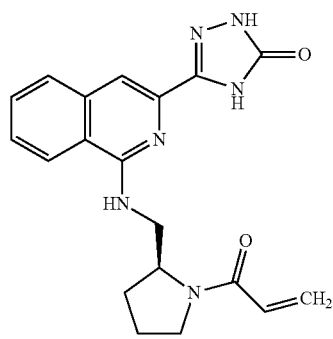 [SMILES: C=CC(=O)N1CCC[C@H]1CNc1nc(-c2n[nH]c(=O)[nH]2)cc2ccccc12]

STEP A: (S)-tert-butyl 2-(((3-cyanoisoquinolin-1-yl)amino)methyl)pyrrolidine-1-carboxylate

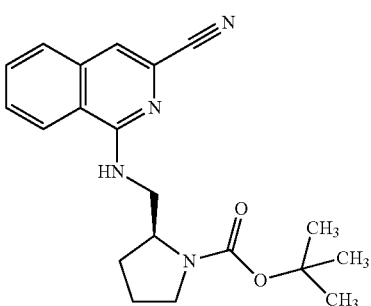

A mixture of (S)-tert-butyl 2-(aminomethyl)pyrrolidine-1-carboxylate (350 mg, 1.750 mmol) in NMP (4 mL) at 0° C. was treated with NaH (70.0 mg, 1.750 mmol) and stirred for 1 hour. Next, 1-chloroisoquinoline-3-carbonitrile (300 mg, 1.591 mmol) was added and the reaction mixture was stirred at RT for 15 minutes and then heated at 140° C. for 15 minutes in a microwave reactor. The crude reaction mixture, which contained the title compound, was used directly in the next step.

STEP B: (S)-tert-butyl 2-(((3-(5-oxo-4,5-dihydro-1H-1,2,4-triazol-3-yl)isoquinolin-1-yl)amino)methyl)pyrrolidine-1-carboxylate

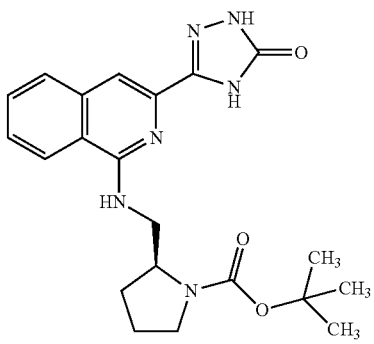 [SMILES: CC(C)(C)OC(=O)N1CCC[C@H]1CNc1nc(-c2n[nH]c(=O)[nH]2)cc2ccccc12]

To a crude reaction mixture containing (S)-tert-butyl 2-(((3-cyanoisoquinolin-1-yl)amino)methyl)pyrrolidine-1-carboxylate (0.561 g) was added ethyl hydrazinecarboxylate (0.663 g, 6.36 mmol). The reaction mixture was heated at 175° C. overnight and was subsequently cooled, diluted with EtOAc, and washed with saturated aqueous NH₄Cl. The aqueous and organic layers were separated. The organic layer was concentrated to give the title compound, which was used directly in the next step.

STEP C: (S)-3-(1-((pyrrolidin-2-ylmethyl)amino)isoquinolin-3-yl)-1H-1,2,4-triazol-5(4H)-one

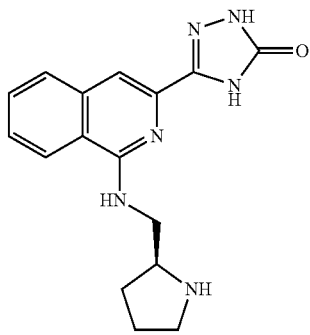 [SMILES: O=c1[nH]nc(-c2cc3ccccc3c(NC[C@@H]3CCCN3)n2)[nH]1]

To crude (S)-tert-butyl-2-(((3-(5-oxo-dihydro-1H-1,2,4-triazol-3-isoquinolin-1-yl)amino)methyl)pyrrolidine-1-carboxylate (653 mg) suspended in DCM (3 mL) was added TFA (2 mL). The mixture was stirred for 2 hours and then concentrated. The product was purified by preparative HPLC eluting with a gradient of 5-30% ACN in water (acid mode) to give the title compound.

STEP D: (S)-3-(1-(((1-acryloylpyrrolidin-2-yl)methyl)amino)isoquinolin-3-yl)-1H-1,2,4-triazol-5(4H)-one To a solution of (S)-3-(1-((pyrrolidin-2-ylmethyl)amino)isoquinolin-3-yl)-1H-1,2,4-triazol-5(4H)-one (50 mg, 0.161 mmol) in DCM (3 mL) was added 2,6-dimethylpyridine (0.056 mL, 0.483 mmol) at 0° C. followed by acryloyl chloride (0.026 mL, 0.322 mmol). The reaction mixture was stirred at RT for 30 minutes and then concentrated in vacuo. The residue was taken up in MeOH and the product purified by preparative HPLC eluting with a gradient of 15-40% ACN in water (acid mode) to give a TFA salt of the title compound (10 mg, 17%). ¹H NMR (400 MHz, CD₃OD) δ ppm 2.08-2.25 (m, 4 H), 3.53 (dd, J=13.64, 8.34 Hz, 1 H), 3.58-3.71 (m, 1 H), 3.79 (t, J=8.34 Hz, 1 H), 4.12 (dd, J=13.39, 3.79 Hz, 1 H), 4.68 (br s, 1 H), 5.84 (d, J=9.85 Hz, 1 H), 6.50-6.61 (m, 1 H), 6.61-6.72 (m, 1 H), 7.60-7.73 (m, 2 H), 7.78 (t, J=7.20 Hz, 1 H), 7.86 (d, J=7.83 Hz, 1 H), 8.20 (d, J=8.08 Hz, 1 H); ESI-MS m/z [M+H]⁺ 365.5.

Example 7

(S)-3-(1-((1-acryloylpyrrolidin-2-yl)methoxy)isoquinolin-3-yl)-1H-1,2,4-triazol-5(4H)-one

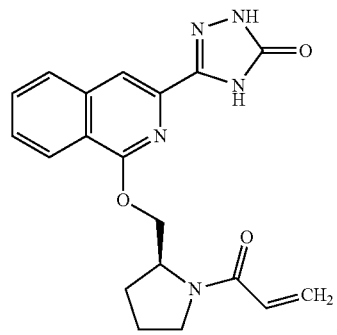 [SMILES: C=CC(=O)N1CCC[C@H]1COc1nc(-c2n[nH]c(=O)[nH]2)cc2ccccc12]

STEP A: (S)-tert-butyl 2-(((3-cyanoisoquinolin-1-yl)oxy)methyl)pyrrolidine-1-carboxylate

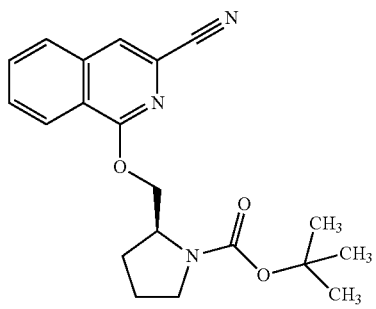 [SMILES: CC(C)(C)OC(=O)N1CCC[C@H]1COc1nc(C#N)cc2ccccc12]

A mixture of (S)-tert-butyl 2-(hydroxymethyl)pyrrolidine-1-carboxylate (222 mg, 1.103 mmol) in NMP (4 mL) at 0° C. was treated with Cs₂CO₃ (345 mg, 1.060 mmol) and stirred for 1 hour. Next, 1-chloroisoquinoline-3-carbonitrile (200 mg, 1.060 mmol) was added and the reaction mixture was stirred at RT for 15 minutes and then heated at 140° C. for 15 minutes in a microwave reactor. The crude reaction mixture, which contained the title compound, was used directly in the next step.

STEP B: (S)-tert-butyl 2-(((3-(5-oxo-4,5-dihydro-1H-1,2,4-triazol-3-yl)isoquinolin-1-yl)oxy)methyl)pyrrolidine-1-carboxylate

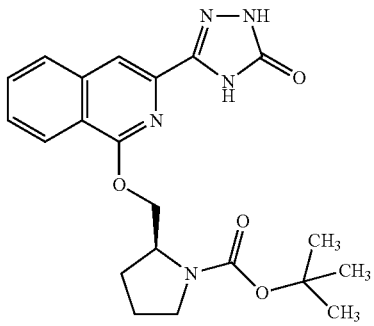 [SMILES: CC(C)(C)OC(=O)N1CCC[C@H]1COc1nc(-c2n[nH]c(=O)[nH]2)cc2ccccc12]

To a crude reaction mixture containing (S)-tert-butyl 2-(((3-cyanoisoquinolin-1-yl)oxy)methyl)pyrrolidine-1-carboxylate (0.562 g) was added NMP (2 mL) followed by ethyl hydrazinecarboxylate (0.663 g, 6.36 mmol). The reaction mixture was heated at 175° C. overnight and was subsequently cooled, diluted with EtOAc, and washed with brine. The organic layer was separated, dried over Na$_2$SO$_4$, and concentrated to give the title compound, which was used directly in the next step.

STEP C: (S)-3-(1-(pyrrolidin-2-ylmethoxy)isoquinolin-3-yl)-1H-1,2,4-triazol-5(4H)-one

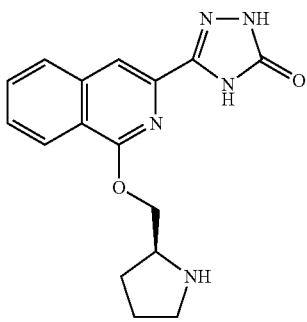 [SMILES: O=c1[nH]nc(-c2cc3ccccc3c(OC[C@@H]3CCCN3)n2)[nH]1]

To crude (S)-tert-butyl 2-(((3-(5-oxo-4,5-dihydro-1H-1,2,4-triazol-3-yl)isoquinolin-1-yl)oxy)methyl)pyrrolidine-1-carboxylate suspended in DCM (1 mL) was added TFA (1 mL). The mixture was stirred for 10 minutes and then concentrated. The product was purified by preparative HPLC eluting with a gradient of 15-22% ACN in water (acid mode) to give the title compound.

STEP D: (S)-3-(1-((1-acryloylpyrrolidin-2-yl)methoxy)isoquinolin-3-yl)-1H-1,2,4-triazol-5(4H)-one To a solution of (S)-3-(1-(pyrrolidin-2-ylmethoxy)isoquinolin-3-yl)-1H-1,2,4-triazol-5(4H)-one (50 mg, 0.161 mmol) in DCM (3 mL) was added 2,6-dimethylpyridine (0.056 mL, 0.482 mmol) at 0° C. followed by acryloyl chloride (0.026 mL, 0.321 mmol). The reaction mixture was stirred at RT for 30 minutes and then concentrated. The residue was taken up in MeOH and water and the product purified by preparative HPLC eluting with a gradient of 30-50% ACN in water (acid mode) to give a TFA salt of the title compound (14 mg, 24%); ESI-MS m/z [M+H]$^+$ 366.5.

Example 8

(S)-3-(1-(((1-acryloylpyrrolidin-3-yl)amino)isoquinolin-3-yl)-1H-1,2,4-triazol-5(4H)-one

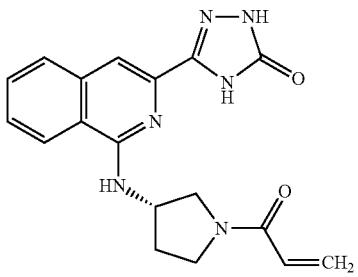 [SMILES: C=CC(=O)N1CC[C@H](Nc2nc(-c3n[nH]c(=O)[nH]3)cc3ccccc23)C1]

To a solution of (S)-3-(1-(pyrrolidin-3-ylamino)isoquinolin-3-yl)-1H-1,2,4-triazol-5(4H)-one (8 mg, 0.027 mmol) in DCM (3 mL) was added 2,6-dimethylpyridine (9.40 µL, 0.081 mmol) at 0° C. followed by acryloyl chloride (4.39 µL, 0.054 mmol). The mixture was stirred for 30 minutes and concentrated. The residue was dispersed in water and the product purified by preparative HPLC eluting with a gradient of 5-30% ACN in water (acid mode) to give a TFA salt of the title compound (2 mg, 21%). ESI-MS m/z [M+H]$^+$ 351.4.

Example 9

(R)-3-(1-((1-acryloylpyrrolidin-2-yl)methoxy)isoquinolin-3-yl)-1H-1,2,4-triazol-5(4H)-one

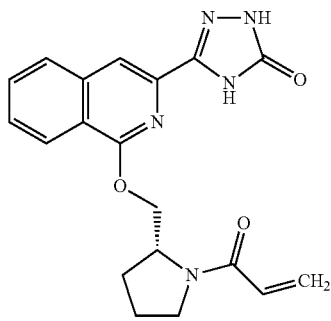 [SMILES: C=CC(=O)N1CCC[C@@H]1COc1nc(-c2n[nH]c(=O)[nH]2)cc2ccccc12]

STEP A: (R)-tert-butyl 2-(((3-cyanoisoquinolin-1-yl)oxy)methyl)pyrrolidine-1-carboxylate

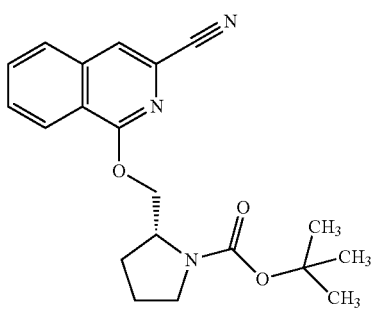 [SMILES: CC(C)(C)OC(=O)N1CCC[C@@H]1COc1nc(C#N)cc2ccccc12]

A mixture of (R)-tert-butyl 2-(hydroxymethyl)pyrrolidine-1-carboxylate (444 mg, 2.206 mmol) and Cs$_2$CO$_3$ (719 mg, 2.206 mmol) in NMP (4 mL) were stirred at 0° C. for 1 hour. Next, 1-chloroisoquinoline-3-carbonitrile (400 mg, 2.121 mmol) was added and the reaction mixture was heated at 140° C. for 15 minutes in a microwave reactor. Additional Cs$_2$CO$_3$ (719 mg, 2.206 mmol) was added. The reaction mixture heated at 140° C. for 1 hour to give the title compound, which was used directly in the next step.

STEP B: (R)-tert-butyl 2-(((3-(5-oxo-4,5-dihydro-1H-1,2,4-triazol-3-yl)isoquinolin-1-yl)oxy)methyl)pyrrolidine-1-carboxylate

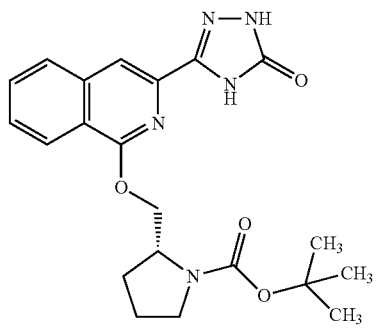 [SMILES: CC(C)(C)OC(=O)N1CCC[C@@H]1COc1nc(-c2n[nH]c(=O)[nH]2)cc2ccccc12]

To a crude reaction mixture containing (R)-tert-butyl 2-(((3-cyanoisoquinolin-1-yl)oxy)methyl)pyrrolidine-1-carboxylate (0.749 g) was added NMP (2 mL) and ethyl hydrazinecarboxylate (0.883 g, 8.48 mmol). The reaction mixture was heated at 175° C. overnight and was subsequently cooled, diluted with EtOAc, and washed with saturated aqueous NH$_4$Cl followed by water. The organic layer was separated and concentrated to give the title compound, which was used without further purification.

STEP C: (R)-3-(1-(pyrrolidin-2-ylmethoxy)isoquinolin-3-yl)-1H-1,2,4-triazol-5(4H)-one

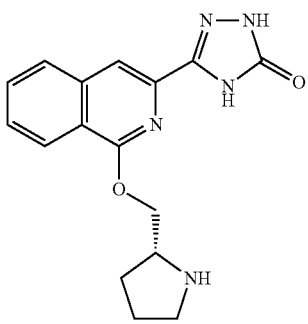 [SMILES: O=c1[nH]nc(-c2cc3ccccc3c(OC[C@H]3CCCN3)n2)[nH]1]

To crude (R)-tert-butyl 2-(((3-(5-oxo-4,5-dihydro-1H-1,2,4-triazol-3-yl)isoquinolin-1-yl)oxy)methyl)pyrrolidine-1-carboxylate was added DCM (3 mL) followed by TFA (2 mL). The mixture was stirred at RT for 2 hours and the solvent was removed in vacuo. The crude product was purified by preparative HPLC eluting with a gradient of 10-25% ACN in water (acid mode) to give the title compound (10 mg, 1.5% over 3 steps). ESI-MS m/z [M+H]$^+$ 312.4.

STEP D: (R)-3-(1-((1-acryloylpyrrolidin-2-yl)methoxy)isoquinolin-3-yl)-1H-1,2,4-triazol-5(4H)-one To a solution of (R)-3-(1-(pyrrolidin-2-ylmethoxy)isoquinolin-3-yl)-1H-1,2,4-triazol-5(4H)-one (10 mg, 0.032 mmol) in DCM (3 mL) was added 2,6-dimethylpyridine (0.011 mL, 0.096 mmol) at 0° C. followed by acryloyl chloride (5.22 µL, 0.064 mmol). The reaction mixture was stirred for 30 minutes. The solvent was subsequently removed in vacuo and the residue was taken up in MeOH and the product purified by preparative HPLC eluting with a gradient of 35-60% ACN in water (acid mode) to give a TFA salt of the title compound (1.8 mg, 15%). ESI-MS m/z [M+H]$^+$ 366.4.

Example 10

(S)-3-(1-((1-methacryloylpyrrolidin-3-yl)amino)isoquinolin-3-yl)-1H-1,2,4-triazol-5(4H)-one

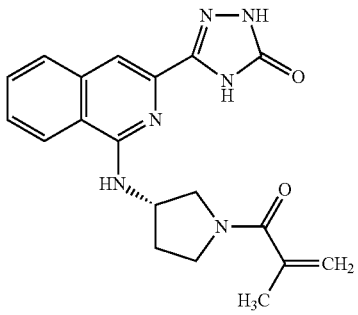 [SMILES: C=C(C)C(=O)N1CC[C@H](Nc2nc(-c3n[nH]c(=O)[nH]3)cc3ccccc23)C1]

To a solution of (S)-3-(1-(pyrrolidin-3-ylamino)isoquinolin-3-yl)-1H-1,2,4-triazol-5(4H)-one (13 mg, 0.044 mmol) in DCM (3 mL) was added 2,6-dimethylpyridine (0.015 mL, 0.132 mmol) at 0° C. followed by methacryloyl chloride (6.88 mg, 0.066 mmol). The reaction mixture was stirred at RT overnight and was subsequently partitioned between water and DCM. The organic phase was separated and concentrated in vacuo. The crude product was purified by preparative HPLC eluting with a gradient of 20-45% ACN in water (acid mode) to give a TFA salt of the title compound (0.5 mg, 2%). ESI-MS m/z [M+H]$^+$ 365.4.

Example 11

(S)-3-(1-((1-acryloylpyrrolidin-3-yl)(methyl)amino)isoquinolin-3-yl)-1H-1,2,4-triazol-5(4H)-one

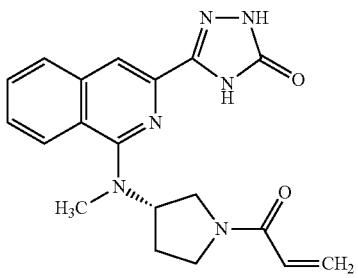 [SMILES: C=CC(=O)N1CC[C@H](N(C)c2nc(-c3n[nH]c(=O)[nH]3)cc3ccccc23)C1]

STEP A: (S)-tert-butyl 3-((3-cyanoisoquinolin-1-yl)(methyl)amino)pyrrolidine-1-carboxylate

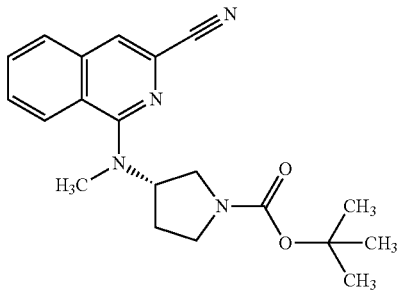 [SMILES: CN(c1nc(C#N)cc2ccccc12)[C@H]1CCN(C(=O)OC(C)(C)C)C1]

To (S)-tert-butyl 3-((3-cyanoisoquinolin-1-yl)amino)pyrrolidine-1-carboxylate (235 mg, 0.694 mmol) in DMF (6 mL) was added NaH (27.8 mg, 0.694 mmol) and methyl iodide (0.052 mL, 0.833 mmol) at 0° C. The reaction mixture was allowed to warm to RT with stirring over a 2 hour period and was subsequently diluted with EtOAc and washed with aqueous $NH_4Cl$, water, and brine. The organic layer was dried over $Na_2SO_4$, filtered, and concentrated. Toluene (2×5 mL) was added and removed in vacuo to give the title compound as a crude residue.

STEP B: (S)-tert-butyl 3-(methyl(3-(5-oxo-4,5-dihydro-1H-1,2,4-triazol-3-yl)isoquinolin-1-yl)amino)pyrrolidine-1-carboxylate

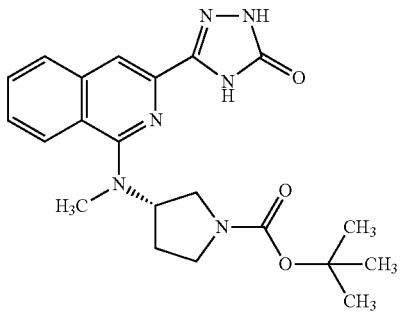 [SMILES: CN(c1nc(-c2n[nH]c(=O)[nH]2)cc2ccccc12)[C@H]1CCN(C(=O)OC(C)(C)C)C1]

To crude (S)-tert-butyl 3-((3-cyanoisoquinolin-1-yl)(methyl)amino)pyrrolidine-1-carboxylate (0.245 g) in NMP (1 mL) was added ethyl hydrazinecarboxylate (0.289 g, 2.78 mmol). The reaction mixture was heated at 175° C. for 2 days and was subsequently cooled, diluted with EtOAc, and washed with aqueous $NH_4Cl$. The organic phase was separated, dried, and concentrated. The crude product was purified by HPLC to give the title compound (91 mg, 32% over 2 steps).

STEP C: (S)-3-(1-(methyl(pyrrolidin-3-yl)amino)isoquinolin-3-yl)-1H-1,2,4-triazol-5(4H)-one

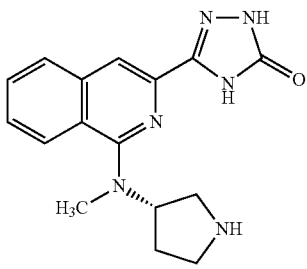 [SMILES: CN(c1nc(-c2n[nH]c(=O)[nH]2)cc2ccccc12)[C@H]1CCNC1]

To (S)-tert-butyl 3-(methyl(3-(5-oxo-4,5-dihydro-1H-1,2,4-triazol-3-yl)isoquinolin-1-yl)amino)pyrrolidine-1-carboxylate (91 mg, 0.222 mmol) in DCM was added TFA (1.5 mL). After 2 hours the solvent was removed in vacuo to give the title compound, which was used without further purification.

STEP D: (S)-3-(1-((1-acryloylpyrrolidin-3-yl)(methyl)amino)isoquinolin-3-yl)-1H-1,2,4-triazol-5(4H)-one To a solution of crude (S)-3-(1-(methyl(pyrrolidin-3-yl)amino)isoquinolin-3-yl)-1H-1,2,4-triazol-5(4H)-one (69 mg) in DCM (10 mL) was added 2,6-dimethylpyridine (0.077 mL, 0.667 mmol) at 0° C. followed by acryloyl chloride (0.023 mL, 0.278 mmol). The reaction mixture was stirred at RT overnight and then quenched with water. The solvent was removed in vacuo and the crude product was purified by preparative HPLC to give a TFA salt of the title compound (19 mg, 24% over 2 steps). $^1$H NMR (400 MHz, DMSO-$d_6$) (rotamers were observed) δ ppm 1.99-2.20 (m, 1 H), 2.20-2.40 (m, 1 H), 3.06 (s, 1.5H), 3.04 (s, 1.5H), 3.15-3.25 (m, 0.5 H), 3.30-3.47 (m, 1 H), 3.50-3.64 (m, 0.5 H), 3.65-3.75 (m, 0.5 H), 3.80-3.90 (m, 0.5 H), 3.98-4.06 (m 0.5 H), 4.22 (dd, J=9.85, 7.58 Hz, 0.5 H), 4.63-4.92 (m, 1 H), 5.66 (ddd, J=19.58, 10.23, 2.53 Hz, 1 H), 6.15 (ddd, J=16.67, 5.81, 2.53 Hz, 1 H), 6.49-6.72 (m, 1 H), 7.47-7.68 (m, 1 H), 7.68-7.81 (m, 1 H), 7.89-8.03 (m, 2 H), 8.16 (d, J=8.59 Hz, 1 H), 11.75 (s, 1 H), 11.93 (d, J=3.79 Hz, 1 H); ESI-MS m/z [M+H]$^+$ 365.4.

Example 12

(S)-3-(1-((1-methacryloylpyrrolidin-3-yl)oxy)isoquinolin-3-yl)-1H-1,2,4-triazol-5(4H)-one

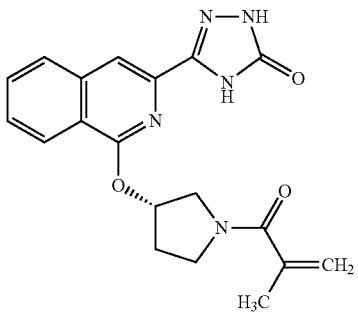 [SMILES: C=C(C)C(=O)N1CC[C@H](Oc2nc(-c3n[nH]c(=O)[nH]3)cc3ccccc23)C1]

To a solution of (S)-3-(1-(pyrrolidin-3-yloxy)isoquinolin-3-yl)-1H-1,2,4-triazol-5(4H)-one (17 mg, 0.057 mmol) in NMP (3 mL) was added 2,6-dimethylpyridine (8.97 µL, 0.077 mmol) at 0° C. followed by methacryloyl chloride (10.57 µL, 0.108 mmol). The reaction mixture was stirred at RT overnight and was subsequently diluted with MeOH, and filtered. The crude product was purified by mass-triggered HPLC eluting with a gradient of 25-50% ACN in water (acid mode). The product-containing fractions were concentrated to give a TFA salt of the title compound (10 mg, 35%). $^1$H NMR (400 MHz, $CD_3OD$) δ ppm 1.15-1.24 (m, 4 H), 3.59-3.83 (m, 3 H), 3.84-3.98 (m, 1 H), 5.08 (s, 1 H), 5.19 (d, J=5.81 Hz, 1 H), 5.28 (s, 1 H), 6.02 (d, J=15.16 Hz, 1 H), 7.52-7.59 (m, 1 H), 7.68 (td, J=7.58, 1.26 Hz, 1 H), 7.78-7.93 (m, 2 H), 8.06-8.20 (m, 1 H); ESI-MS m/z [M+H]$^+$ 366.4.

Example 13

(S)-3-(1-(((1-acryloylpyrrolidin-3-yl)oxy)methyl)isoquinolin-3-yl)-1H-1,2,4-triazol-5(4H)-one

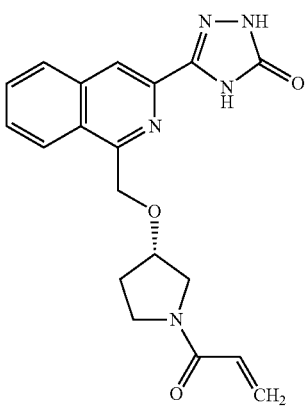 [SMILES: C=CC(=O)N1CC[C@H](OCc2nc(-c3n[nH]c(=O)[nH]3)cc3ccccc23)C1]

STEP A: (S)-tert-butyl 3-((3-cyanoisoquinolin-1-yl)methoxy)pyrrolidine-1-carboxylate

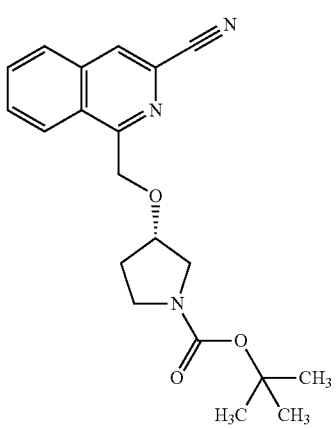 [SMILES: CC(C)(C)OC(=O)N1CC[C@H](OCc2nc(C#N)cc3ccccc23)C1]

To 1-(bromomethyl)isoquinoline-3-carbonitrile (0.150 g, 0.607 mmol) in DCM (6 mL) was added (S)-tert-butyl 3-hydroxypyrrolidine-1-carboxylate (0.114 g, 0.607 mmol) and AgOTf (0.016 g, 0.061 mmol). The suspension was stirred for 15 minutes at RT and then heated at 45° C. overnight. The reaction mixture was subsequently cooled, absorbed onto silica and eluted with a gradient of 0-5% MeOH in DCM. The enriched fractions were concentrated in vacuo to give the title compound as a yellow residue which was used without further purification (54.6 mg, 25.4%). ESI-MS m/z [M+H-tert butyl]+ 298.6.

STEP B: (S)-3-(1-((pyrrolidin-3-yloxy)methyl)isoquinolin-3-yl)-1H-1,2,4-triazol-5(4H)-one

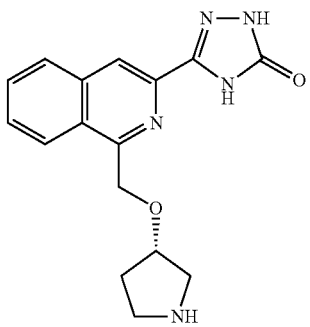 [SMILES: O=c1[nH]nc(-c2cc3ccccc3c(CO[C@H]3CCNC3)n2)[nH]1]

A mixture of (S)-tert-butyl 3-((3-cyanoisoquinolin-1-yl)methoxy)pyrrolidine-1-carboxylate (54.6 mg, 0.154 mmol) in NMP (0.4 mL), ethyl hydrazinecarboxylate (80 mg, 0.772 mmol) and DBU (0.012 mL, 0.077 mmol) was heated at 170° C. overnight and then filtered. The product in the filtrate was purified by mass-triggered HPLC eluting with a gradient of 35-60% ACN in water (acid mode). The product-containing fractions were concentrated in vacuo, treated with neat TFA (1 mL) for 5 minutes, and again concentrated in vacuo. The concentrate was dispersed in ACN/water (1:1) and lyophilized to give the title compound (7.5 mg, 16%). ESI-MS m/z [M+H]+ 312.6.

STEP C: (S)-3-(1-(((1-acryloylpyrrolidin-3-yl)oxy)methyl)isoquinolin-3-yl)-1H-1,2,4-triazol-5(4H)-one A suspension of (S)-3-(1-((pyrrolidin-3-yloxy)methyl)isoquinolin-3-yl)-1H-1,2,4-triazol-5(4H)-one (7.5 mg, 0.024 mmol) in DCM (134 µL) and 2,6-dimethylpyridine (5.61 µL, 0.048 mmol) was cooled to 0° C. Acryloyl chloride (3.91 µL, 0.048 mmol) was added drop-wise. The reaction mixture was slowly warmed to RT overnight with stirring. The reaction mixture was subsequently concentrated in vacuo, reconstituted in DMSO, and the product isolated by mass-triggered HPLC eluting with a gradient of 20-35% ACN in water (acid mode). The product-containing fractions were combined, concentrated in vacuo, and lyophilized to give a TFA salt of the title compound (0.9 mg, 10%). $^1$H NMR (500 MHz, CD$_3$OD) δ ppm 1.22-1.39 (m, 2 H), 1.96-2.31 (m, 1 H), 3.51 (d, J=9.28 Hz, 1 H), 3.57-3.88 (m, 2 H), 5.15-5.29 (m, 3 H), 5.70 (ddd, J=16.96, 10.62, 1.71 Hz, 1 H), 6.23 (td, J=17.09, 1.95 Hz, 1 H), 6.45-6.63 (m, 1 H), 7.74 (d, J=7.32 Hz, 1 H), 7.81 (t, J=7.57 Hz, 1 H), 7.85-7.96 (m, 1 H), 7.97-8.12 (m, 1 H), 8.30-8.47 (m, 3 H); ESI-MS m/z [M+H]+ 366.5.

Example 14

(S,E)-5-(1-((1-(4-(dimethylamino)but-2-enoyl)pyrrolidin-3-yl)oxy)isoquinolin-3-yl)-2,4-dihydro-3H-1,2,4-triazol-3-one

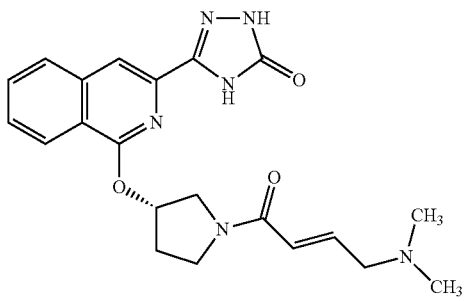 [SMILES: CN(C)C/C=C/C(=O)N1CC[C@H](Oc2nc(-c3n[nH]c(=O)[nH]3)cc3ccccc23)C1]

STEP A: (S)-tert-butyl 3-((3-cyanoisoquinolin-1-yl)oxy)pyrrolidine-1-carboxylate

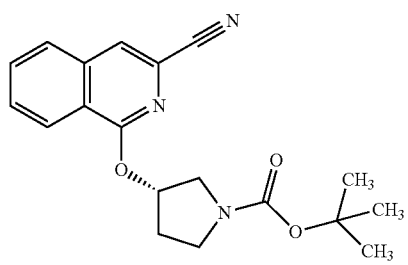 [SMILES: CC(C)(C)OC(=O)N1CC[C@H](Oc2nc(C#N)cc3ccccc23)C1]

To (S)-tert-butyl 3-hydroxypyrrolidine-1-carboxylate (1.906 g, 10.18 mmol) in NMP (10 mL) at 0° C. was added NaH (0.339 g, 8.48 mmol). The mixture was stirred for 5 minutes and then 1-chloroisoquinoline-3-carbonitrile (1.6 g, 8.48 mmol) was added. The reaction mixture was heated at 160° C. for 30 minutes in a microwave reactor and was subsequently diluted with water and extracted with EtOAc (2×). The organic phase was dried over $Na_2SO_4$ and concentrated. The crude product was purified by silica column chromatography eluting with a gradient of 0-75% EtOAc in hexane to give the title compound as a yellow solid (1.61 g, 55.9%). ESI-MS m/z [M+H-tert-butyl]⁺ 284.2.

STEP B: (S)-tert-butyl 3-((3-(5-oxo-4,5-dihydro-1H-1,2,4-triazol-3-yl)isoquinolin-1-yl)oxy)pyrrolidine-1-carboxylate

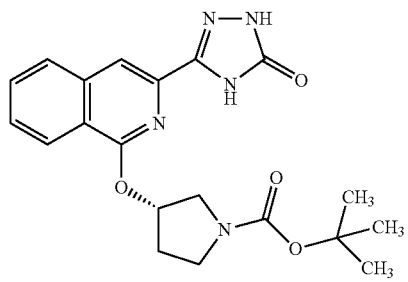 [SMILES: CC(C)(C)OC(=O)N1CC[C@H](Oc2nc(-c3n[nH]c(=O)[nH]3)cc3ccccc23)C1]

A mixture of (S)-tert-butyl 3-((3-cyanoisoquinolin-1-yl)oxy)pyrrolidine-1-carboxylate (1.61 g, 4.74 mmol) and ethyl hydrazinecarboxylate (1.482 g, 14.23 mmol) in NMP (8 mL) was heated at 160° C. overnight. The reaction mixture was diluted with EtOAc and washed with water (2×). The aqueous layer was back-extracted with EtOAc. The organic layers were combined, dried over $MgSO_4$, filtered, and evaporated in vacuo to give the title compound as a pale oil, which was used without further purification. ESI-MS m/z [M+H-tert-butyl]⁺ 342.3.

STEP C: (S)-3-(1-(pyrrolidin-3-yloxy)isoquinolin-3-yl)-1H-1,2,4-triazol-5(4H)-one

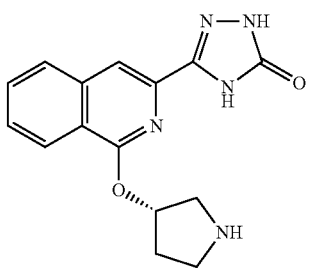 [SMILES: O=c1[nH]nc(-c2cc3ccccc3c(O[C@H]3CCNC3)n2)[nH]1]

Crude (S)-tert-butyl-3-((3-(5-oxo-4,5-dihydro-1H-1,2,4-triazol-3-yl)isoquinolin-1-yl)oxy)-pyrrolidine-1-carboxylate (1 g, 1.258 mmol) was dissolved in a solution of 4N HCl in dioxane (0.315 mL, 1.258 mmol) and stirred at RT for 30 minutes. The solvent was removed in vacuo and the resulting oil was dried under high vacuum to give the title compound, which used without further purification. ESI-MS m/z [M+H]⁺ 298.3.

STEP D: (S,E)-5-(1-((1-(4-(dimethylamino)but-2-enoyl)pyrrolidin-3-yl)oxy)isoquinolin-3-yl)-2,4-dihydro-3H-1,2,4-triazol-3-one To a mixture of (E)-4-(dimethylamino)but-2-enoic acid hydrochloride (23.40 mg, 0.141 mmol), (S)-3-(1-(pyrrolidin-3-yloxy)isoquinolin-3-yl)-1H-1,2,4-triazol-5(4H)-one (100 mg, 0.135 mmol) and HATU (61.4 mg, 0.161 mmol) in DCM (3 mL) was added Hünig's Base (0.070 mL, 0.404 mmol). The reaction mixture was stirred at RT overnight and was subsequently diluted with EtOAc and washed with water. The product remained in the aqueous layer, which was concentrated to afford a residue. The crude product was purified by preparative HPLC eluting with a gradient of 25-50% ACN in water (basic mode). The solvent was removed by lyophilization to give the title compound (26 mg, 47%). ¹H NMR (400 MHz, $CD_3OD$) δ ppm 2.33-2.44 (m, 1 H), 2.44-2.53 (m, 1 H), 2.55 (s, 3 H), 2.60 (s, 3 H), 3.53 (d, J=6.06 Hz, 1 H), 3.59 (d, J=6.57 Hz, 1 H), 3.72-3.91 (m, 1 H), 3.91-4.00 (m, 2 H), 4.14-4.18 (m, 1H), 6.15 (d, J=18.44 Hz, 1 H), 6.65-6.89 (m, 2 H), 7.58-7.69 (m, 1 H), 7.73-7.83 (m, 1 H), 7.90 (d, J=3.03 Hz, 1 H), 7.96 (d, J=5.31 Hz, 1 H), 8.21 (d, J=7.33 Hz, 1 H); ESI-MS m/z [M+H]⁺ 409.5.

Example 15

(S,E)-3-(1-((1-(but-2-enoyl)pyrrolidin-3-yl)amino)isoquinolin-3-yl)-1H-1,2,4-triazol-5(4H)-one

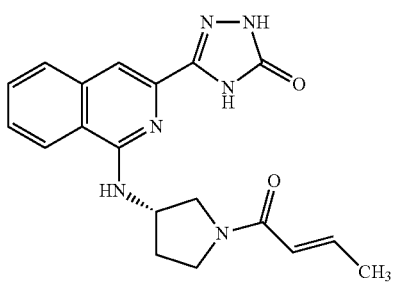 [SMILES: C/C=C/C(=O)N1CC[C@H](Nc2nc(-c3n[nH]c(=O)[nH]3)cc3ccccc23)C1]

To a solution of (S)-3-(1-(pyrrolidin-3-ylamino)isoquinolin-3-yl)-1H-1,2,4-triazol-5(4H)-one (70 mg, 0.236 mmol) in DCM (10 mL) was added 2,6-dimethylpyridine (0.082 mL, 0.709 mmol) at 0° C. followed by (E)-but-2-enoyl chloride (0.027 mL, 0.283 mmol). The reaction mixture was stirred at RT overnight. The reaction was subsequently quenched with water and the solvent was removed in vacuo to afford a residue. The crude product was purified by preparative HPLC eluting with a gradient of 20-45% ACN in water (acid mode) to give a TFA salt of the title compound (10 mg, 12%). $^1$H NMR (400 MHz, DMSO-d$_6$) (rotamers were observed) δ ppm 1.82 (dd, J=6.82, 1.52 Hz, 1.5 H), 1.86 (dd, J=6.82, 1.52 Hz, 1.5 H), 1.93-2.14 (m, 1 H), 2.15-2.39 (m, 1 H), 3.22-3.77 (m, 1 H), 3.75-3.95 (m, 2.5 H), 4.13 (dd, J=9.98, 7.20 Hz, 0.5 H), 5.10-5.34 (m, 1 H), 6.22-6.41 (m, 1 H), 6.64-6.78 (m, 1 H), 7.48-7.63 (m, 3 H), 7.63-7.73 (m, 1 H), 7.83 (dd, J=7.83, 3.03 Hz, 1 H), 8.34 (d, J=8.34 Hz, 1 H), 11.67 (d, J=1.77 Hz, 1 H), 11.81 (d, J=3.28 Hz, 1 H); ESI-MS m/z [M+H]$^+$ 365.4.

Example 16

(S)-3-(8-((1-acryloylpyrrolidin-3-yl)oxy)-1,7-naphthyridin-6-yl)-1H-1,2,4-triazol-5(4H)-one

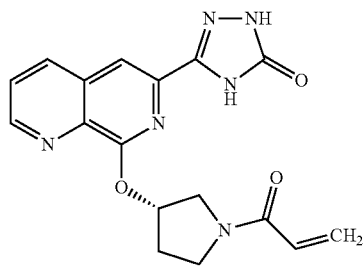 [SMILES: C=CC(=O)N1CC[C@H](Oc2nc(-c3n[nH]c(=O)[nH]3)cc3cccnc23)C1]

STEP A: (S)-tert-butyl 3-((6-bromo-1,7-naphthyridin-8-yl)oxy)pyrrolidine-1-carboxylate

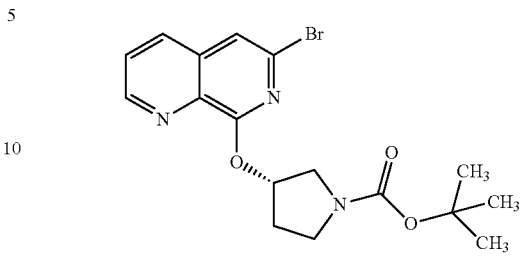

To (S)-tert-butyl 3-hydroxypyrrolidine-1-carboxylate (890 mg, 4.75 mmol) in N-methyl-2-pyrrolidinone (16 mL) at 0° C. was added NaH (60%) (158.4 mg, 3.96 mmol). The mixture was stirred for 5 minutes. Next, 1,3-dibromoisoquinoline (1139 mg, 3.96 mmol) was added and the reaction mixture was stirred at RT for 5 minutes and then heated in a microwave reactor at 135° C. for 30 minutes and at 160° C. at for another 30 minutes. The mixture was subsequently diluted with water and extracted with EtOAc (2×). The organic phase was separated, dried over Na$_2$SO$_4$, and concentrated. The crude product was purified by silica column chromatography eluting with a gradient of 0-75% EtOAc in hexane over a 45 minute period to give the title compound (1.3 g, 70% from two batches).

STEP B: (S)-tert-butyl 3-((6-cyano-1,7-naphthyridin-8-yl)oxy)pyrrolidine-1-carboxylate

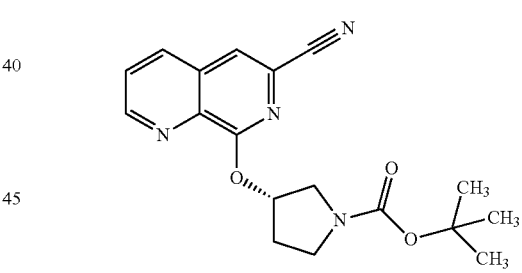

A solution of (S)-tert-butyl 3-((6-bromo-1,7-naphthyridin-8-yl)oxy)pyrrolidine-1-carboxylate (1400 mg, 3.55 mmol), zinc cyanide (834 mg, 7.1 mmol) and N1,N1,N2,N2-tetramethylethane-1,2-diamine (0.106 mL, 0.71 mmol) in DMSO (9 mL) was degassed with nitrogen for 5 minutes. Xantphos (206 mg, 0.355 mmol) and Pd$_2$(dba)$_3$ (325 mg, 0.355 mmol) were added and the mixture was heated in a microwave reactor at 160° C. for 15 minutes. The reaction mixture was diluted with EtOAc and washed with water (2×). The organic layer was separated and concentrated in vacuo. The crude product was purified by silica column chromatography to give the title compound as a yellow solid (181 mg, 15%).

STEP C: (S)-tert-butyl 3-((6-(5-oxo-4,5-dihydro-1H-1,2,4-triazol-3-yl)-1,7-naphthyridin-8-yl)oxy)pyrrolidine-1-carboxylate

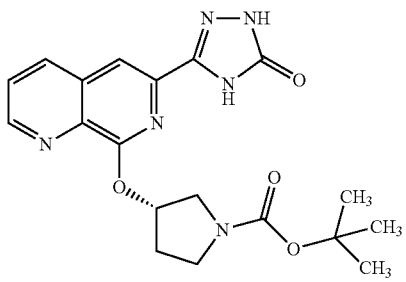 [SMILES: CC(C)(C)OC(=O)N1CC[C@H](Oc2nc(-c3n[nH]c(=O)[nH]3)cc3cccnc23)C1]

A suspension of (S)-tert-butyl 3-((6-cyano-1,7-naphthyridin-8-yl)oxy)pyrrolidine-1-carboxylate (181 mg, 0.532 mmol) and ethyl hydrazinecarboxylate (277 mg, 2.66 mmol) in NMP (5 mL) was heated at 175° C. overnight. The reaction mixture was subsequently diluted with MeOH and filtered. The crude product was purified using mass-triggered HPLC eluting with a gradient of 25-50% ACN in water (acid mode). The product-containing fractions were collected and concentrated to give a TFA salt of the title compound as a yellow film (100 mg, 47.2%).

STEP D: (S)-3-(8-(pyrrolidin-3-yloxy)-1,7-naphthyridin-6-yl)-1H-1,2,4-triazol-5(4H)-one

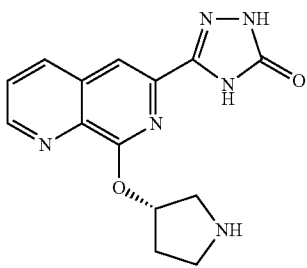 [SMILES: O=c1[nH]nc(-c2cc3cccnc3c(O[C@H]3CCNC3)n2)[nH]1]

To (S)-tert-butyl 3-((6-(5-oxo-4,5-dihydro-1H-1,2,4-triazol-3-yl)-1,7-naphthyridin-8-yl)oxy)pyrrolidine-1-carboxylate (100 mg, 0.251 mmol) suspended in dioxane (10 mL) was added 4M HCl in dioxane (0.251 mL, 1.004 mmol). The reaction mixture was stirred for 30 minutes and concentrated to give an HCl salt of the title compound (74 mg, 88%). This material was used directly in next step.

STEP E: (S)-3-(8-((1-acryloylpyrrolidin-3-yl)oxy)-1,7-naphthyridin-6-yl)-1H-1,2,4-triazol-5(4H)-one To a solution of (S)-3-(8-(pyrrolidin-3-yloxy)-1,7-naphthyridin-6-yl)-1H-1,2,4-triazol-5(4H)-one (74.0 mg, 0.248 mmol) in DMSO (3 mL) was added 2,6-dimethylpyridine (0.030 mL, 0.258 mmol) at 0° C. followed by acryloyl chloride (65.4 mg, 0.724 mmol). The reaction mixture was stirred at RT overnight and was subsequently diluted with MeOH and filtered through a PTFE membrane. The product, which was contained in the filtrate, was isolated using mass-triggered HPLC eluting with a gradient of 15-30% ACN in water (acid mode). The product-containing fractions were concentrated to give a TFA salt of the title compound (14 mg, 12% from two batches). $^1$H NMR (400 MHz, CD$_3$OD) δ ppm 2.34-2.58 (m, 2 H), 3.76-3.99 (m, 2 H), 3.99-4.11 (m, 1 H), 4.16 (dd, J=12.25, 4.42 Hz, 1 H), 5.64-5.85 (m, 1 H), 6.19 (br s, 1H), 6.29 (ddd, J=16.80, 3.66, 2.02 Hz, 1 H), 6.52-6.76 (m, 1 H), 7.82 (dd, J=8.21, 4.17 Hz, 1 H), 8.00-8.15 (m, 1 H), 8.44 (d, J=8.59 Hz, 1 H), 8.95 (br s, 1 H); ESI-MS m/z [M+H]$^+$ 353.3.

Example 17

(S)-3-(8-((1-acryloylpyrrolidin-3-yl)amino)-1,7-naphthyridin-6-yl)-1H-1,2,4-triazol-5(4H)-one

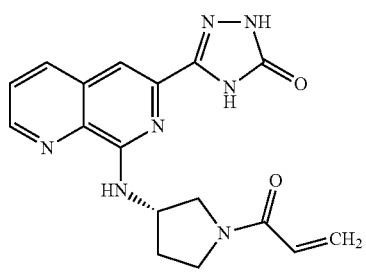 [SMILES: C=CC(=O)N1CC[C@H](Nc2nc(-c3n[nH]c(=O)[nH]3)cc3cccnc23)C1]

STEP A: (S)-tert-butyl 3-((6-bromo-1,7-naphthyridin-8-yl)amino)pyrrolidine-1-carboxylate

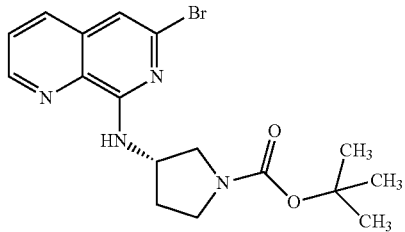 [SMILES: CC(C)(C)OC(=O)N1CC[C@H](Nc2nc(Br)cc3cccnc23)C1]

To (S)-tert-butyl 3-aminopyrrolidine-1-carboxylate (0.776 g, 4.17 mmol) in N-methyl-2-pyrrolidinone (12 mL) at 0° C. was added NaH (0.139 g, 3.47 mmol). The mixture was stirred for 5 minutes. Next, 6,8-dibromo-1,7-naphthyridine (1 g, 3.47 mmol) was added and the reaction mixture was stirred at RT for 5 minutes and then heated at 135° C. for 30 minutes in a microwave reactor. The reaction mixture was diluted with water and extracted with EtOAc (2×). The organic layers were combined, dried over Na$_2$SO$_4$, and concentrated. The crude product was purified using silica column chromatography eluting with a gradient of 0-75% EtOAc in hexane over a 45 minute period to give the title compound as a yellow solid (1.3 g, 95%).

STEP B: (S)-tert-butyl 3-((6-cyano-1,7-naphthyridin-8-yl)amino)pyrrolidine-1-carboxylate

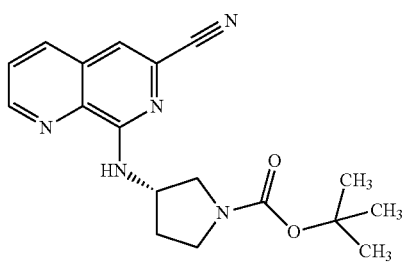 [SMILES: CC(C)(C)OC(=O)N1CC[C@H](Nc2nc(C#N)cc3cccnc23)C1]

A solution of (S)-tert-butyl 3-((6-bromo-1,7-naphthyridin-8-yl)amino)pyrrolidine-1-carboxylate (1141 mg, 2.9 mmol), zinc cyanide (681 mg, 5.80 mmol) and N1,N1,N2,N2-tetramethylethane-1,2-diamine (87 μL, 0.580 mmol) in NMP was degassed with nitrogen for 5 minutes. Xantphos (168 mg, 0.290 mmol) and Pd$_2$dba$_3$ (266 mg, 0.290 mmol) were added and the mixture was heated in a microwave reactor at 160° C. for 10 minutes. The reaction mixture was subsequently diluted with EtOAc. The organic phase was washed with water (2×), dried, and concentrated in vacuo. The crude product was purified by preparative HPLC eluting with a gradient of 45-70% ACN in water (acid mode) to give the title compound as a yellow solid (175 mg, 17.8%).

STEP C: (S)-tert-butyl 3-((6-(5-oxo-4,5-dihydro-1H-1,2,4-triazol-3-yl)-1,7-naphthyridin-8-yl)amino)pyrrolidine-1-carboxylate

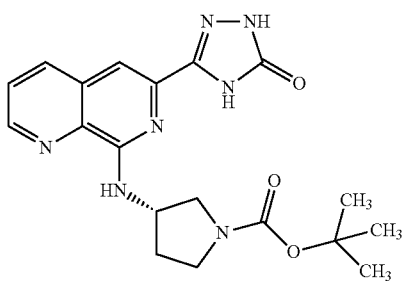 [SMILES: CC(C)(C)OC(=O)N1CC[C@H](Nc2nc(-c3n[nH]c(=O)[nH]3)cc3cccnc23)C1]

To (S)-tert-butyl 3-((6-cyano-1,7-naphthyridin-8-yl)amino)pyrrolidine-1-carboxylate (210 mg, 0.619 mmol) in NMP (1.5 mL) was added ethyl hydrazinecarboxylate (258 mg, 2.475 mmol). The reaction mixture was heated at 175° C. for 2 days and was then cooled, diluted with EtOAc, and washed with aqueous NH$_4$Cl. The organic phase was dried and concentrated. The crude product was purified by preparative HPLC eluting with a gradient of 35-60% ACN in water (acid mode) to give the title compound (80 mg, 33%).

STEP D: (S)-3-(8-(pyrrolidin-3-ylamino)-1,7-naphthyridin-6-yl)-1H-1,2,4-triazol-5(4H)-one

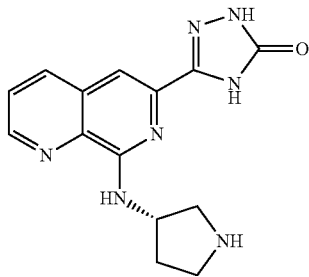 [SMILES: O=c1[nH]nc(-c2cc3cccnc3c(N[C@H]3CCNC3)n2)[nH]1]

A mixture of (S)-tert-butyl 3-((6-(5-oxo-4,5-dihydro-1H-1,2,4-triazol-3-yl)-1,7-naphthyridin-8-yl)amino)pyrrolidine-1-carboxylate (80 mg, 0.201 mmol) in DCM (3 mL) was treated with TFA (1.5 mL) for 2 hours. The solvent was removed in vacuo to give the title compound, which was used in the next step without further purification.

STEP E: (S)-3-(8-((1-acryloylpyrrolidin-3-yl)amino)-1,7-naphthyridin-6-yl)-1H-1,2,4-triazol-5(4H)-one To a solution of (S)-3-(8-(pyrrolidin-3-ylamino)-1,7-naphthyridin-6-yl)-1H-1,2,4-triazol-5(4H)-one (36 mg, 0.121 mmol) in DCM (3 mL) was added 2,6-dimethylpyridine (0.042 mL, 0.363 mmol) at 0° C. followed by acryloyl chloride (0.015 mL, 0.182 mmol). The reaction mixture was stirred at RT overnight. The reaction was subsequently quenched with water and the mixture was concentrated in vacuo. The crude product was purified by preparative HPLC eluting with a gradient of 15-40% ACN in water (acid mode) to give a TFA salt of the title compound (16 mg, 38%). $^1$H NMR (400 MHz, DMSO-d$_6$) (rotamers were observed) δ ppm 1.94-2.30 (m, 2 H), 3.20-3.50 (m, 1.5 H), 3.51-3.67 (m, 1 H), 3.72-3.91 (m, 1 H), 4.05 (dd, J=9.85, 7.07 Hz, 0.5 H), 4.99-5.25 (m, 1 H), 5.60 (ddd, J=16.11, 10.29, 2.40 Hz, 1 H), 6.00-6.16 (m, 1 H), 6.43-6.65 (m, 1 H), 7.47 (d, J=3.79 Hz, 1 H), 7.65 (ddd, J=8.27, 4.23, 1.39 Hz, 1 H), 7.73-7.88 (m, 1 H), 8.23 (dt, J=8.34, 1.77 Hz, 1 H), 8.74 (dt, J=4.29, 1.52 Hz, 1 H), 11.66 (s, 1 H), 11.83 (s, 1 H); ESI-MS m/z [M+H]$^+$ 352.4.

Example 18

(S)-3-(1-((1-acryloylpyrrolidin-3-yl)oxy)-7-fluoroisoquinolin-3-yl)-1H-1,2,4-triazol-5(4H)-one

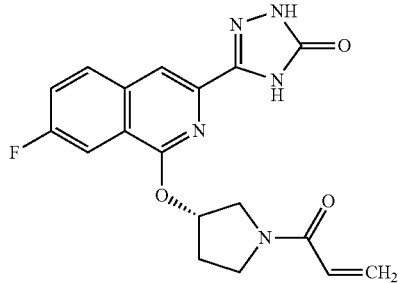 [SMILES: C=CC(=O)N1CC[C@H](Oc2nc(-c3n[nH]c(=O)[nH]3)cc3ccc(F)cc23)C1]

STEP A: (S)-tert-butyl 3-((3-chloro-7-fluoroisoquinolin-1-yl)oxy)pyrrolidine-1-carboxylate

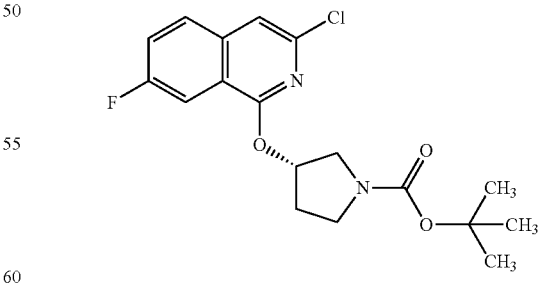

To a solution of (S)-tert-butyl 3-hydroxypyrrolidine-1-carboxylate (1.56 g, 8.3 mmol) in THF (20 mL) was added NaH (0.33 g, 8.3 mmol) under nitrogen at 0° C. The mixture was warmed to RT over a 30 minute period and 1,3-dichloro-7-fluoroisoquinoline (0.9 g, 4.17 mmol) was added. The resulting mixture was stirred for 10 hours at RT. The mixture was subsequently diluted with EtOAc (100 mL), quenched with saturated aqueous NH₄Cl (100 mL), and extracted with EtOAc (3×100 mL). The combined organic layers were dried over Na₂SO₄ and concentrated. The crude product was purified by column chromatography eluting with petroleum ether and ethyl acetate (PE/EtOAc=50:1-10:1 gradient) to give the title compound (1.1 g, 72%). ¹H NMR (400 MHz, DMSO-d₆) δ ppm 8.00-7.98 (m, 1H), 7.82-7.80 (m, 2H), 7.62 (s, 1H), 5.67-5.63 (d, J=16 Hz, 1H), 3.69-3.66 (m, 1H), 3.53-3.487 (m, 3H), 2.30-2.22 (m, 2H), 1.41-1.39 (d, J=10.8 Hz, 2H).

STEP B: (S)-tert-butyl 3-((3-cyano-7-fluoroisoquinolin-1-yl)oxy)pyrrolidine-1-carboxylate

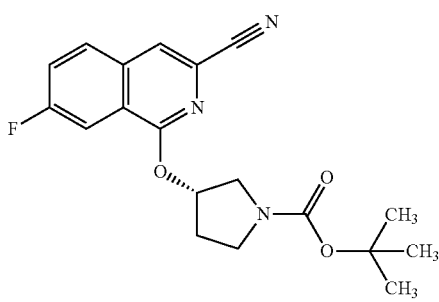 [SMILES: CC(C)(C)OC(=O)N1CC[C@H](Oc2nc(C#N)cc3ccc(F)cc23)C1]

To a solution of (S)-tert-butyl 3-((3-chloro-7-fluoroisoquinolin-1-yl)oxy)pyrrolidine-1-carboxylate (1 g, 2.73 mmol) in DMF (10 mL) was added Zn(CN)₂ (0.64 g, 5.46 mmol) and Pd(PPh₃)₄ (0.316 g, 0.273 mmol) under N₂. The mixture was heated at 160° C. for 30 minutes in a microwave reactor and was subsequently partition between EtOAc (50 mL) and water (50 mL). The aqueous phase was back-extracted with EtOAc (3×50 mL) and the organic layers were combined and washed with saturated aqueous NaCl (3×50 mL) and concentrated in vacuo. The crude product was purified by column chromatography eluting with petroleum ether and ethyl acetate (PE/EtOAc=20:1-5:1 gradient) to give the title compound (0.65 g, 65%). ¹H NMR (400 MHz, DMSO-d₆) δ ppm 8.28 (s, 1H), 8.19-8.16 (dd, J₁=5.2 Hz, J₂=3.6 Hz, 1H), 7.97-7.95 (m, 2H), 5.73-5.69 (d, J=16 Hz, 1H), 3.71-3.67 (m, 1H), 3.58-3.50 (m, 3H), 2.25-2.24 (d, J=4 Hz, 2H), 1.42-1.39 (d, J=12 Hz, 9H).

STEP C: (S)-tert-butyl 3-((7-fluoro-3-(hydrazinyl(imino)methyl)isoquinolin-1-yl)oxy)pyrrolidine-1-carboxylate

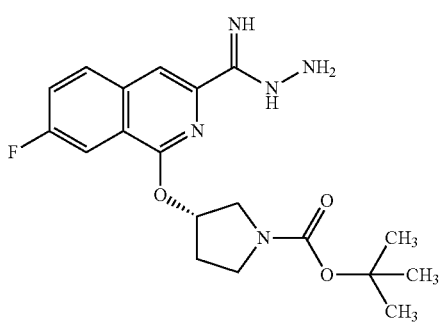 [SMILES: CC(C)(C)OC(=O)N1CC[C@H](Oc2nc(C(=N)NN)cc3ccc(F)cc23)C1]

To a mixture of (S)-tert-butyl 3-((3-cyano-7-fluoroisoquinolin-1-yl)oxy)pyrrolidine-1-carboxylate (400 mg, 1.12 mmol) in MeOH (5 mL) was added NH₂NH₂.H₂O (5 mL). The reaction mixture was heated to reflux for 2 hours. The solvent was subsequently removed to give the title compound as a white solid, which was used in next step without purification (450 mg, 100%). ESI-MS m/z [M+H]⁺ 390.

STEP D: (S)-tert-butyl 3-((7-fluoro-3-(5-oxo-4,5-dihydro-1H-1,2,4-triazol-3-yl)isoquinolin-1-yl)oxy)pyrrolidine-1-carboxylate

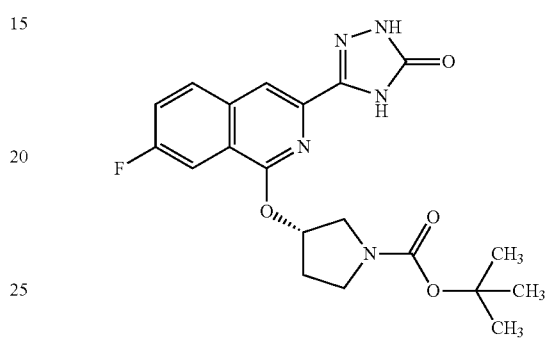

To a solution of (S)-tert-butyl 3-((7-fluoro-3-(hydrazinyl(imino)methyl)isoquinolin-1-yl)oxy)pyrrolidine-1-carboxylate (0.45 g, 1.12 mmol) in dioxane (10 mL) was added CDI (0.72 g, 2.24 mmol) under N₂. The mixture was heated to reflux for 2 hours and was subsequently concentrated in vacuo. The crude product was purified by preparative HPLC to give the title compound (70 mg, 40%). ESI-MS m/z [M+H-Boc]⁺ 316.

STEP E: (S)-3-(7-fluoro-1-(pyrrolidin-3-yloxy)isoquinolin-3-yl)-1H-1,2,4-triazol-5(4H)-one

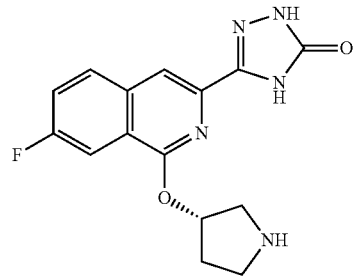 [SMILES: O=c1[nH]nc(-c2cc3ccc(F)cc3c(O[C@H]3CCNC3)n2)[nH]1]

A solution of (S)-tert-butyl 3-((7-fluoro-3-(5-oxo-4,5-dihydro-1H-1,2,4-triazol-3-yl)isoquinolin-1-yl)oxy)pyrrolidine-1-carboxylate (70 mg, 0.15 mmol) in HCl/EtOAc (5 mL) was stirred at RT for 30 minutes. The mixture was subsequently concentrated in vacuo to give the title compound, which was used in the next step without further purification (60 mg, 100%). ESI-MS m/z [M+H]⁺ 316.

STEP F: (S)-3-(1-((1-acryloylpyrrolidin-3-yl)oxy)-7-fluoroisoquinolin-3-yl)-1H-1,2,4-triazol-5(4H)-one To (S)-3-(7-fluoro-1-(pyrrolidin-3-yloxy)isoquinolin-3-yl)-1H-1,2,4-triazol-5(4H)-one (60 mg, 1.61 mmol) in DCM (10 mL) was added 2,6-dimethylpyridine (51 mg, 0.475 mmol). The mixture was cooled to −40° C. Acryloyl chloride (17 mg, 0.20 mmol) was added and the mixture was warmed to 0° C. over a 30 minute period. The reaction was subsequently quenched with MeOH (5 mL) and the mixture concentrated in vacuo. The crude product was purified by preparative HPLC to give the title compound (16.4 mg, 27%). $^1$H NMR (400 MHz, DMSO-d$_6$) δ ppm 12.06 (s, 1H), 11.82 (s, 1H), 8.17-8.13 (t, J=8 Hz, 1H), 8.05 (s, 1H), 7.88-7.85 (d, J=12 Hz, 1H), 7.78-7.76 (t, J=8 Hz, 1H), 6.50-6.70 (m, 1H), 6.19-6.13 (m, 2H), 5.73-5.67 (dd, J$_1$=12 Hz, J$_2$=4 Hz, 1H), 4.11-4.08 (m, 0.5H), 3.87-3.82 (m, 2H), 3.69-3.65 (m, 1.5H), 2.38-2.25 (m, 2H); ESI-MS m/z [M+H]$^+$ 370.

Example 19

3-(1-(((3R,4S)-1-acryloyl-4-methylpyrrolidin-3-yl)oxy)isoquinolin-3-yl)-1H-1,2,4-triazol-5(4H)-one and 3-(1-(((3S,4R)-1-acryloyl-4-methylpyrrolidin-3-yl)oxy)isoquinolin-3-yl)-1H-1,2,4-triazol-5(4H)-one (mixture of enantiomers)

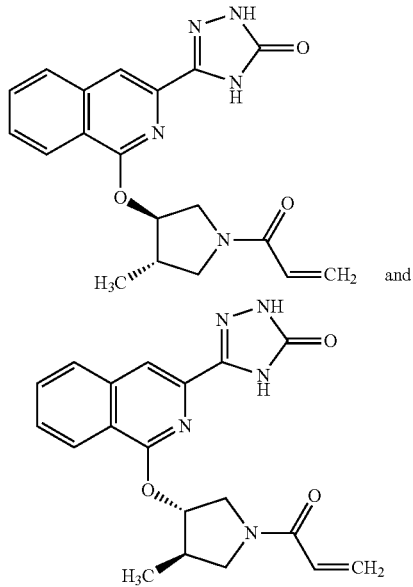

STEP A: tert-butyl trans-3-((3-chloroisoquinolin-1-yl)oxy)-4-methylpyrrolidine-1-carboxylate

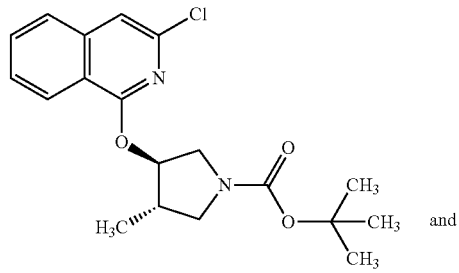

-continued

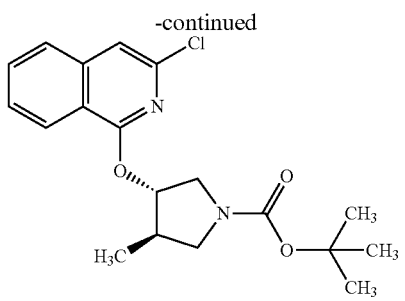

To a 25 mL microwave vial was added N-methyl-2-pyrrolidinone (10.00 mL) and tert-butyl trans-3-hydroxy-4-methylpyrrolidine-1-carboxylate (1.118 g, 5.55 mmol). The mixture was cooled to 0° C. under a nitrogen atmosphere. To this mixture was added portion-wise NaH (60% suspension in mineral oil, 0.202 g, 5.05 mmol). After 5 minutes the mixture was allowed to warm to RT and was stirred for 10 minutes. Next, 1,3-dichloroisoquinoline (1 g, 5.05 mmol) was added and the reaction mixture was heated in a microwave reactor at 135° C. for 30 minutes. The reaction mixture was subsequently diluted with water (100 mL) and extracted with EtOAc (3×100 mL). The organic layers were combined, washed with brine, dried over Na$_2$SO$_4$, and concentrated onto silica. The crude product was purified by flash column chromatography (SiO$_2$) eluting with a gradient of 5-50% heptane in EtOAc to give the title compound as a white solid (1.066 g, 58.2%). $^1$H NMR (500 MHz, CDCl$_3$) δ ppm 1.16 (d, 3 H), 1.48 (s, 9 H), 2.60 (br s, 1 H), 3.23 (br s, 1 H), 3.49 (br s, 1 H), 3.74 (br s, 1 H), 3.94 (br s, 1 H), 5.38 (br s, 1 H), 7.23-7.32 (m, 1 H), 7.51 (ddd, 1 H), 7.61-7.71 (m, 2 H), 8.17 (d, 1 H); ESI-MS m/z [M+H]$^+$ 307.6.

STEP B: tert-butyl trans-3-((3-cyanoisoquinolin-1-yl)oxy)-4-methylpyrrolidine-1-carboxylate

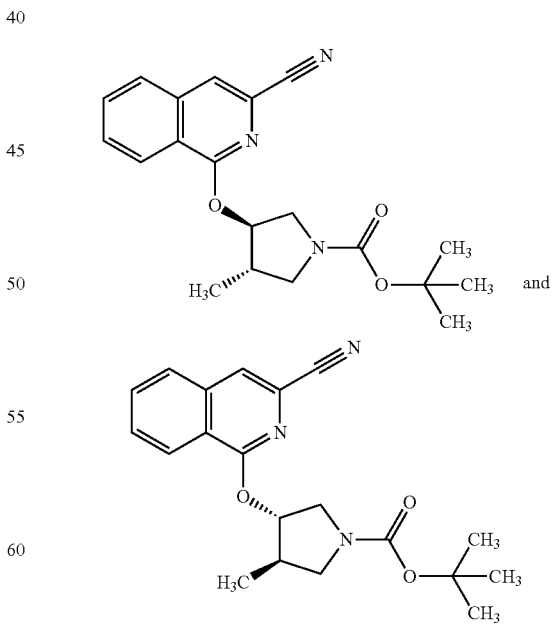

A mixture of tert-butyl trans-3-((3-chloroisoquinolin-1-yl)oxy)-4-methylpyrrolidine-1-carboxylate (1 g, 2.76 mmol), zinc cyanide (0.647 g, 5.51 mmol), Pd(PPh$_3$)$_4$ (0.318 g, 0.276 mmol) and DMF (7.83 mL) was heated in a microwave reactor at 160° C. for 20 minutes. The reaction mixture was subsequently taken up in EtOAc (100 mL), washed with brine (50 mL) and water (50 mL), dried over Na$_2$SO$_4$, and concentrated onto silica gel. The crude product was purified by flash column chromatography (SiO$_2$) eluting with a 5-50% gradient of heptane in EtOAc to give title compound as a white solid (0.796 g, 82%). $^1$H NMR (500 MHz, CDCl$_3$) δ ppm 1.17 (d, 3 H), 1.41-1.54 (m, 9 H), 2.60 (br s, 1 H), 3.26 (br s, 1 H), 3.45-3.65 (br s, 1 H), 3.74 (br s, 1 H), 3.93 (dd, 1 H), 5.40 (dt, 1 H), 7.67-7.87 (m, 4 H), 8.27 (d, 1 H); ESI-MS m/z [M+H-tert-butyl]$^+$ 298.6.

STEP C: tert-butyl trans-3-methyl-4-((3-(5-oxo-4,5-dihydro-1H-1,2,4-triazol-3-yl)isoquinolin-1-yl)oxy)pyrrolidine-1-carboxylate

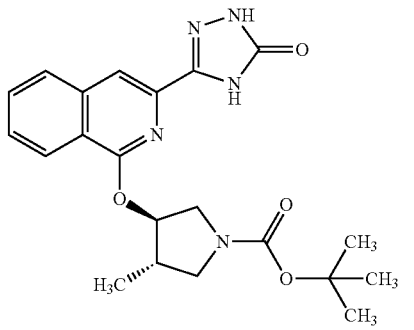

and

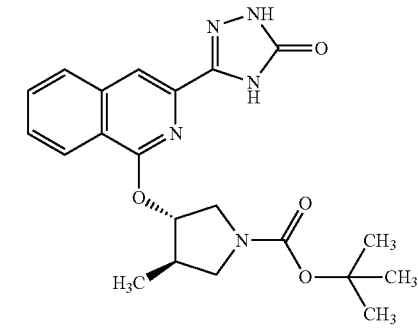

A mixture of tert-butyl trans-3-((3-cyanoisoquinolin-1-yl)oxy)-4-methylpyrrolidine-1-carboxylate (790 mg, 2.235 mmol), ethyl hydrazinecarboxylate (1164 mg, 11.18 mmol) and DBU (168 μL, 1.118 mmol) in N-methyl-2-pyrrolidinone (5.6 mL) and under a nitrogen atmosphere was heated at 170° C. in a sealed vial for 16 hours. The reaction mixture was allowed to cool to RT and was poured onto ice water, forming a pale yellow precipitate. After the ice melted (total volume was 100 mL) the solid was filtered and dried to give the title compound as a pale yellow solid (647 mg, 70.3%). $^1$H NMR (500 MHz, DMSO-d$_6$) δ ppm 1.12 (d, 3 H), 1.40 (d, 9 H), 3.11 (d, 1 H), 3.70 (dd, 2H), 3.86-4.04 (m, 2 H), 5.70-5.80 (1H, m), 7.68 (t, 1 H), 7.81 (t, 1 H), 7.98 (s, 1H), 8.02 (d, 1 H), 8.18 (d, 1 H), 11.79 (s, 1 H), 12.03 (d, 1 H); ESI-MS m/z [M+H-Boc]$^+$ 312.7.

STEP D: 3-(1-((trans-4-methylpyrrolidin-3-yl)oxy)isoquinolin-3-yl)-1H-1,2,4-triazol-5(4H)-one

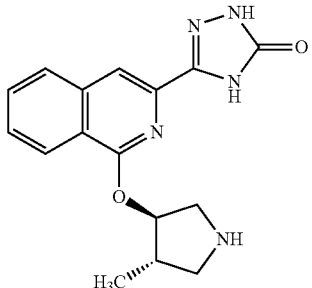

and

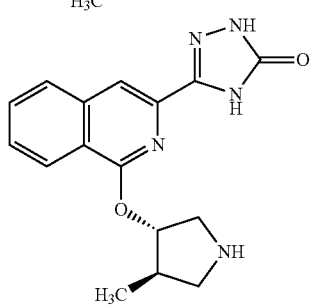

A mixture of tert-butyl trans-3-methyl-4-((3-(5-oxo-4,5-dihydro-1H-1,2,4-triazol-3-yl)isoquinolin-1-yl)oxy)pyrrolidine-1-carboxylate (0.640 g, 1.555 mmol) and HCl in 1,4-dioxane (3.8 mL, 15.55 mmol) was stirred for 30 minutes, forming a mustard colored precipitate. The precipitate was filtered, washed with diethyl ether, and dried to give an HCl salt of the title compound (0.550 g, quantitative yield). $^1$H NMR (500 MHz, DMSO-d$_6$) δ ppm 1.19 (d, 3 H), 2.68-2.74 (m, 1 H), 3.03 (dd, 1 H), 3.27-3.60 (m, 3 H), 3.86 (dd, 1 H), 5.73-5.85 (m, 1 H), 7.69 (t, 1 H), 7.78-7.90 (m, 1 H), 8.02 (s, 1 H), 8.04 (d, 1H), 8.21-8.30 (m, 1 H), 9.48 (br s, 1 H), 9.67 (br s, 1 H), 11.8 (s, 0.5H), 12.01 (s, 0.5H); ESI-MS m/z [M+H]$^+$ 312.6.

STEP E: 3-(1-(((3R,4S)-1-acryloyl-4-methylpyrrolidin-3-yl)oxy)isoquinolin-3-yl)-1H-1,2,4-triazol-5(4H)-one and 3-(1-(((3S,4R)-1-acryloyl-4-methylpyrrolidin-3-yl)oxy)isoquinolin-3-yl)-1H-1,2,4-triazol-5(4H)-one (mixture of enantiomers)

A suspension of 3-(1-((trans-4-methylpyrrolidin-3-yl)oxy)isoquinolin-3-yl)-1H-1,2,4-triazol-5(4H)-one, HCl (0.55 g, 1.58 mmol) and 2,6-dimethylpyridine (0.37 mL, 3.16 mmol) in DCM (13 mL) was cooled to 0° C. Acryloyl chloride (0.26 mL, 3.16 mmol) was added and the reaction mixture was stirred for 10 minutes, forming a pale yellow precipitate. The reaction was quenched with aqueous NaHCO$_3$ (15 mL) and the mixture was filtered. The precipitate was collected, washed with DCM (2×5 mL) and water (2×5 mL) and dried to give the title compounds (a mixture of enantiomers) as a white solid (300 mg, 52%). $^1$H NMR (500 MHz, DMSO-d$_6$) δ ppm 1.15 (d, J=6.83 Hz, 3 H), 2.53-2.65 (m, 1 H), 3.25-3.45 (1H, m), 3.55 (ddd, 1 H), 3.81-4.03 (m, 1 H), 4.20 (1H, ddd), 5.65 (ddd, 1 H), 5.73-5.88 (m, 1 H), 6.15 (ddd, J=16.84, 9.76, 2.20 Hz, 1 H), 6.60 (1H, ddd), 7.67 (td, J=7.32, 3.42 Hz, 1 H), 7.81 (t, J=7.57 Hz, 1 H), 7.93-8.08 (m, 2 H), 8.19 (d, J=8.30 Hz, 1 H), 11.79 (br s, 1 H), 12.03 (br s, 1 H); ESI-MS m/z [M+H]$^+$ 366.

Example 20

3-(1-(((3R,4S)-1-acryloyl-4-methylpyrrolidin-3-yl)oxy)isoquinolin-3-yl)-1H-1,2,4-triazol-5(4H)-one

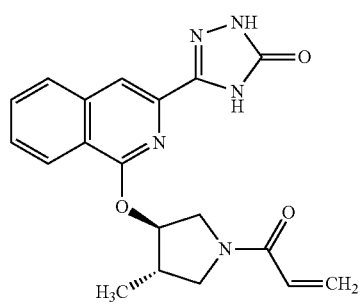 [SMILES: C=CC(=O)N1C[C@H](Oc2nc(-c3n[nH]c(=O)[nH]3)cc3ccccc23)[C@@H](C)C1]

The enantiomers of EXAMPLE 19 were separated using chiral supercritical fluid chromatography (SFC) eluting with $CO_2$, IPA, and 0.1% diethyl amine. During the SFC separation a diethylamine adduct was formed in a 1:1 ratio with title compound. Further purification via preparative HPLC gave the title compound as a white solid (22 mg). $^1$H NMR (500 MHz, DMSO-$d_6$) δ ppm 1.10 (d, 3 H), 2.45-2.58 (m, 1 H), 3.20 (dd, 1 H), 3.54 (dd, 1 H), 3.76 (dd, 1 H), 3.89-4.08 (m, 1 H), 5.51-5.67 (m, 1 H), 5.67-5.78 (m, 1 H), 6.08 (ddd, 1 H), 6.50 (dd, 1 H), 7.60 (td, 1 H), 7.74 (t, 1 H), 7.88-8.01 (m, 2 H), 8.12 (d, 1 H), 11.73 (s, 1 H), 11.96 (d, 1 H); ESI-MS m/z [M+H]$^+$ 366.6.

Example 21

3-(1-(((3S,4R)-1-acryloyl-4-methylpyrrolidin-3-yl)oxy)isoquinolin-3-yl)-1H-1,2,4-triazol-5(4H)-one

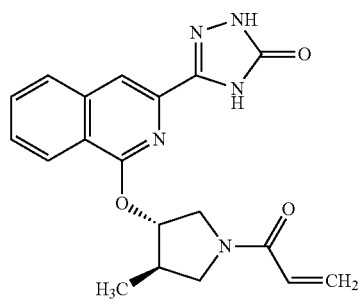 [SMILES: C=CC(=O)N1C[C@@H](C)[C@H](Oc2nc(-c3n[nH]c(=O)[nH]3)cc3ccccc23)C1]

The enantiomers of EXAMPLE 19 were separated using chiral SFC eluting with $CO_2$, IPA, and 0.1% diethyl amine. During the SFC separation a diethylamine adduct was formed in a 1:1 ratio with title compound. Further purification via preparative HPLC gave the title compound as a white solid (24 mg). $^1$H NMR (500 MHz, DMSO-$d_6$) δ ppm 1.08 (3H, d), 2.55-2.65 (m, 1 H), 3.20 (dd, 1 H), 3.54 (dd, 1 H), 3.76 (dd, 1 H), 3.89-4.08 (m, 1 H), 5.54-5.76 (m, 2 H), 6.09 (ddd, 1 H), 6.50 (dd, 1 H), 7.60 (td, 1 H), 7.74 (t, 1 H), 7.87-8.01 (m, 2 H), 8.12 (d, 1 H), 11.73 (s, 1 H), 11.96 (d, 1 H); ESI-MS m/z [M+H]$^+$ 366.6.

Example 22

(S)-3-(1-((1-acryloylpyrrolidin-3-yl)oxy)-8-fluoroisoquinolin-3-yl)-1H-1,2,4-triazol-5(4H)-one

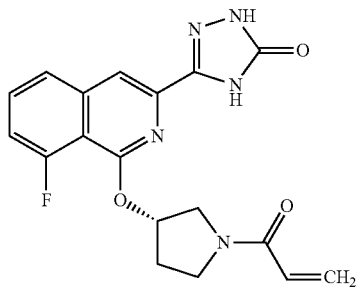 [SMILES: C=CC(=O)N1CC[C@H](Oc2nc(-c3n[nH]c(=O)[nH]3)cc3cccc(F)c23)C1]

STEP A: (S)-tert-butyl 3-((3-cyano-8-fluoroisoquinolin-1-yl)oxy)pyrrolidine-1-carboxylate

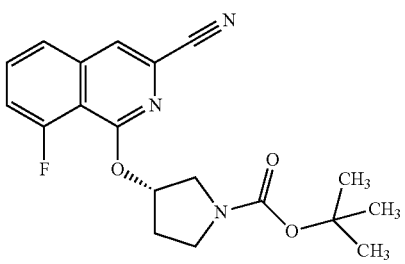 [SMILES: CC(C)(C)OC(=O)N1CC[C@H](Oc2nc(C#N)cc3cccc(F)c23)C1]

To a solution of (S)-tert-butyl 3-hydroxypyrrolidine-1-carboxylate (2.18 g, 12 mmol) in THF (50 mL) was added NaH (0.464 g, 12 mmol) at 0° C. The mixture was stirred at RT for 30 minutes. Next, 1-chloro-8-fluoroisoquinoline-3-carbonitrile (1.6 g, 8 mmol) was added and the reaction mixture was warmed to RT and stirred for 4 hours. The reaction was subsequently quenched with $H_2O$ (20 mL) and the mixture was extracted with EtOAc (3×50 mL). The organic layers were combined and concentrated in vacuo. The crude product was purified by preparative HPLC to give the title compound (1 g, 60%). $^1$H NMR (400 MHz, CDCl$_3$) δ ppm 7.72 (s, 2H), 7.61-7.59 (d, J=8 Hz, 1H), 7.38-7.32 (t, J=12 Hz, 1H), 5.8 (s, 1H), 3.75-3.59 (m, 4H), 2.29-2.28 (d, J=4 Hz, 2H).

STEP B: (S)-tert-butyl 3-((8-fluoro-3-(hydrazinyl(imino)methyl)isoquinolin-1-yl)oxy)pyrrolidine-1-carboxylate

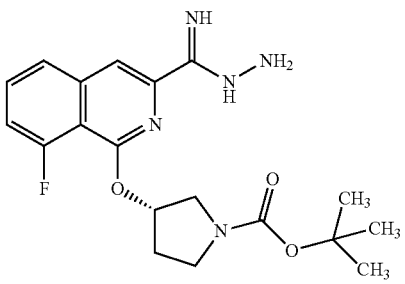

To a mixture of (S)-tert-butyl 3-((3-cyano-8-fluoroisoquinolin-1-yl)oxy)pyrrolidine-1-carboxylate (600 mg, 1.61 mmol) in MeOH (15 mL) was added NH$_2$NH$_2$.H$_2$O (10 mL) and the resulting mixture was heated to reflux for 2 hours. The solvent was removed in vacuo to afford the title compound as a white solid, which was used without further purification (500 mg).

STEP C: (S)-tert-butyl 3-((8-fluoro-3-(5-oxo-4,5-dihydro-1H-1,2,4-triazol-3-yl)isoquinolin-1-yl)oxy)pyrrolidine-1-carboxylate

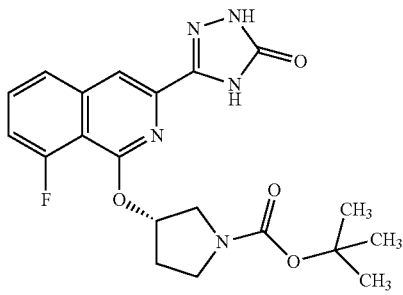

To a mixture of (S)-tert-butyl 3-((8-fluoro-3-(hydrazinyl(imino)methyl)isoquinolin-1-yl)oxy)pyrrolidine-1-carboxylate (500 mg, 1.12 mmol) in dioxane (10 mL) was added CDI (362 mg, 2.24 mmol) and the resulting mixture was heated to reflux for 2 hours. The reaction mixture was concentrated in vacuo to give crude product, which was purified by preparative HPLC to give the title compound (220 mg, 47.4%). ESI-MS m/z [M+H-Boc]$^+$ 316.

STEP D: (S)-3-(8-fluoro-1-(pyrrolidin-3-yloxy)isoquinolin-3-yl)-1H-1,2,4-triazol-5(4H)-one

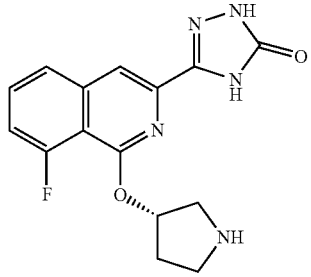

A solution of (S)-tert-butyl 3-((8-fluoro-3-(5-oxo-4,5-dihydro-1H-1,2,4-triazol-3-yl)isoquinolin-1-yl)oxy)pyrrolidine-1-carboxylate (90 mg, 0.224 mmol) in HCl/EtOAc (4M, 10 mL) was stirred at RT for 2 hours. The mixture was subsequently concentrated in vacuo to give an HCl salt of title compound (80 mg, 100%).

STEP E: (S)-3-(1-((1-acryloylpyrrolidin-3-yl)oxy)-8-fluoroisoquinolin-3-yl)-1H-1,2,4-triazol-5(4H)-one To a mixture of (S)-3-(8-fluoro-1-(pyrrolidin-3-yloxy)isoquinolin-3-yl)-1H-1,2,4-triazol-5(4H)-one hydrochloride (80 mg, 0.22 mmol) in DCM (5 mL) was added 2,6-dimethylpyridine (70 mg, 0.6 mmol). The mixture was cooled to −40° C. Acryloyl chloride (25 mg, 0.28 mmol) was added and the reaction mixture was warmed to 0° C. over a 30 minute period. The reaction was quenched with MeOH (5 mL) and the mixture concentrated in vacuo. The crude product was purified by preparative HPLC to give the title compound (43 mg, 54%). $^1$H NMR (400 MHz, DMSO-d$_6$) δ ppm 12.07 (s, 1H), 11.88 (s, 1H), 8.01 (s, 1H), 7.85-7.83 (d, J=8 Hz, 1H), 7.78-7.76 (t, J=4 Hz, 1H), 7.39 (m, 1H), 6.67-6.64 (m, 1H), 6.19-6.14 (m, 2H), 5.72-5.66 (m, 1H), 4.06 (m, 0.5H), 3.85-3.58 (m, 3.5H), 2.29-2.25 (m, 2H).

Example 23

(S)-3-(1-((1-acryloylpyrrolidin-3-yl)amino)-8-fluoroisoquinolin-3-yl)-1H-1,2,4-triazol-5(4H)-one

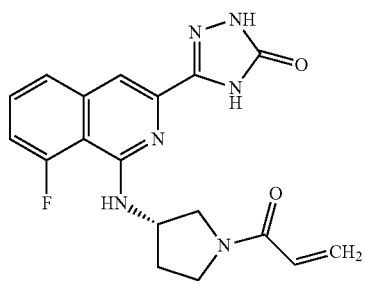 [SMILES: C=CC(=O)N1CC[C@H](Nc2nc(-c3n[nH]c(=O)[nH]3)cc3cccc(F)c23)C1]

STEP A: (S)-tert-butyl 3-((3-cyano-8-fluoroisoquinolin-1-yl)amino)pyrrolidine-1-carboxylate

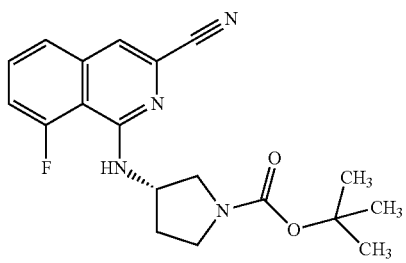

To a suspension of 1-chloro-8-fluoroisoquinoline-3-carbonitrile (0.8 g, 3.88 mmol) and Et$_3$N (0.78 g, 7.76 mmol) in NMP (5 mL) was added (S)-tert-butyl 3-aminopyrrolidine-1-carboxylate (0.87 g, 4.66 mmol) at RT. The resulting mixture was heated at 160° C. for 30 minutes in a microwave reactor. The reaction was quenched with water and the mixture was extracted with EtOAc (3×30 mL). The organic phase was dried over Na$_2$SO$_4$ and concentrated in vacuo. The crude product was purified by column chromatography eluting with ethyl acetate and petroleum ether (EtOAc/PE=1:50-1:9 gradient) on silica gel to give the title compound (1.12 g, 81%). $^1$H NMR (400 MHz, CDCl$_3$) δ ppm 7.56-7.52 (m, 1H), 7.44-7.42 (d, 1H, J=8.0 Hz), 7.29 (s, 1H), 7.21-7.18 (m, 1H), 6.47-6.43 (m, 1H), 4.73 (br s, 1H), 3.77-3.72 (dd, J$_1$=6.4 Hz, J$_2$=11.6 Hz, 1H), 3.48-3.19 (m, 3H), 2.26 (br s, 1H), 1.90 (br s, 1H), 1.41 (s, 9H); ESI-MS m/z [M+H-tert-butyl]$^+$ 301.2.

STEP B: (S)-tert-butyl 3-((8-fluoro-3-(5-oxo-4,5-dihydro-1H-1,2,4-triazol-3-yl)isoquinolin-1-yl)amino)pyrrolidine-1-carboxylate

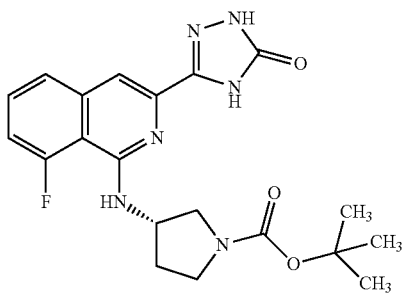 [SMILES: CC(C)(C)OC(=O)N1CC[C@H](Nc2nc(-c3n[nH]c(=O)[nH]3)cc3cccc(F)c23)C1]

To a mixture of (S)-tert-butyl 3-((3-cyano-8-fluoroisoquinolin-1-yl)amino)pyrrolidine-1-carboxylate (1.0 g, 2.81 mmol), ethyl hydrazinecarboxylate (7.74 g, 74.40 mmol) and 2,3,4,5,7,8,9,10-octahydropyrido[1,2-a][1,3]diazepine (1.13 g, 7.44 mmol) was added a catalytic amount of NaH (10 mg, 0.25 mmol). The reaction mixture was heated to 170° C. for 30 minutes. The crude product was purified by preparative HPLC to give the title compound as pale yellow solid (300 mg, 25.7%). ESI-MS m/z [M+H]+ 415.2.

STEP C: (S)-3-(8-fluoro-1-(pyrrolidin-3-ylamino)isoquinolin-3-yl)-1H-1,2,4-triazol-5(4H)-one

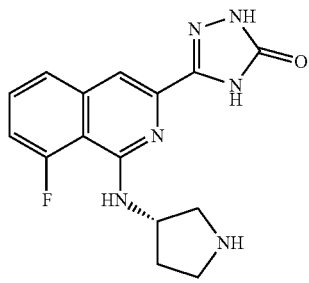 [SMILES: O=c1[nH]nc(-c2cc3cccc(F)c3c(N[C@H]3CCNC3)n2)[nH]1]

To a mixture of (S)-tert-butyl 3-((8-fluoro-3-(5-oxo-4,5-dihydro-1H-1,2,4-triazol-3-yl)isoquinolin-1-yl)amino)pyrrolidine-1-carboxylate (300 mg, 0.72 mmol) in EtOAc (5 mL) was added a 4M solution of HCl in EtOAc (5 mL). The reaction mixture was stirred at RT for 45 minutes. The solvent was removed in vacuo to give an HCl salt of the title compound (250 mg, 99.2%). ESI-MS m/z [M+H]+ 315.2.

STEP D: (S)-3-(1-((1-acryloylpyrrolidin-3-yl)amino)-8-fluoroisoquinolin-3-yl)-1H-1,2,4-triazol-5(4H)-one To a mixture of (S)-3-(8-fluoro-1-(pyrrolidin-3-ylamino)isoquinolin-3-yl)-1H-1,2,4-triazol-5(4H)-one hydrochloride (250 mg, 0.71 mmol) in DCM (15 mL) was added a solution of 2,6-dimethylpyridine (192 mg, 1.8 mmol) in DCM (1 mL). Acryloyl chloride (135 mg, 1.5 mmol) in DCM (1.35 mL) was added dropwise via syringe at −78° C. The reaction mixture was stirred at −78° C. for 30 minutes. Additional 2,6-dimethylpyridine (32 mg, 0.3 mmol) in DCM (0.32 mL) was added followed by acryloyl chloride (45 mg, 0.50 mmol) in DCM (0.45 mL). The reaction mixture was stirred at −10° C. for 20 minutes. The reaction was quenched with MeOH (1 mL) and the mixture was concentrated under vacuum. The crude product was purified by preparative HPLC to give the title compound as a white solid (40.58 mg, 15.5%). 1H NMR (400 MHz, DMSO-d6) δ ppm 11.91 (s, 1H), 11.78 (s, 1H), 7.69-7.63 (m, 3H), 7.60-7.58 (m, 1H), 6.61-6.55 (m, 2H), 6.18-6.13 (m, 1H), 5.67-5.64 (m, 1H), 5.30-5.10 (m, 1H), 4.17-4.15 (m, 1H), 3.66-3.63 (m, 2H), 3.28-3.25 (m, 1H), 2.25-2.03 (m, 2H); ESI-MS m/z [M+H]+ 369.1.

Example 24

(S)-3-(1-((1-acryloylpyrrolidin-3-yl)oxy)-7-chloroisoquinolin-3-yl)-1H-1,2,4-triazol-5(4H)-one

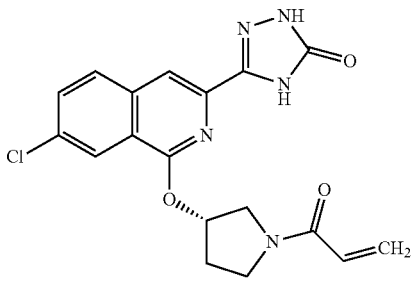 [SMILES: C=CC(=O)N1CC[C@H](Oc2nc(-c3n[nH]c(=O)[nH]3)cc3ccc(Cl)cc23)C1]

STEP A: (S)-tert-butyl 3-((7-chloro-3-cyanoisoquinolin-1-yl)oxy)pyrrolidine-1-carboxylate

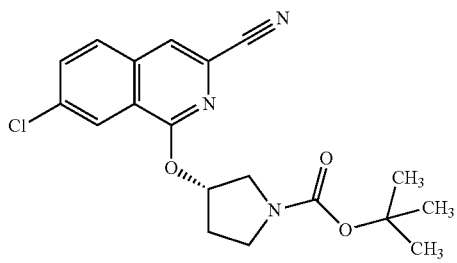 [SMILES: CC(C)(C)OC(=O)N1CC[C@H](Oc2nc(C#N)cc3ccc(Cl)cc23)C1]

To a solution of (S)-tert-butyl 3-hydroxypyrrolidine-1-carboxylate (201 mg, 1.076 mmol) in THF (5 mL) at 0° C. was added NaH (81 mg, 1.35 mmol). The reaction mixture was stirred at RT for 30 minutes. Next, 1,7-dichloroisoquinoline-3-carbonitrile (200 mg, 0.897 mmol) was added and the reaction mixture was warmed to RT over a 1 hour period. The reaction was quenched with saturated aqueous NH4Cl (10 mL) and the resulting mixture was extracted with EtOAc (3×50 mL). The organic layers were combined, washed with brine, dried over Na2SO4, and concentrated. The crude product was purified by preparative TLC eluting with petroleum ether and ethyl acetate (PE/EtOAc=3:1) to give the title compound (200 mg, 59%). 1H NMR (400 MHz, CDCl3) δ ppm 8.15 (s, 1H), 7.65-7.71 (m, 3H), 5.74 (br, 1H), 3.46-3.69 (m, 4H), 2.23 (s, 1H), 1.49 (s, 9H).

STEP B: (S)-tert-butyl 3-((7-chloro-3-(hydrazinyl(imino)methyl)isoquinolin-1-yl)oxy)pyrrolidine-1-carboxylate

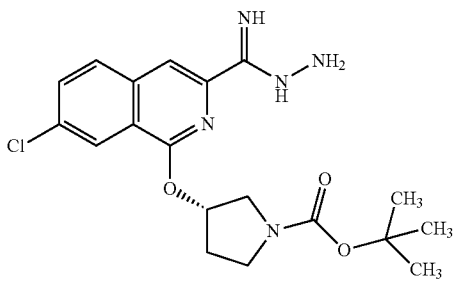 [SMILES: CC(C)(C)OC(=O)N1CC[C@H](Oc2nc(C(=N)NN)cc3ccc(Cl)cc23)C1]

To a mixture of (S)-tert-butyl 3-((7-chloro-3-cyanoisoquinolin-1-yl)oxy)pyrrolidine-1-carboxylate (300 mg, 1.61 mmol) in MeOH (4 mL) was added NH$_2$NH$_2$.H$_2$O (5 mL). The resulting mixture was heated to reflux for 2 hours. The solvents were removed in vacuo to give the title compound, which was used without further purification. ESI-MS m/z [M+H]$^+$ 406.1.

STEP C: (S)-tert-butyl 3-((7-chloro-3-(5-oxo-4,5-dihydro-1H-1,2,4-triazol-3-yl)isoquinolin-1-yl)oxy)pyrrolidine-1-carboxylate

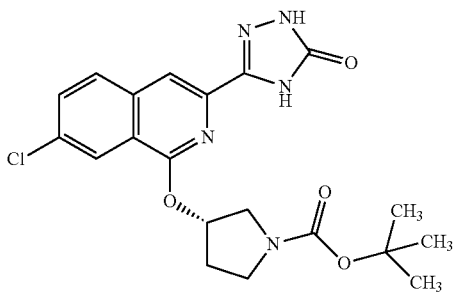 [SMILES: CC(C)(C)OC(=O)N1CC[C@H](Oc2nc(-c3n[nH]c(=O)[nH]3)cc3ccc(Cl)cc23)C1]

To a mixture of (S)-tert-butyl 3-((7-chloro-3-(hydrazinyl(imino)methyl)isoquinolin-1-yl)oxy)pyrrolidine-1-carboxylate (350 mg, 0.862 mmol) in dioxane (8 mL) was added CDI (210 mg, 1.293 mmol). The reaction mixture was heated to reflux for 2 hours and was subsequently concentrated in vacuo. The crude product was purified by preparative HPLC to give the title compound (200 mg, 57%).

STEP D: (S)-3-(7-chloro-1-(pyrrolidin-3-yloxy)isoquinolin-3-yl)-1H-1,2,4-triazol-5(4H)-one

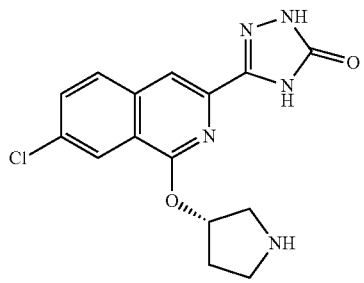 [SMILES: O=c1[nH]nc(-c2cc3ccc(Cl)cc3c(O[C@H]3CCNC3)n2)[nH]1]

A solution of (S)-tert-butyl 3-((7-chloro-3-(5-oxo-4,5-dihydro-1H-1,2,4-triazol-3-yl)isoquinolin-1-yl)oxy)pyrrolidine-1-carboxylate (200 mg, 0.463 mmol) in 4M HCl/EtOAc (5 mL) was stirred at RT for 2 hours. The reaction mixture was subsequently concentrated in vacuo to give the title compound (180 mg, 100%).

STEP E: (S)-3-(1-((1-acryloylpyrrolidin-3-yl)oxy)-7-chloroisoquinolin-3-yl)-1H-1,2,4-triazol-5(4H)-one To a mixture of (S)-3-(7-chloro-1-(pyrrolidin-3-yloxy)isoquinolin-3-yl)-1H-1,2,4-triazol-5(4H)-one (180 mg, 0.489 mmol) in DCM (10 mL) was added 2,6-dimethylpyridine (157 mg, 1.467 mmol) at −20° C. followed by the dropwise addition of acryloyl chloride (88 mg, 0.978 mmol, 10 mg/mL in dry DCM). The reaction mixture was warmed to 0° C. over a 30 minute period. The reaction was quenched with MeOH (5 mL) and the mixture concentrated in vacuo. The crude product was purified by preparative HPLC to give the title compound (35 mg, 18%). $^1$H NMR (400 MHz, DMSO-d$_6$) δ ppm 12.06 (br, 1H), 11.84 (s, 1H), 8.16 (s, 1H), 8.09 (dd, J=1.8 Hz and 8.9 Hz, 1H), 8.03 (s, 1H), 7.83-7.86 (m, 1H), 6.55-6.72 (m, 1H), 6.12-6.19 (m, 2H), 5.63-5.72 (m, 1H), 4.65-4.12 (m, 4H), 2.25-2.42 (m, 2H).

Example 25

(S)-3-(1-((1-acryloylpyrrolidin-3-yl)amino)-7-fluoroisoquinolin-3-yl)-1H-1,2,4-triazol-5(4H)-one

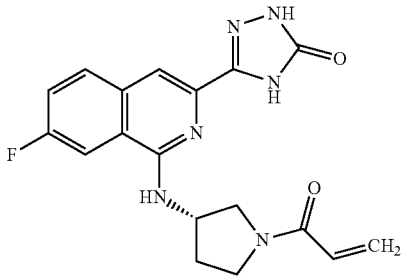 [SMILES: C=CC(=O)N1CC[C@H](Nc2nc(-c3n[nH]c(=O)[nH]3)cc3ccc(F)cc23)C1]

STEP A: (S)-tert-butyl 3-((3-chloro-7-fluoroisoquinolin-1-yl)amino)pyrrolidine-1-carboxylate

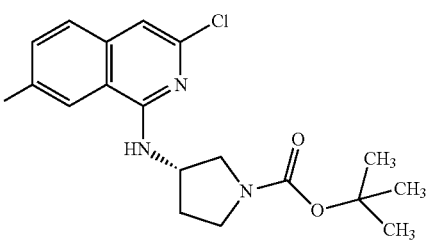

To a solution of 1,3-dichloro-7-fluoroisoquinoline (1 g, 4.6 mmol) in NMP (15 mL) was added (S)-tert-butyl 3-aminopyrrolidine-1-carboxylate (1.72 g, 9.3 mmol) and Et$_3$N (1.4 g, 14 mmol). The reaction mixture was heated at 160° C. for 2 hours. The mixture was subsequently partition between H$_2$O (20 mL) and EtOAc (20 mL). The aqueous phase was extracted with EtOAc (3×20 mL). The organic layers were combined, dried over Na₂SO₄, and concentrated. The crude product was purified by column chromatography eluting with petroleum ether and ethyl acetate (PE/EA=10:1-5:1 gradient) to give the title compound (1.2 g, 70%). ¹H NMR (400 MHz, DMSO-d₆) δ ppm 8.26-8.23 (d, J=10.8 Hz,1H), 7.82-7.80 (dd, J₁=8.8 Hz, J₂=5.2 Hz, 1H), 7.68-7.67 (d, J=5.6 Hz 1H), 7.63-7.60 (t, J=8.8 Hz,1H), 7.10 (s, 1H), 4.63-4.53 (m, 1H), 3.70-3.66 (m, 1H), 3.48-3.45 (m, 1H), 3.29-3.26 (m, 1H), 2.23-2.18 (m, 1H), 2.03-1.97 (m, 1H), 1.40 (s,9H).

STEP B: (S)-tert-butyl 3-((3-cyano-7-fluoroisoquinolin-1-yl)amino)pyrrolidine-1-carboxylate

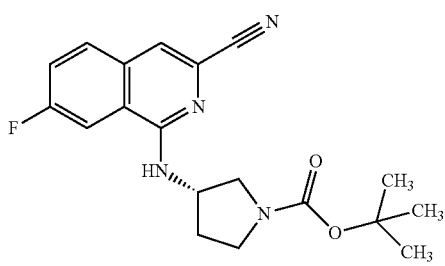 [SMILES: CC(C)(C)OC(=O)N1CC[C@H](Nc2nc(C#N)cc3ccc(F)cc23)C1]

To a solution of (S)-tert-butyl 3-((3-chloro-7-fluoroisoquinolin-1-yl)amino)pyrrolidine-1-carboxylate (0.5 g, 1.37 mmol) in DMF (15 mL) was added Zn(CN)₂ (0.48 g, 4.1 mmol), and Pd(PPh₃)₄(0.16 g, 0.14 mmol) under a nitrogen atmosphere. The mixture was heated to 160° C. for 30 minutes in a microwave reactor. The mixture was partition between EtOAc (50 mL) and water (50 mL). The aqueous layer was extracted with EtOAc (3×50 mL). The organic layers were combined, washed with saturated aqueous NaCl (3×50 mL) and concentrated in vacuo. The crude product was purified by column chromatography eluting with petroleum ether and ethyl acetate (PE/EtOAc=10:1-5:1 gradient) to give the title compound (0.36 g, 72%). ¹H NMR (400 MHz, DMSO-d₆) δ ppm 8.38-8.35 (d, J=10.8 Hz, 1H), 8.01-7.97 (m, 1H), 7.77-7.72 (m, 3H), 4.66-4.58 (m, 1H), 3.69-3.67 (m, 1H), 3.48-3.46 (m, 1H), 3.39-3.37 (m, 1H), 3.28-3.27 (m, 1H), 2.2 (s, 1H), 1.97-1.91 (m, 1H), 1.40 (s, 9H).

STEP C: (S)-tert-butyl 3-((7-fluoro-3-(hydrazinyl (imino)methyl)isoquinolin-1-yl)amino)pyrrolidine-1-carboxylate

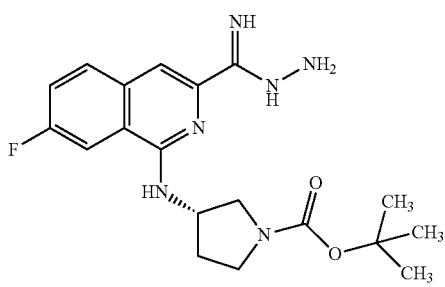 [SMILES: CC(C)(C)OC(=O)N1CC[C@H](Nc2nc(C(=N)NN)cc3ccc(F)cc23)C1]

To a mixture of (S)-tert-butyl 3-((3-cyano-7-fluoroisoquinolin-1-yl)amino)pyrrolidine-1-carboxylate (350 mg, 1 mmol) in MeOH (10 mL) was added NH₂NH₂.H₂O (10 mL). The reaction mixture was heated to reflux for 2 hours. The solvent was removed to give the title compound as white solid, which was used without further purification (350 mg, 92%). ESI-MS m/z [M+H]⁺ 389.2.

STEP D: (S)-tert-butyl 3-((7-fluoro-3-(5-oxo-4,5-dihydro-1H-1,2,4-triazol-3-yl)isoquinolin-1-yl) amino)pyrrolidine-1-carboxylate

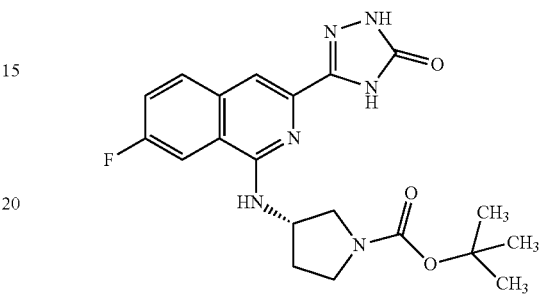

To a solution of (S)-tert-butyl 3-((7-fluoro-3-(hydrazinyl (imino)methyl)isoquinolin-1-yl)amino)pyrrolidine-1-carboxylate (0.35 g, 1 mmol) in dioxane (10 mL) was added CDI (0.36 g, 2 mmol) under a nitrogen atmosphere. The mixture was heated to reflux for 2 hours and was subsequently concentrated in vacuo. The crude product was purified by preparative HPLC to give the title compound (120 mg, 34%). ESI-MS m/z [M+H]⁺ 415.2.

STEP E: (S)-3-(7-fluoro-1-(pyrrolidin-3-ylamino) isoquinolin-3-yl)-1H-1,2,4-triazol-5(4H)-one

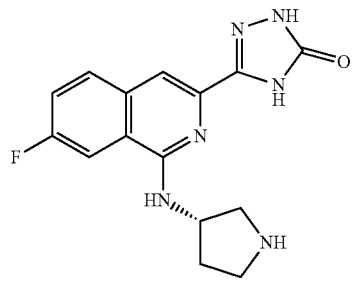 [SMILES: O=c1[nH]nc(-c2cc3ccc(F)cc3c(N[C@H]3CCNC3)n2)[nH]1]

A solution of (S)-tert-butyl 3-((7-fluoro-3-(5-oxo-4,5-dihydro-1H-1,2,4-triazol-3-yl)isoquinolin-1-yl)amino)pyrrolidine-1-carboxylate (120 mg, 0.29 mmol) in 4M HCl/EtOAc (10 mL) was stirred at RT for 30 minutes. The reaction mixture was concentrated in vacuo to give the title compound, which was used without further purification (100 mg, 100%). ESI-MS m/z [M+H]⁺ 315.2.

STEP F: (S)-3-(1-((1-acryloylpyrrolidin-3-yl) amino)-7-fluoroisoquinolin-3-yl)-1H-1,2,4-triazol-5 (4H)-one To a mixture of (S)-3-(7-fluoro-1-(pyrrolidin-3-ylamino) isoquinolin-3-yl)-1H-1,2,4-triazol-5(4H)-one (100 mg, 0.35 mmol) in DCM (10 mL) was added 2,6-dimethylpyridine (122 mg, 1.15 mmol). The resulting mixture was cooled to −40° C. Acryloyl chloride (45 mg, 0.49 mmol) was added dropwise and the reaction mixture was stirred at −40° C. for 30 minutes. The reaction was quenched with MeOH (5 mL) and the mixture concentrated in vacuo. The crude product was purified by preparative HPLC to give the title compound (79 mg, 75%). $^1$H NMR (400 MHz, DMSO-d$_6$) δ ppm 11.84 (s, 1H), 11.70 (s, 1H), 8.25-8.22 (d, J=10.8 Hz, 1H), 7.97-7.96 (m, 1H), 7.63-7.60 (m, 2H), 7.55-7.54 (m, 1H), 6.59-6.57 (m, 1H), 6.21-6.15 (m, 1H), 5.68-5.65 (dd, J$_1$=10.4 Hz, J$_2$=2.4 Hz, 1H), 5.20-5.18 (m, 1H), 4.19-4.15 (m, 0.5H), 3.70-3.67 (m, 2H), 3.69-3.45 (m, 1.5H), 3.25 (m, 0.5H), 2.26-2.24 (m, 1H), 2.08-2.03 (m, 1H).

Example 26

(S)-3-(1-((1-acryloylpyrrolidin-3-yl)amino)-7-chloroisoquinolin-3-yl)-1H-1,2,4-triazol-5 (4H)-one

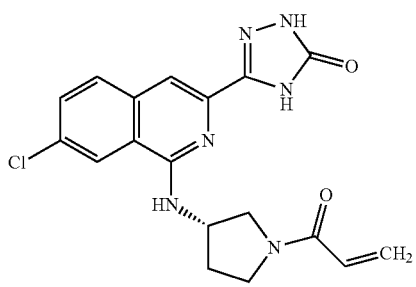 [SMILES: C=CC(=O)N1CC[C@H](Nc2nc(-c3n[nH]c(=O)[nH]3)cc3ccc(Cl)cc23)C1]

STEP A: (S)-tert-butyl 3-((7-chloro-3-cyanoisoquinolin-1-yl)amino)pyrrolidine-1-carboxylate

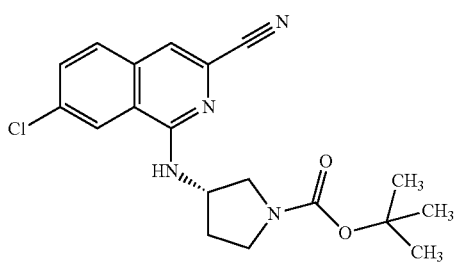

To a solution of 1,7-dichloroisoquinoline-3-carbonitrile (500 mg, 2.24 mmol) in NMP (5 mL) was added (S)-tert-butyl 3-aminopyrrolidine-1-carboxylate (460 mg, 2.46 mmol) and Et$_3$N (453 mg, 4.48 mmol). The solution was heated to 160° C. for 30 minutes in a microwave reactor. The reaction was quenched with H$_2$O (20 mL) and extracted with EtOAc (3×10 mL). The organic layers were combined and concentrated in vacuo. The crude product was purified by column chromatography eluting with ethyl acetate and petroleum ether (EtOAc/PE=1:10 to 1:5 gradient) to give the title compound (660 mg, 79%). ESI-MS m/z [M+H-tert-butyl]$^+$ 317.

STEP B: (S)-tert-butyl 3-((7-chloro-3-(hydrazinyl(imino)methyl)isoquinolin-1-yl)amino)pyrrolidine-1-carboxylate

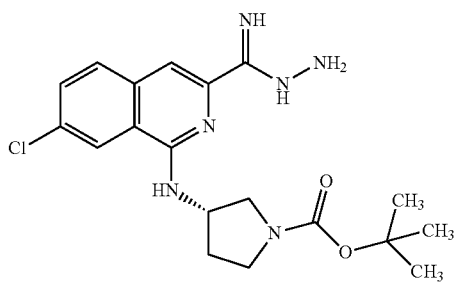

To a mixture of (S)-tert-butyl 3-((7-chloro-3-cyanoisoquinolin-1-yl)amino)pyrrolidine-1-carboxylate (660 mg, 1.77 mmol) in MeOH (5 mL) was added NH$_2$NH$_2$.H$_2$O (5 mL) and the resulting mixture was heated to reflux for 2 hours. The solvent was subsequently removed to give the title compound as a yellow solid, which was used without further purification (710 mg). ESI-MS m/z [M+H]$^+$ 405.

STEP C: (S)-tert-butyl 3-((7-chloro-3-(5-oxo-4,5-dihydro-1H-1,2,4-triazol-3-yl)isoquinolin-1-yl)amino)pyrrolidine-1-carboxylate

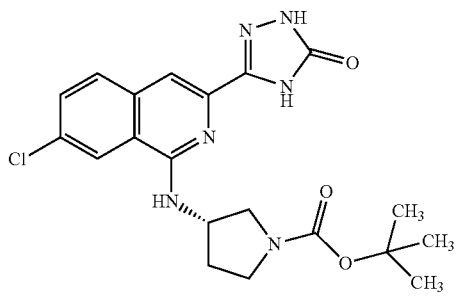 [SMILES: CC(C)(C)OC(=O)N1CC[C@H](Nc2nc(-c3n[nH]c(=O)[nH]3)cc3ccc(Cl)cc23)C1]

To a mixture of (S)-tert-butyl 3-((7-chloro-3-(hydrazinyl(imino)methyl)isoquinolin-1-yl)amino)pyrrolidine-1-carboxylate (710 mg) in dioxane (10 mL) was added CDI (42.6 mg, 2.63 mmol). The resulting mixture was heated to reflux for 2 hours. The reaction mixture was concentrated in vacuo. The crude product was purified by preparative HPLC to give the title compound (130 mg, 17% over 2 steps). ESI-MS m/z [M+H]$^+$ 431.

STEP D: (S)-3-(7-chloro-1-(pyrrolidin-3-ylamino)isoquinolin-3-yl)-1H-1,2,4-triazol-5(4H)-one

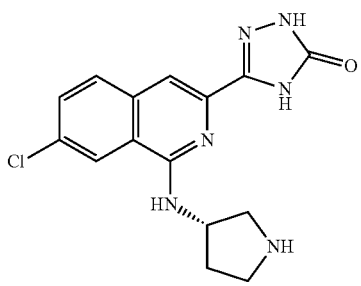 [SMILES: O=c1[nH]nc(-c2cc3ccc(Cl)cc3c(N[C@H]3CCNC3)n2)[nH]1]

A solution of (S)-tert-butyl 3-((7-chloro-3-(5-oxo-4,5-dihydro-1H-1,2,4-triazol-3-yl)isoquinolin-1-yl)amino)pyrrolidine-1-carboxylate (130 mg, 0.30 mmol) in 4M HCl/EtOAc(4 mL) was stirred at RT for 50 minutes. The reaction mixture was subsequently concentrated in vacuo to give an HCl salt of the title compound (120 mg). ESI-MS m/z [M+H]$^+$ 331.

STEP E: (S)-3-(1-((1-acryloylpyrrolidin-3-yl)amino)-7-chloroisoquinolin-3-yl)-1H-1,2,4-triazol-5(4H)-one To a mixture of (S)-3-(7-chloro-1-(pyrrolidin-3-ylamino)isoquinolin-3-yl)-1H-1,2,4-triazol-5(4H)-one hydrochloride (120 mg) in DCM (8 mL) was added 2,6-dimethylpyridine (105 mg, 0.978 mmol). The resulting mixture was cooled to −78° C. and acryloyl chloride (48 mg, 0.530 mmol, 10 mg/mL in dry DCM) was added dropwise. The reaction mixture was stirred at −78° C. for 30 minutes. The reaction was quenched with MeOH (5 mL) and the mixture was concentrated in vacuo. The crude product was purified by preparative HPLC to give the title compound (22 mg, 18% over 2 steps). $^1$H NMR (400 MHz, DMSO-d$_6$) δ ppm 11.87 (s, 1H), 11.72 (s, 1H), 8.51 (S, 1H), 7.88 (m, 1H), 7.60-7.70 (m, 2H), 7.56 (d, 1H, J=4.0 Hz), 6.55-6.57 (m, 1H), 6.13-6.19 (m, 1H), 5.63-5.70 (m, 1H), 5.17-5.18 (m, 1H), 3.65-4.17 (m, 4H), 2.01-2.37 (m, 2H); ESI-MS m/z [M+H]$^+$ 385.

Example 27

(S)-3-(1-((1-acryloylpyrrolidin-3-yl)oxy)-8-chloroisoquinolin-3-yl)-1H-1,2,4-triazol-5(4H)-one

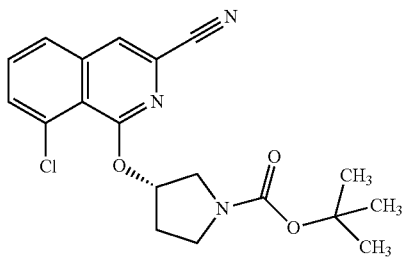

STEP A: (S)-tert-butyl 3-((8-chloro-3-cyanoisoquinolin-1-yl)oxy)pyrrolidine-1-carboxylate

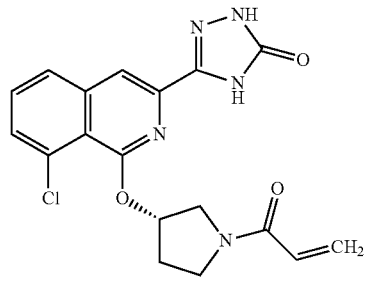 [SMILES: C=CC(=O)N1CC[C@H](Oc2nc(-c3n[nH]c(=O)[nH]3)cc3cccc(Cl)c23)C1]

To a solution of (S)-tert-butyl 3-hydroxypyrrolidine-1-carboxylate (126 mg, 0.674 mmol) in THF (5 mL) was added NaH (26.8 mg, 0.677 mmol) at 0° C. The mixture was stirred for 30 minutes. Next, 1,8-dichloroisoquinoline-3-carbonitrile was added and the reaction mixture was warmed to RT for 4 hours. The reaction was quenched with H$_2$O (2 mL) and the mixture was extracted with EtOAc (3×10 mL). The organic layers were combined and concentrated in vacuo. The crude product was purified by preparative TLC to give the title compound (120 mg, 73.2%).

STEP B: (S)-tert-butyl 3-((8-chloro-3-(hydrazinyl(imino)methyl)isoquinolin-1-yl)oxy)pyrrolidine-1-carboxylate

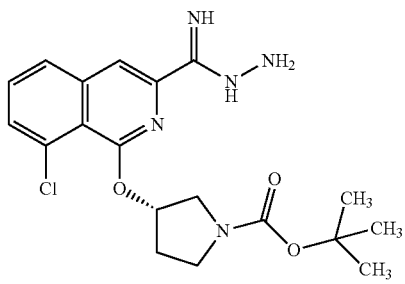

To (S)-tert-butyl 3-((8-chloro-3-cyanoisoquinolin-1-yl)oxy)pyrrolidine-1-carboxylate (120 mg, 0.32 mmol) in MeOH (50 mL) was added NH$_2$NH$_2$.H$_2$O (5 mL). The resulting mixture was heated to reflux for 2 hours and then cooled and concentrated in vacuo to give the title compound as a yellow solid, which was used without further purification (130.3 mg, 100%). ESI-MS m/z [M+H]$^+$ 406.2.

STEP C: (S)-tert-butyl 3-((8-chloro-3-(5-oxo-4,5-dihydro-1H-1,2,4-triazol-3-yl)isoquinolin-1-yl)oxy)pyrrolidine-1-carboxylate

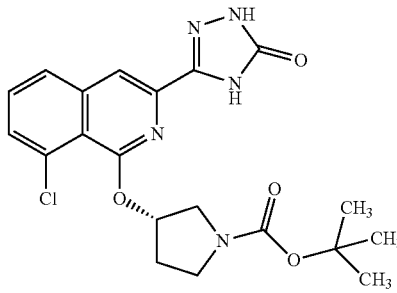

To (S)-tert-butyl 3-((8-chloro-3-(hydrazinyl(imino)methyl)isoquinolin-1-yl)oxy)pyrrolidine-1-carboxylate (130 mg, 1.61 mmol) in dioxane (10 mL) was added CDI (78 mg, 0.48 mmol). The resulting mixture was heated to reflux for 2 hours and was then cooled and concentrated in vacuo. The crude product was purified by preparative HPLC to give the title compound (50 mg, 35%). ESI-MS m/z [M+H-Boc]$^+$ 332.2.

STEP D: (S)-3-(8-chloro-1-(pyrrolidin-3-yloxy) isoquinolin-3-yl)-1H-1,2,4-triazol-5(4H)-one

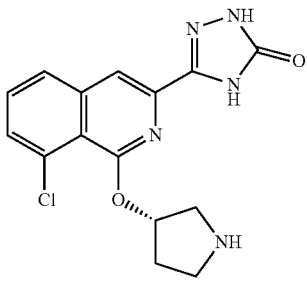 [SMILES: O=c1[nH]nc(-c2cc3cccc(Cl)c3c(O[C@H]3CCNC3)n2)[nH]1]

A solution of (S)-tert-butyl 3-((8-chloro-3-(5-oxo-4,5-dihydro-1H-1,2,4-triazol-3-yl)isoquinolin-1-yl)oxy)pyrrolidine-1-carboxylate (50 mg, 0.116 mmol) in HCl/EtOAc (10 mL) was stirred at RT for 2 hours. The reaction mixture was subsequently concentrated in vacuo to give an HCl salt of the title compound (42.6 mg). ESI-MS m/z [M+H]$^+$ 332.2.

STEP E: (S)-3-(1-((1-acryloylpyrrolidin-3-yl)oxy)-8-chloroisoquinolin-3-yl)-1H-1,2,4-triazol-5(4H)-one To (S)-3-(8-chloro-1-(pyrrolidin-3-yloxy)isoquinolin-3-yl)-1H-1,2,4-triazol-5(4H)-one hydrochloride (42.6 mg, 0.116 mmol) in DCM (25 mL) was added 2,6-dimethylpyridine (37.24 mg, 0.35 mmol). The resulting mixture was cooled to −20° C. Acryloyl chloride (26.1 mg, 0.29 mmol, 10 mg/mL in dry DCM) was added dropwise and the reaction mixture was warmed to 0° C. for 30 minutes. The reaction was quenched with MeOH (5 mL) and the mixture was concentrated in vacuo. The crude product was purified by preparative HPLC to give the title compound (22.02 mg, 49.25%). $^1$H NMR (400 MHz, DMSO-d$_6$) δ ppm 12.09 (s, 1H), 11.87 (s, 1H), 8.01-7.98 (m, 2H), 7.71-7.70 (d, J=4.0 Hz, 2H), 6.67-6.57 (m, 1H), 6.26-6.14 (m, 2H), 5.72-5.63 (m, 1H), 4.01-3.71 (m, 4H), 2.33-2.24 (m, 2H); ESI-MS m/z [M+H]$^+$ 386.1.

Example 28

(S)-3-(1-((1-acryloylpyrrolidin-3-yl)amino)-8-chloroisoquinolin-3-yl)-1H-1,2,4-triazol-5(4H)-one

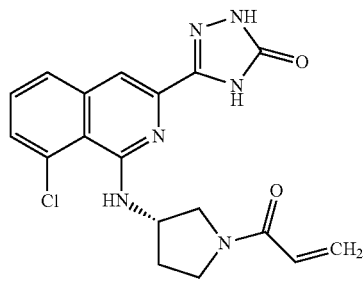

STEP A: (S)-tert-butyl 3-((8-chloro-3-cyanoisoquinolin-1-yl)amino)pyrrolidine-1-carboxylate

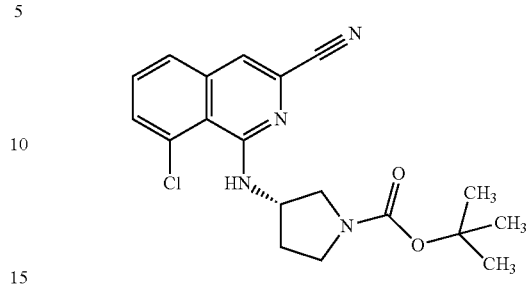

To a suspension of 1,8-dichloroisoquinoline-3-carbonitrile (0.3 g, 1.35 mmol) and Et$_3$N (0.27 g, 2.7 mmol) in NMP (5 mL) was added (S)-tert-butyl 3-aminopyrrolidine-1-carboxylate (0.3 g, 1.62 mmol) at RT. The resulting mixture was stirred at 160° C. for 30 minutes in a microwave reactor. The reaction was subsequently quenched with water and the mixture was extracted with EtOAc (3×30 mL). The organic phase was dried over Na$_2$SO$_4$ and concentrated in vacuo. The crude product was purified by column chromatography eluting with ethyl acetate and petroleum ether (EtOAc/PE=1:10-1:2 gradient) on silica gel to give the title compound (0.45 g, 85%). $^1$H NMR (400 MHz, DMSO-d$_6$) δ ppm 7.92-7.90 (d, J=8.0 Hz, 1H), 7.85-7.83 (m, 2H), 7.79-7.77 (d, J=8.0 Hz, 1H), 7.63 (s, 1H), 4.66-4.58 (m, 1H), 3.75-3.72 (t, J=8.0 Hz, 3H), 3.52-3.35 (m, 3H), 2.31-2.30 (br s, 1H), 2.11-2.07 (br s, 1H), 1.47-1.45 (s, 9H).

STEP B: (S)-tert-butyl 3-((8-chloro-3-(hydrazinyl(imino)methyl)isoquinolin-1-yl)amino)pyrrolidine-1-carboxylate

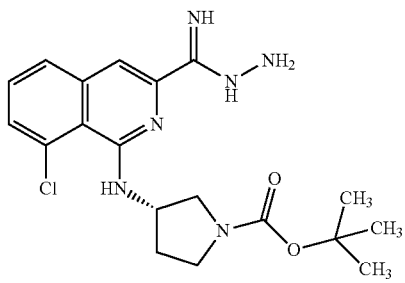 [SMILES: CC(C)(C)OC(=O)N1CC[C@H](Nc2nc(C(=N)NN)cc3cccc(Cl)c23)C1]

To a mixture of (S)-tert-butyl 3-((8-chloro-3-cyanoisoquinolin-1-yl)amino)pyrrolidine-1-carboxylate (450 mg, 1.21 mmol) in MeOH (5 mL) was added NH$_2$NH$_2$.H$_2$O (5 mL). The resulting mixture was heated to reflux for 2 hours and the solvent was subsequently removed to give the title compound as a yellow solid, which was used without further purification (450 mg, 91%). ESI-MS m/z [M+H]$^+$ 405.2.

STEP C: (S)-tert-butyl 3-((8-chloro-3-(5-oxo-4,5-dihydro-1H-1,2,4-triazol-3-yl)isoquinolin-1-yl)amino)pyrrolidine-1-carboxylate

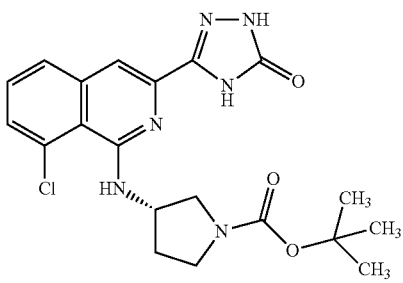 [SMILES: CC(C)(C)OC(=O)N1CC[C@H](Nc2nc(-c3n[nH]c(=O)[nH]3)cc3cccc(Cl)c23)C1]

To a mixture of (S)-tert-butyl 3-((8-chloro-3-(hydrazinyl(imino)methyl)isoquinolin-1-yl)amino)pyrrolidine-1-carboxylate (450 mg, 1.1 mmol) in dioxane (10 mL) was added CDI (360 mg, 2.2 mmol). The resulting mixture was heated to reflux for 2 hours and was subsequently concentrated in vacuo. The crude product was purified by preparative HPLC to give the title compound (170 mg, 45%). ESI-MS m/z [M+H]+ 431.1.

STEP D: (S)-3-(8-chloro-1-(pyrrolidin-3-ylamino)isoquinolin-3-yl)-1H-1,2,4-triazol-5(4H)-one hydrochloride

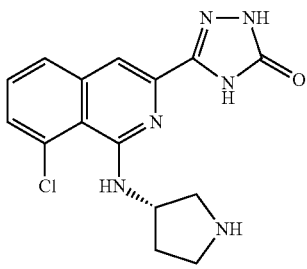 [SMILES: O=c1[nH]nc(-c2cc3cccc(Cl)c3c(N[C@H]3CCNC3)n2)[nH]1]

A solution of (S)-tert-butyl 3-((8-chloro-3-(5-oxo-4,5-dihydro-1H-1,2,4-triazol-3-yl)isoquinolin-1-yl)amino)pyrrolidine-1-carboxylate (170 mg, 0.52 mmol) in HCl/EtOAc (10 mL) was stirred at RT for 2 hours. The reaction mixture was subsequently concentrated in vacuo to give an HCl salt of the title compound (160 mg, 100%). $^1$H NMR (400 MHz, DMSO-$d_6$) δ ppm 11.90 (s, 1H), 11.85 (s, 1H), 9.134 (s, 2H), 7.86-7.84 (dd, $J_1$=2.8 Hz, $J_2$=6.8 Hz, 1H), 7.64-7.62 (m, 3H), 7.57-7.56 (d, J=6.4 Hz, 1H), 5.0 (s, 1H), 3.65-3.60 (m, 1H), 3.24-3.21 (m, 2H), 2.40-2.36 (m, 1H), 2.11-2.07 (m, 1H).

STEP E: (S)-3-(1-((1-acryloylpyrrolidin-3-yl)amino)-8-chloroisoquinolin-3-yl)-1H-1,2,4-triazol-5(4H)-one To a mixture of (S)-3-(8-chloro-1-(pyrrolidin-3-ylamino)isoquinolin-3-yl)-1H-1,2,4-triazol-5(4H)-one hydrochloride (100 mg, 0.3 mmol) in DCM (20 mL) was added 2,6-dimethylpyridine (97 mg, 0.91 mmol). The resulting mixture was cooled to −40° C. Acryloyl chloride (51 mg, 0.6 mmol, 10 mg/mL in dry DCM) was added dropwise and the mixture was stirred at −40° C. for 30 minutes. The reaction was subsequently quenched with MeOH (5 mL) and the mixture was concentrated in vacuo. The crude product was purified by preparative HPLC to give the title compound (57 mg, 52%). $^1$H NMR (400 MHz, DMSO-$d_6$) δ ppm 11.91 (s, 1H), 11.80 (s, 1H), 7.85-7.83 (m, 1H), 7.61-7.59 (m, 3H), 7.49-7.47 (m, 1H), 6.6-6.5 (m, 1H), 6.17-6.13 (m, 1H), 5.67-5.63 (m, 1H), 5.18-5.16 (m, 1H), 4.18-4.17 (m, 0.5H), 3.69-3.65 (m, 0.5H), 3.42 (m, 0.5H), 3.32-3.31 (m, 1.5H), 2.31-2.29 (m, 1H), 2.04-2.01 (m, 1H); ESI-MS m/z [M+H]+ 385.1.

Example 29

(S)-3-(1-((1-acryloylpyrrolidin-3-yl)amino)-8-methoxyisoquinolin-3-yl)-1H-1,2,4-triazol-5(4H)-one

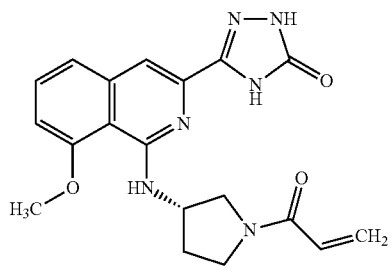 [SMILES: C=CC(=O)N1CC[C@H](Nc2nc(-c3n[nH]c(=O)[nH]3)cc3cccc(OC)c23)C1]

STEP A: (S)-tert-butyl 3-((3-cyano-8-methoxyisoquinolin-1-yl)amino)pyrrolidine-1-carboxylate

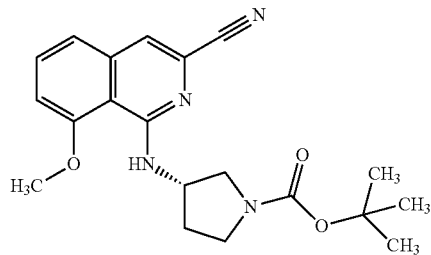 [SMILES: COc1cccc2cc(C#N)nc(N[C@H]3CCN(C(=O)OC(C)(C)C)C3)c12]

To a solution of 1-chloro-8-methoxyisoquinoline-3-carbonitrile (230 mg, 1.05 mmol) in NMP (5 mL) was added (S)-tert-butyl 3-aminopyrrolidine-1-carboxylate (294 mg, 1.57 mmol) and Et$_3$N (212 mg, 2.1 mmol). The reaction mixture was heated to 130° C. for 45 minutes in a microwave reactor and was subsequently quenched with H$_2$O (20 mL). The aqueous phase was extracted with EtOAc (3×10 mL). The organic layers were combined and concentrated in vacuo. The crude product was purified by column chromatography eluting with ethyl acetate and petroleum ether (EtOAc/PE=1:20-1:2 gradient) to give the title compound (380 mg, 2 batches, 52%). $^1$H NMR (400 MHz, CDCl$_3$) δ ppm 7.85 (s, 1H), 7.55 (t, 1H, J=8.0 Hz), 7.25 (s, 1H), 6.97 (d, 1H, J=8.0 Hz), 4.60-4.80 (m, 1H), 4.01 (s, 3H), 3.78-3.79 (m, 1H), 3.27-3.57 (m, 3H), 2.29-2.34 (m, 1H), 1.94-1.99 (m, 1H), 1.48 (s, 9H).

STEP B: (S)-tert-butyl 3-((3-(hydrazinyl(imino)methyl)-8-methoxyisoquinolin-1-yl)amino)pyrrolidine-1-carboxylate

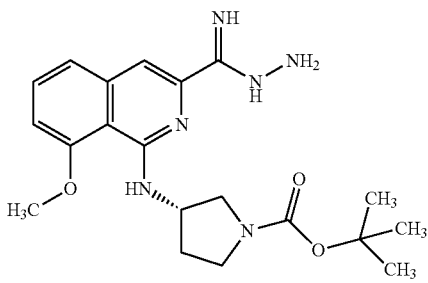 [SMILES: COc1cccc2cc(C(=N)NN)nc(N[C@H]3CCN(C(=O)OC(C)(C)C)C3)c12]

To a mixture of (S)-tert-butyl 3-((3-cyano-8-methoxyisoquinolin-1-yl)amino)pyrrolidine-1-carboxylate (380 mg, 1.03 mmol) in MeOH (5 mL) was added NH$_2$NH$_2$.H$_2$O (5 mL). The resulting mixture was heated to reflux for 2 hours. The solvent was removed to give the title compound as a yellow solid, which was used without further purification (660 mg). ESI-MS m/z [M+H]$^+$ 401.

STEP C: (S)-tert-butyl 3-((8-methoxy-3-(5-oxo-4,5-dihydro-1H-1,2,4-triazol-3-yl)isoquinolin-1-yl)amino)pyrrolidine-1-carboxylate

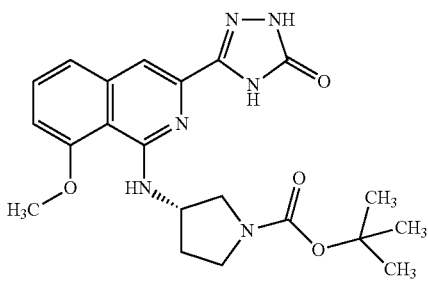 [SMILES: COc1cccc2cc(-c3n[nH]c(=O)[nH]3)nc(N[C@H]3CCN(C(=O)OC(C)(C)C)C3)c12]

To a mixture of (S)-tert-butyl 3-((3-(hydrazinyl(imino)methyl)-8-methoxyisoquinolin-1-yl)amino)pyrrolidine-1-carboxylate (400 mg, 1.0 mmol) in dioxane (10 mL) was added CDI (245 mg, 1.5 mmol). The resulting mixture was heated to reflux for 2 hours and then concentrated in vacuo. The crude product was purified by preparative HPLC to give the title compound (80 mg, 18% over 2 steps). ESI-MS m/z [M+H]$^+$ 427.

STEP D: (S)-3-(8-methoxy-1-(pyrrolidin-3-ylamino)isoquinolin-3-yl)-1H-1,2,4-triazol-5(4H)-one

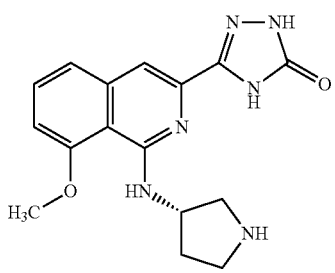 [SMILES: COc1cccc2cc(-c3n[nH]c(=O)[nH]3)nc(N[C@H]3CCNC3)c12]

A solution of (S)-tert-butyl 3-((8-methoxy-3-(5-oxo-4,5-dihydro-1H-1,2,4-triazol-3-yl)isoquinolin-1-yl)amino)pyrrolidine-1-carboxylate (80 mg, 0.187 mmol) in HCl/EtOAc (5 mL) was stirred at RT for 1 hour. The reaction mixture was subsequently concentrated in vacuo to give an HCl salt of the title compound, which was used without further purification (120 mg). ESI-MS m/z [M+H]$^+$ 327.

STEP E: (S)-3-(1-((1-acryloylpyrrolidin-3-yl)amino)-8-methoxyisoquinolin-3-yl)-1H-1,2,4-triazol-5(4H)-one To a mixture of (S)-3-(8-methoxy-1-(pyrrolidin-3-ylamino)isoquinolin-3-yl)-1H-1,2,4-triazol-5(4H)-one hydrochloride (120 mg, 0.33 mmol) in DCM (8 mL) was added 2,6-dimethylpyridine (106 mg, 0.99 mmol). The resulting mixture was cooled to −78° C. Acryloyl chloride (120 mg, 1.20 mmol, 10 mg/mL in dry DCM) was added dropwise and the reaction mixture was stirred at −78° C. for 1.5 hours. The reaction was quenched with MeOH (5 mL) and the mixture was concentrated in vacuo. The crude product was purified by preparative HPLC to give the title compound (34 mg, 27%). $^1$H NMR (400 MHz, DMSO-d$_6$) δ ppm 11.81 (s, 1H), 11.69 (s, 1H), 7.85 (dd, 14.5 Hz, 1H), 7.57-7.51 (m, 1H), 7.43 (d, J=3.3 Hz, 1H), 7.36 (d, J=8.0 Hz, 1H), 7.02 (d, J=8.0 Hz, 1H), 6.72-6.54 (m, 1H), 6.16 (m, 1H), 5.73-5.61 (m, 1H), 5.21-5.03 (m, 1H), 4.16 (m, 1H), 4.04-3.89 (m, 3H), 3.79 (m, 1H), 3.71-3.61 (m, 1H), 3.44 (m, 1H), 3.24 (m, 1H), 2.42-2.21 (m, 1H), 2.09-1.90 (m, 1H); ESI-MS m/z [M+H]$^+$ 381.

Example 30

(S)-3-(6-((1-acryloylpyrrolidin-3-yl)oxy)-4-methylpyridin-2-yl)-1H-1,2,4-triazol-5(4H)-one

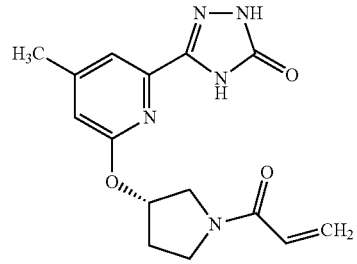 [SMILES: C=CC(=O)N1CC[C@H](Oc2cc(C)cc(-c3n[nH]c(=O)[nH]3)n2)C1]

STEP A: 2-cyano-4-methylpyridine-1-oxide

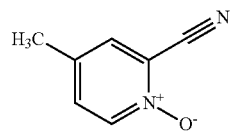

A solution of 4-methylpicolinonitrile (5 g, 42.3 mmol) in DCM (25 mL) was cooled in an ice/brine bath. To this solution was added mCPBA (14.61 g, 85 mmol). The reaction mixture was allowed to warm to RT and was stirred overnight. The mixture was subsequently diluted with DCM until all solids were dissolved and was washed with 1N NaOH (2×200 mL) and with brine. The organic phase was dried over MgSO$_4$, filtered, and concentrated in vacuo to give the title compound as a white solid (4.03 g, 71%). ESI-MS m/z [M+H]$^+$ 135.1.

STEP B: 6-chloro-4-methylpicolinonitrile

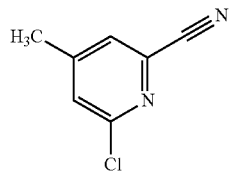

A mixture of 2-cyano-4-methylpyridine-1-oxide (4.03 g, 30 mmol) in phosphoryl trichloride (80 mL, 858 mmol) was heated to reflux overnight. The solvent was removed in vacuo. The residue was treated with ice and its pH made basic using saturated NaOH solution at 0° C. The aqueous layer was extracted with DCM (3×). The organic layers were combined, dried over MgSO$_4$, filtered, and evaporated in vacuo to give the title compound (3.7 g, 81%). ESI-MS m/z [M+H]$^+$ 153.6.

STEP C: 3-(6-chloro-4-methylpyridin-2-yl)-1H-1,2,4-triazol-5(4H)-one

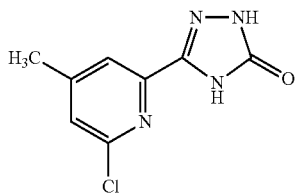

A mixture of 6-chloro-4-methylpicolinonitrile (3 g, 19.66 mmol) and ethyl hydrazinecarboxylate (8.19 g, 79 mmol) in NMP (6 mL) was heated in a sealed tube at 160° C. overnight. The residue was purified by column chromatography eluting with a gradient of 0-80% EtOAc in heptanes. The product-containing fractions were collected and evaporated in vacuo to give the title compound as a yellow semi-solid (428 mg). ESI-MS m/z [M+H]$^+$ 211.6.

STEP D: (S)-tert-butyl 3-((4-methyl-6-(5-oxo-4,5-dihydro-1H-1,2,4-triazol-3-yl)pyridin-2-yl)oxy)pyrrolidine-1-carboxylate

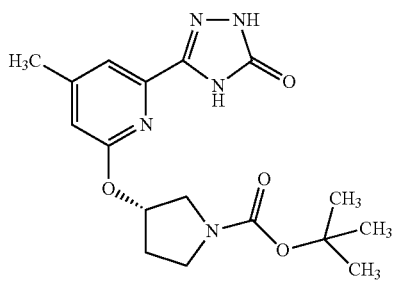 [SMILES: Cc1cc(O[C@H]2CCN(C(=O)OC(C)(C)C)C2)nc(-c2n[nH]c(=O)[nH]2)c1]

A mixture of 3-(6-chloro-4-methylpyridin-2-yl)-1H-1,2,4-triazol-5(4H)-one (428 mg, 2.032 mmol), (S)-tert-butyl 3-hydroxypyrrolidine-1-carboxylate (457 mg, 2.439 mmol) and sodium hydride (81 mg, 2.032 mmol) in N-methyl-2-pyrrolidinone (7 mL) was heated in a microwave reactor at 140° C. for 30 minutes. After cooling, water was added and the mixture was extracted with EtOAc. The aqueous layer was acidified with 1M HCl aq and extracted with EtOAc. The organic layers were combined, dried over MgSO$_4$, filtered, and evaporated in vacuo to give the title compound, which was used without further purification. ESI-MS [M+H-tert-butyl]$^+$ 306.2.

STEP E: (S)-3-(4-methyl-6-(pyrrolidin-3-yloxy)pyridin-2-yl)-1H-1,2,4-triazol-5(4H)-one

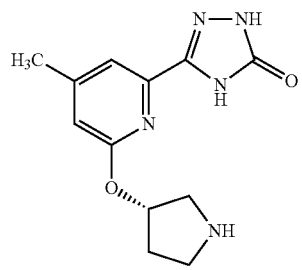 [SMILES: Cc1cc(O[C@H]2CCNC2)nc(-c2n[nH]c(=O)[nH]2)c1]

A mixture of (S)-tert-butyl 3-((4-methyl-6-(5-oxo-4,5-dihydro-1H-1,2,4-triazol-3-yl)pyridin-2-yl)oxy)pyrrolidine-1-carboxylate (700 mg, 1.937 mmol) and TFA (3 mL, 38.9 mmol) was stirred at RT for 1 hour. The solvent was removed in vacuo and the crude product purified by preparative HPLC eluting with a gradient 5-40% ACN in water (acid mode). The product-containing fractions were collected and evaporated in vacuo to give the title compound (12 mg, 2%).

STEP F: (S)-3-(6-((1-acryloylpyrrolidin-3-yl)oxy)-4-methylpyridin-2-yl)-1H-1,2,4-triazol-5(4H)-one To (S)-3-(4-methyl-6-(pyrrolidin-3-yloxy)pyridin-2-yl)-1H-1,2,4-triazol-5(4H)-one (23 mg, 0.088 mmol), which was dissolved in a minimal amount of DCM, was added 2,6-dimethylpyridine (20.44 µL, 0.176 mmol) and acryloyl chloride (9.56 mg, 0.106 mmol). The reaction mixture was stirred overnight at RT and was subsequently diluted with water and extracted with EtOAc (2×). The organic layers were combined, dried over MgSO$_4$, filtered, and evaporated in vacuo. The crude product was purified by preparative HPLC eluting with a gradient of 20-45% ACN in water (acid mode). The product-containing fractions were combined and evaporated in vacuo to give a TFA salt of the title compound (12 mg). ESI-MS m/z [M+H]$^+$ 316.3.

Example 31

(S)-3-(6-((1-acryloylpyrrolidin-3-yl)oxy)pyridin-2-yl)-1H-1,2,4-triazol-5(4H)-one

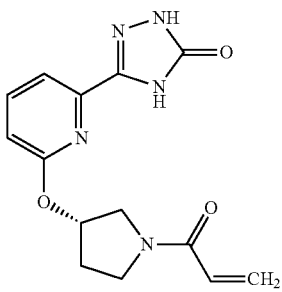 [SMILES: C=CC(=O)N1CC[C@H](Oc2cccc(-c3n[nH]c(=O)[nH]3)n2)C1]

STEP A: (S)-tert-butyl 3-((6-cyanopyridin-2-yl)oxy)pyrrolidine-1-carboxylate

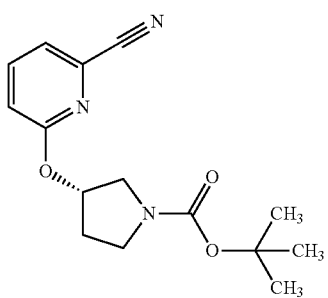 [SMILES: CC(C)(C)OC(=O)N1CC[C@H](Oc2cccc(C#N)n2)C1]

To (S)-tert-butyl 3-hydroxypyrrolidine-1-carboxylate (676 mg, 3.61 mmol) in NMP (4 mL) at 0° C. was added $Cs_2CO_3$ (1176 mg, 3.61 mmol) followed by 6-chloropicolinonitrile (500 mg, 3.61 mmol). The mixture was heated at 140° C. for 15 minutes in a microwave reactor to give the title compound. The crude product was used directly in the next step.

STEP B: (S)-tert-butyl 3-((6-(5-oxo-4,5-dihydro-1H-1,2,4-triazol-3-yl)pyridin-2-yl)oxy)pyrrolidine-1-carboxylate

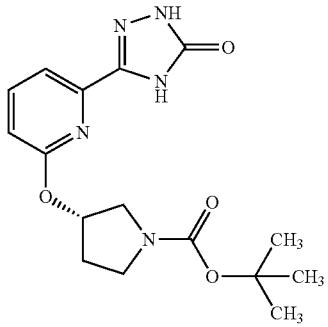 [SMILES: CC(C)(C)OC(=O)N1CC[C@H](Oc2cccc(-c3n[nH]c(=O)[nH]3)n2)C1]

To crude (S)-tert-butyl 3-((6-cyanopyridin-2-yl)oxy)pyrrolidine-1-carboxylate (1.044 g) in NMP (1.5 mL) was added ethyl hydrazinecarboxylate (0.752 g, 7.22 mmol). The reaction mixture was heated at 175° C. overnight and was subsequently cooled and diluted with EtOAc. The organic phase was washed with saturated aqueous $NH_4Cl$, dried, and concentrated to give the title compound, which was used without further purification.

STEP C: (S)-3-(6-(pyrrolidin-3-yloxy)pyridin-2-yl)-1H-1,2,4-triazol-5(4H)-one

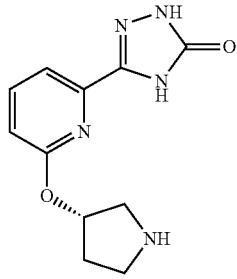 [SMILES: O=c1[nH]nc(-c2cccc(O[C@H]3CCNC3)n2)[nH]1]

Crude (S)-tert-butyl 3-((6-(5-oxo-4,5-dihydro-1H-1,2,4-triazol-3-yl)pyridin-2-yl)oxy)pyrrolidine-1-carboxylate was treated with DCM (4 mL) and TFA (2 mL) for 2 hours at RT and then concentrated. The crude product was purified by preparative HPLC eluting with a gradient of 1-25% ACN in water (acid mode) to give the title compound (125 mg, 14.0% over 3 steps).

STEP D: (S)-3-(6-((1-acryloylpyrrolidin-3-yl)oxy)pyridin-2-yl)-1H-1,2,4-triazol-5(4H)-one To a solution of (S)-3-(6-(pyrrolidin-3-yloxy)pyridin-2-yl)-1H-1,2,4-triazol-5(4H)-one (84 mg, 0.340 mmol) in DCM (10 mL) was added 2,6-dimethylpyridine (0.118 mL, 1.019 mmol) at 0° C. followed by acryloyl chloride (0.041 mL, 0.510 mmol). The mixture was stirred overnight. The reaction was subsequently quenched with water and the solvent was removed in a rotary evaporator. The crude product was purified by preparative HPLC eluting with a gradient of 20-31% ACN in water (acid mode) to give a TFA salt of the title compound (7 mg, 7%). $^1$H NMR (400 MHz, DMSO-$d_6$) (rotamers were observed) δ ppm 1.90-2.25 (m, 2 H), 3.35-3.75 (m, 3.5 H), 3.90-4.00 (m, 0.5 H), 5.75-5.90 (m, 1H), 5.60 (ddd, J=18.57, 10.36, 2.40 Hz, 1 H), 6.00-6.13 (m, 1 H), 6.43-6.64 (m, 1 H), 6.80 (dd, J=8.34, 4.55 Hz, 1 H), 7.44 (d, J=7.58 Hz, 1 H), 7.68-7.80 (m, 1 H); ESI-MS m/z [M+H]$^+$ 302.3.

Example 32

(S)-3-(6-((1-acryloylpyrrolidin-3-yl)oxy)-5-methylpyridin-2-yl)-1H-1,2,4-triazol-5(4H)-one

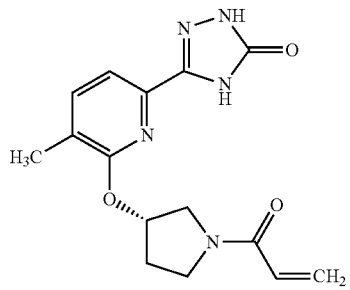 [SMILES: C=CC(=O)N1CC[C@H](Oc2nc(-c3n[nH]c(=O)[nH]3)ccc2C)C1]

STEP A: (S)-tert-butyl 3-((6-cyano-3-methylpyridin-2-yl)oxy)pyrrolidine-1-carboxylate

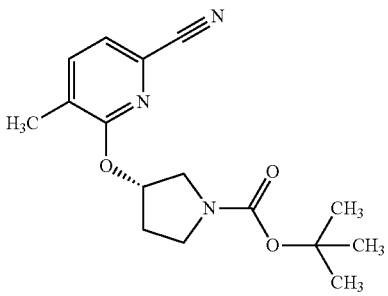 [SMILES: Cc1ccc(C#N)nc1O[C@H]1CCN(C(=O)OC(C)(C)C)C1]

To (S)-tert-butyl 3-hydroxypyrrolidine-1-carboxylate (491 mg, 2.62 mmol) in NMP (4 mL) was added $Cs_2CO_3$ (1025 mg, 3.15 mmol). The mixture was stirred at 0° C. for 1 hour at which time 6-chloro-5-methylpicolinonitrile (400 mg, 2.62 mmol) was added. The reaction mixture was heated at 140° C. for 1 hour in a microwave reactor to give the title compound in a crude reaction mixture that was used directly in the next step.

STEP B: (S)-tert-butyl 3-((3-methyl-6-(5-oxo-4,5-dihydro-1H-1,2,4-triazol-3-yl)pyridin-2-yl)oxy)pyrrolidine-1-carboxylate

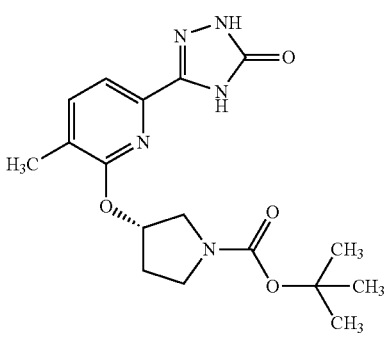 [SMILES: Cc1ccc(-c2n[nH]c(=O)[nH]2)nc1O[C@H]1CCN(C(=O)OC(C)(C)C)C1]

To the reaction mixture containing (S)-tert-butyl 3-((6-cyano-3-methylpyridin-2-yl)oxy)pyrrolidine-1-carboxylate (1.095 g) was added NMP (1.5 mL) and ethyl hydrazinecarboxylate (0.752 g, 7.22 mmol). The mixture was heated at 175° C. for 1.5 days and was subsequently cooled and diluted with EtOAc. The organic phase was washed with aqueous $NH_4Cl$, dried, and concentrated. The crude product was purified by preparative HPLC eluting with a gradient of 35-60% ACN in water (acid mode) to give the title compound (0.042 g, 4.4% over 2 steps).

STEP C: (S)-3-(5-methyl-6-(pyrrolidin-3-yloxy)pyridin-2-yl)-1H-1,2,4-triazol-5(4H)-one

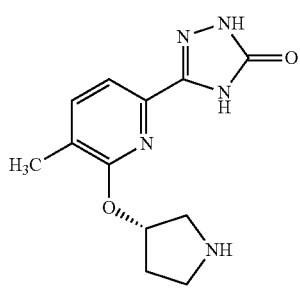 [SMILES: Cc1ccc(-c2n[nH]c(=O)[nH]2)nc1O[C@H]1CCNC1]

To a solution of (S)-tert-butyl 3-((3-methyl-6-(5-oxo-4,5-dihydro-1H-1,2,4-triazol-3-yl)pyridin-2-yl)oxy)pyrrolidine-1-carboxylate (0.042 g, 0.115 mmol) in DCM (5 mL) was added TFA (1 mL). The reaction mixture was stirred at RT overnight. The solvent was removed in vacuo and the residue was dried under high vacuum to give the title compound, which was used directly to the next step.

STEP D: (S)-3-(6-((1-acryloylpyrrolidin-3-yl)oxy)-5-methylpyridin-2-yl)-1H-1,2,4-triazol-5(4H)-one To a solution of (S)-3-(5-methyl-6-(pyrrolidin-3-yloxy)pyridin-2-yl)-1H-1,2,4-triazol-5(4H)-one (30 mg, 0.115 mmol) in DCM (10 mL) was added 2,6-dimethylpyridine (0.040 mL, 0.344 mmol) at 0° C. followed by acryloyl chloride (0.014 mL, 0.172 mmol). The mixture was stirred overnight. The reaction was quenched with water and the mixture concentrated in vacuo. The crude product was purified by preparative HPLC eluting with a gradient of 20-37% ACN in water (acid mode) to give a TFA salt of the title compound (6 mg, 17%). $^1H$ NMR (400 MHz, DMSO-$d_6$) δ ppm 2.14-2.29 (m, 1 H), 2.32 (br s, 1 H), 3.39 (s, 3 H), 3.45-3.99 (m, 4 H), 5.49-5.70 (m, 1 H), 5.74 (br s, 1 H), 6.09 (ddd, J=16.74, 8.53, 2.27 Hz, 1 H), 6.47-6.68 (m, 1 H), 7.56-7.68 (m, 1 H), 7.76 (t, J=7.58 Hz, 1 H), 7.93-8.05 (m, 1 H), 8.13 (d, J=8.34 Hz, 1 H); ESI-MS m/z [M+H]$^+$ 316.3.

Example 33

(S)-5-(1-((1-(2-chloroacetyl)pyrrolidin-3-yl)oxy)isoquinolin-3-yl)-2,4-dihydro-3H-1,2,4-triazol-3-one

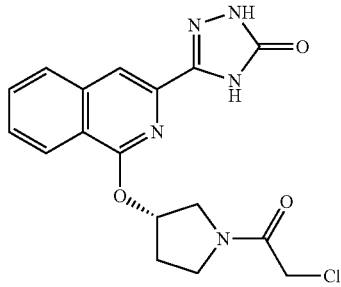 [SMILES: O=C(CCl)N1CC[C@H](Oc2nc(-c3n[nH]c(=O)[nH]3)cc3ccccc23)C1]

To a solution of (S)-3-(1-(pyrrolidin-3-yloxy)isoquinolin-3-yl)-1H-1,2,4-triazol-5(4H)-one (10 mg, 0.034 mmol) in DCM (3 mL) was added 2,6-dimethylpyridine (5.28 μL, 0.045 mmol) at 0° C. followed by 2-chloroacetyl chloride (5.06 μL, 0.064 mmol). The reaction mixture was stirred at room temperature overnight. A white solid formed, which was filtered. This solid quickly gummed up and was treated with MeOH. The resulting liquor was combined with the filtrate, passed through a membrane, and purified by mass-triggered HPLC eluting with a gradient of 25-45% ACN in water (acid mode). The product-containing fractions were concentrated to give a TFA salt of the title compound as a yellow film (5.9 mg, 35%). $^1H$ NMR (400 MHz, $CD_3OD$) δ ppm 2.35-2.57 (m, 2H), 3.71-3.99 (m, 3H), 4.12 (dd, J=12.38, 4.29 Hz, 1 H), 4.22 (s, 1 H), 4.31 (s, 1 H), 6.16 (br s, 1 H), 6.22 (br s, 1 H), 7.63-7.71 (m, 1 H), 7.76-7.84 (m, 1 H), 7.90-8.03 (m, 2 H), 8.26 (d, J=7.58 Hz, 1 H); ESI-MS m/z [M+H]$^+$ 374.4.

Example 34

(S)-5-(1-((1-(2-chloroacetyl)pyrrolidin-3-yl)amino)isoquinolin-3-yl)-2,4-dihydro-3H-1,2,4-triazol-3-one

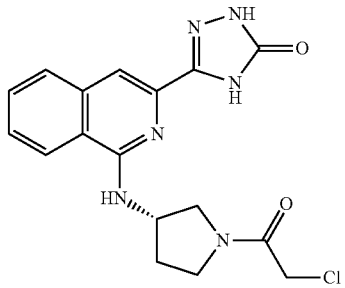 [SMILES: O=C(CCl)N1CC[C@H](Nc2nc(-c3n[nH]c(=O)[nH]3)cc3ccccc23)C1]

To a solution of (S)-3-(1-(pyrrolidin-3-ylamino)isoquinolin-3-yl)-1H-1,2,4-triazol-5(4H)-one (0.028 g, 0.093 mmol) in DCM (5 mL) was added 2,6-dimethylpyridine (0.054 mL, 0.465 mmol) at 0° C. followed by 2-chloroacetyl chloride (0.011 mL, 0.140 mmol). The reaction mixture was allowed to warm to room temperature overnight, then quenched with water, and concentrated to dryness. The crude residue was purified by preparative HPLC to give a TFA salt of the title compound as yellow a solid (1.9 mg). ESI-MS m/z [M+H]$^+$ 373.4.

Example 35

(S)-5-(1-((1-acryloylpiperidin-3-yl)oxy)isoquinolin-3-yl)-2,4-dihydro-3H-1,2,4-triazol-3-one

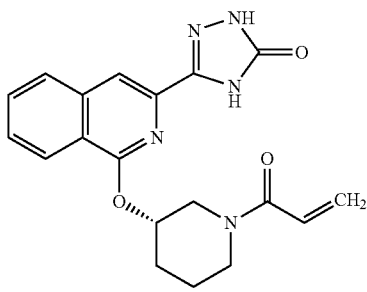 [SMILES: C=CC(=O)N1CCC[C@H](Oc2nc(-c3n[nH]c(=O)[nH]3)cc3ccccc23)C1]

To a solution of (S)-3-(1-(piperidin-3-yloxy)isoquinolin-3-yl)-1H-1,2,4-triazol-5(4H)-one (175 mg, 0.562 mmol) in DCM (3 mL) was added 2,6-dimethylpyridine (0.131 mL, 1.124 mmol) at 0° C. followed by acryloyl chloride (0.091 mL, 1.124 mmol). The reaction mixture was stirred at room temperature overnight. The crude reaction mixture was filtered and purified by preparative HPLC eluting with 20-65% ACN (acid mode) to give a TFA salt of the title compound. A related compound, (S)-1-(3-(5-oxo-4,5-dihydro-1H-1,2,4-triazol-3-yl)isoquinolin-1-yl)piperidin-3-yl acrylate, was also isolated during the chromatographic separation. Peak 1: $^1$H NMR (400 MHz, CD$_3$OD) δ ppm 1.28 (s, 1 H), 1.53-1.67 (m, 1 H), 1.80 (dd, J=9.85, 3.79 Hz, 1 H), 1.93-2.09 (m, 1 H), 2.75 (s, 3 H), 3.03-3.17 (m, 1 H), 3.24 (t, J=10.11 Hz, 1 H), 3.63-3.77 (m, 1 H), 3.86 (d, J=12.88 Hz, 1 H), 4.03 (dt, J=8.46, 4.36 Hz, 1 H), 6.09 (dd, J=10.48, 1.64 Hz, 1 H), 6.70 (dd, J=17.18, 1.77 Hz, 1 H), 7.94 (d, J=8.08 Hz, 1 H), 8.11 (s, 1 H), 8.19 (d, J=8.34 Hz, 1 H), 8.33 (t, J=7.96 Hz, 1 H); peak 2: $^1$H NMR (400 MHz, CD$_3$OD) δ ppm 1.66-1.95 (m, 2 H), 1.95-2.06 (m, 1 H), 2.12 (d, J=4.29 Hz, 1 H), 2.76 (s, 2 H), 3.39-3.51 (m, 1 H), 3.71-3.83 (m, 1 H), 4.02 (d, J=9.09 Hz, 1 H), 5.34 (dt, J=8.15, 4.39 Hz, 1 H), 5.88-5.99 (m, 1 H), 6.22 (dd, J=17.31, 10.48 Hz, 1 H), 6.49 (dd, J=17.43, 1.52 Hz, 1 H), 7.61 (ddd, J=8.27, 6.88, 1.26 Hz, 1 H), 7.66-7.77 (m, 1 H), 7.85-7.97 (m, 1 H), 8.16 (d, J=7.83 Hz, 1 H).

Example 36

(S)-5-(1-((1-acetylpyrrolidin-3-yl)oxy)isoquinolin-3-yl)-2,4-dihydro-3H-1,2,4-triazol-3-one

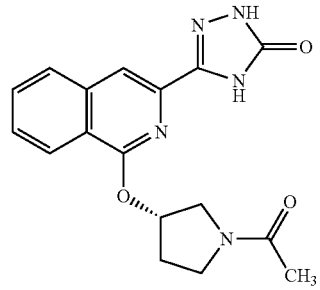 [SMILES: CC(=O)N1CC[C@H](Oc2nc(-c3n[nH]c(=O)[nH]3)cc3ccccc23)C1]

A solution of (S)-5-(1-(pyrrolidin-3-yloxy)isoquinolin-3-yl)-3H-1,2,4-triazol-3-one (200 mg, 0.677 mmol) and 2,6-dimethylpyridine (0.079 mL, 0.677 mmol) in DCM (4 mL) was mixed for 30 minutes. A freshly prepared mixture of acetyl chloride (80 mg, 1.016 mmol), 2,6-dimethylpyridine (0.079 mL, 0.677 mmol) in DCM (1 mL) was added dropwise. The reaction mixture stirred for 20 minutes and then concentrated. The product was purified using preparative HPLC eluting with a gradient of 25-55% ACN in water (acid mode) to give a TFA salt of the title compound (15 mg, 7%). $^1$H NMR (400 MHz, DMSO-d$_6$) δ ppm 1.93-2.06 (m, 3 H), 2.09-2.43 (m, 2 H), 3.38 (br s, 4 H), 3.48-3.86 (m, 4 H), 3.93-4.18 (m, 1 H), 6.04-6.31 (m, 1 H), 7.63-7.74 (m, 1 H), 7.76-7.87 (m, 1 H), 7.94-8.08 (m, 2 H), 8.18 (dd, J=8.21, 0.88 Hz, 1 H), 11.80 (s, 1 H), 12.04 (br s, 1 H); ESI-MS m/z [M+H]$^+$ 340.2.

Example 37

(S)-5-(1-((1-propionylpyrrolidin-3-yl)oxy)isoquinolin-3-yl)-2,4-dihydro-3H-1,2,4-triazol-3-one

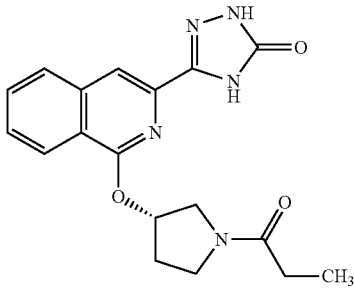 [SMILES: CCC(=O)N1CC[C@H](Oc2nc(-c3n[nH]c(=O)[nH]3)cc3ccccc23)C1]

A solution of (S)-5-(1-(pyrrolidin-3-yloxy)isoquinolin-3-yl)-3H-1,2,4-triazol-3-one (200 mg, 0.677 mmol) and 2,6-dimethylpyridine (0.079 mL, 0.677 mmol) in DCM (4 mL) was mixed for 30 minutes. A freshly prepared mixture of propionyl chloride (94 mg, 1.016 mmol), 2,6-dimethylpyridine (0.079 mL, 0.677 mmol) in DCM (1 mL) was added dropwise. The reaction mixture stirred for 20 minutes and then concentrated. The product was purified using preparative HPLC eluting with a gradient of 25-55% ACN in water (acid mode) to give a TFA salt of the title compound (12 mg, 5%). $^1$H NMR (400 MHz, DMSO-$d_6$) δ ppm 0.95-1.04 (m, 3 H), 2.16-2.40 (m, 4 H), 2.48-2.52 (m, 8 H), 2.64 (s, 1 H), 3.13 (dt, J=3.16, 1.71 Hz, 3 H), 3.50-3.79 (m, 3 H), 4.11 (s, 10 H), 6.08-6.18 (m, 1 H), 7.58-7.66 (m, 1 H), 7.76 (t, J=7.19 Hz, 1 H), 7.94 (d, J=5.13 Hz, 2 H), 8.16 (d, J=8.34 Hz, 1 H); ESI-MS m/z [M+H]$^+$ 354.1.

TABLE 1, below, lists BTK inhibition data for many of the compounds described in the examples, where larger pIC$_{50}$ values represent higher potency. The compounds were tested in accordance with the assay described on page 42 of the specification.

As used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds. It is to be understood that the above description is intended to be illustrative and not restrictive. Many embodiments will be apparent to those of skill in the art upon reading the above description. Therefore, the scope of the invention should be determined with reference to the appended claims and includes the full scope of equivalents to which such claims are entitled. The disclosures of all articles and references, including patents, patent applications and publications, are herein incorporated by reference in their entirety and for all purposes.

TABLE 1

BTK Inhibition (pIC$_{50}$) for Example Compounds

| Example No. | pIC$_{50}$ |
|---|---|
| 1 | 6.7 |
| 2 | 7.1 |
| 3 | 6.5 |
| 4 | >8.1 |
| 5 | >8.7 |
| 6 | 8.0 |
| 7 | 8.0 |
| 8 | >8.6 |
| 9 | >7.9 |
| 10 | 7.5 |
| 11 | 8.5 |
| 12 | 6.9 |
| 13 | >8.0 |
| 14 | 8.2 |
| 15 | 7.6 |
| 16 | >8.5 |
| 17 | >8.6 |
| 18 | >8.2 |
| 19 | >8.2 |
| 20 | >8.6 |
| 21 | 6.9 |
| 22 | >8.9 |
| 23 | >8.9 |
| 24 | >8.9 |
| 25 | >8.6 |
| 26 | >8.6 |
| 27 | >8.9 |

TABLE 1-continued

BTK Inhibition (pIC$_{50}$) for Example Compounds

| Example No. | pIC$_{50}$ |
|---|---|
| 28 | >8.6 |
| 29 | >8.6 |
| 30 | >8.6 |
| 31 | 7.2 |
| 32 | 8.3 |
| 33 | >8.2 |
| 34 | >8.6 |
| 35 | 7.5 |

What is claimed is:

1. A method of treating a disease, disorder or condition in a subject, the method comprising administering to the subject a compound of Formula 1,

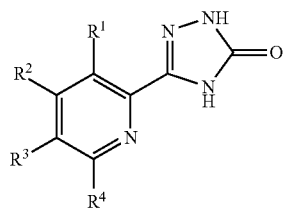

a tautomer thereof or a pharmaceutically acceptable salt of the compound or tautomer, wherein:

$R^1$ is selected from hydrogen, halo, and $C_{1-4}$ alkyl;

$R^2$ and $R^3$ are each indepedently selected from hydrogen, halo, and $C_{1-6}$ alkyl, or $R^2$ and $R^3$, together with carbon atoms to which they are attached, form a benzene ring or a pyridine ring in which the benzene ring is optionally substituted with from one to four substituents independently selected from halo, —CN, —OR$^8$, and $C_{1-6}$ alkyl, and the pyridine ring is optionally substituted with from one to three substituents independently selected from halo, —CN, —OR$^8$, and $C_{1-6}$ alkyl;

$R^4$ has the formula

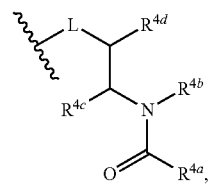

in which

indicates a point of attachment;

L is selected from —O—, —CH$_2$O—, and —N(R$^{4e}$)—;

$R^{4a}$ is selected from —CH$_2$R$^5$ and ethenyl optionally substituted with from one to three substituents independently selected from halo, cyano, and $C_{1-6}$ alkyl optionally substituted with —N(R$^{11}$)R$^{12}$; and (a) $R^{4c}$ is hydrogen, $R^{4e}$ is selected from hydrogen and $C_{1-4}$ alkyl when L is —$N(R^{4e})$—, and $R^{4b}$ and $R^{4d}$, together with a nitrogen atom and carbon atoms to which $R^{4b}$, $R^{4c}$, and $R^{4d}$ are respectively attached, form a pyrrolidine ring or a piperidine ring, each ring optionally substituted with from one to six substituents independently selected from halo, $C_{1-4}$ alkyl, and $C_{1-4}$ haloalkyl; or (b) $R^{4b}$ is selected from hydrogen and $C_{1-4}$ alkyl, $R^{4d}$ is hydrogen, L is —$N(R^{4e})$—, and $R^{4c}$ and $R^{4e}$, together with the carbon atoms and a nitrogen atom to which $R^{4c}$, $R^{4d}$, and $R^{4e}$ are respectively attached, form a pyrrolidine ring or a piperidine ring, each ring optionally substituted with from one to six substituents independently selected from halo, $C_{1-4}$ alkyl, and $C_{1-4}$ haloalkyl; or (c) $R^{4d}$ is hydrogen, $R^{4e}$ is selected from hydrogen and $C_{1-4}$ alkyl when L is —$N(R^{4e})$—, and $R^{4b}$ and $R^{4c}$, together with the nitrogen and carbon atoms to which $R^{4b}$ and $R^{4c}$ are respectively attached, form pyrrolidine ring or a piperidine ring, each ring optionally substituted with from one to six substituents independently selected from halo, $C_{1-4}$ alkyl, and $C_{1-4}$ haloalkyl;

$R^5$ is selected from hydrogen, halo, and $C_{1-4}$ alkyl;
each $R^8$ is independently selected from
hydrogen and
$C_{1-6}$ alkyl; and
each $R^{11}$ and $R^{12}$ is indepedently selected from
hydrogen and
$C_{1-6}$ alkyl;
wherein the disease, dirorder or condition is selected from B-cell lymphoma, chronic lymphocytic leukemia, and multiple myeloma.

2. The method according to claim 1, wherein $R^1$ is hydrogen.

3. The method according to claim 1, wherein $R^2$ and $R^3$ are each independently selected from hydrogen, fluoro, chloro, and methyl.

4. The method according to claim 1, wherein $R^2$ and $R^3$, together with the carbon atoms to which they are attached, form a benzene ring or a pyridine ring in which the benzene ring is optionally substituted with from one to four substituents independently selected from halo, —CN, —$OR^8$, and $C_{1-6}$ alkyl, and the pyridine ring is optionally substituted with from one to three substituents independently selected from halo, —CN, —$OR^8$, and $C_{1-6}$ alkyl.

5. The method according to claim 4, wherein the benzene ring or the pyridine ring is optionally substituted with one or two substituents independently selected from fluoro, chloro, and methyl.

6. The method according to claim 5, wherein $R^2$ and $R^3$, together with the carbon atoms to which they are attached, form a benzene ring which is optionally substituted with one or two substituents independently selected fluoro, chloro, and methyl.

7. The method according to claim 1, wherein $R^{4a}$ is ethenyl optionally substituted with from one to three methyl groups.

8. The method according to claim 7, wherein $R^{4a}$ is unsubstituted ethenyl.

9. The method according to claim 1, wherein $R^{4a}$ is —$CH_2R^5$ and $R^5$ is halo.

10. The method according to claim 1, wherein $R^{4c}$ is hydrogen, $R^{4e}$ is selected from hydrogen and $C_{1-4}$ alkyl when L is —$N(R^{4e})$—, and $R^{4b}$ and $R^{4d}$, together with the nitrogen atom and the carbon atoms to which $R^{4b}$, $R^{4c}$, and $R^{4d}$ are respectively attached, form a pyrrolidine ring or a piperidine ring, each ring optionally substituted with from one to six substituents independently selected from halo, $C_{1-4}$ alkyl, and $C_{1-4}$ haloalkyl.

11. The method according to claim 10, wherein $R^{4b}$ and $R^{4d}$, together with the nitrogen atom and the carbon atoms to which $R^{4b}$, $R^{4c}$, and $R^{4d}$ are respectively attached, form a pyrrolidine ring which is optionally substituted with from one to four substituents independently selected from halo, $C_{1-4}$ alkyl, and $C_{1-4}$ haloalkyl.

12. The method according to claim 10, wherein the ring formed by $R^{4b}$ and $R^{4d}$, together with the nitrogen atom and the carbon atoms to which $R^{4b}$, $R^{4c}$, and $R^{4d}$ are respectively attached, is unsubstituted.

13. The method according to claim 1, wherein $R^{4b}$ is selected from hydrogen and $C_{1-4}$ alkyl, $R^{4d}$ is hydrogen, L is —$N(R^{4e})$—, and $R^{4c}$ and $R^{4e}$, together with the carbon atoms and the nitrogen atom to which $R^{4c}$, $R^{4d}$, and $R^{4e}$ are respectively attached, form a pyrrolidine ring or a piperidine ring, each ring optionally substituted with from one to six substituents independently selected from halo, $C_{1-4}$ alkyl, and $C_{1-4}$ haloalkyl.

14. The method according to claim 13, wherein $R^{4c}$ and $R^{4e}$, together with the carbon atoms and the nitrogen atom to which $R^{4c}$, $R^{4d}$, and $R^{4e}$ are respectively attached, form a pyrrolidine ring which is optionally substituted with from one to six substituents independently selected from halo, $C_{1-4}$ alkyl, and $C_{1-4}$ haloalkyl.

15. The method according to claim 13, wherein the ring formed by $R^{4c}$ and $R^{4e}$, together with the carbon atoms and the nitrogen atom to which $R^{4c}$, $R^{4d}$, and $R^{4e}$ are respectively attached, is unsubstituted.

16. The method according to claim 1, wherein $R^{4d}$ is hydrogen, $R^{4e}$ is selected from hydrogen and $C_{1-4}$ alkyl when L is —$N(R^{4e})$—, and $R^{4b}$ and $R^{4c}$, together with the nitrogen and carbon atoms to which $R^{4b}$ and $R^{4c}$ are respectively attached, form a pyrrolidine ring or a piperidine ring, each ring optionally substituted with from one to six substituents independently selected from halo, $C_{1-4}$ alkyl, and $C_{1-4}$ haloalkyl.

17. The method according to claim 16, wherein $R^{4b}$ and $R^{4c}$, together with the nitrogen and carbon atoms to which $R^{4b}$ and $R^{4c}$ are respectively attached, form a pyrrolidine ring which is optionally substituted with from one to six substituents independently selected from halo, $C_{1-4}$ alkyl, and $C_{1-4}$ haloalkyl.

18. The method according to claim 16, wherein the ring formed by $R^{4b}$ and $R^{4c}$, together with the nitrogen and carbon atoms to which $R^{4b}$ and $R^{4c}$ are respectively attached, is unsubstituted.

19. The method according to claim 1, wherein L is —$N(R^{4e})$—.

20. The method according to claim 1, wherein L is selected from —O— and —$CH_2O$—.

21. The method according to claim 20, wherein L is —O—.

22. The method according to claim 1, wherein the compound is selected from the following compounds:
(R)-3-(1-((1-methacryloylpyrrolidin-3-yl)oxy)isoquinolin-3-yl)-1H-1,2,4-triazol-5(4H)-one;
(R)-3-(1((1-acryloylpyrrolidin-3-yl)oxy)isoquinolin-3-yl)-1H-1,2,4-triazol-5(4H)-one;
(R,E)-3-(1-((1-(but-2-enoyl)pyrrolidin-3-yl)oxy)isoquinolin-3-yl)-1H-1,2,4-triazol-5(4H)-one;
N-(1-(3-(5-oxo-4,5-dihydro-1H-1,2,4-triazol-3-yl)isoquinolin-1-yl)pyrrolidin-3-yl)acrylamide;

(S)-3-(1-((1-acryloylpyrrolidin-3-yl)oxy)isoquinolin-3-yl)-1H-1,2,4-triazol-5(4H)-one;
(S)-3-(1-(((1-acryloylpyrrolidin-2-yl)methyl)amino)isoquinolin-3-yl)-1H-1,2,4-triazol-5(4H)-one;
(S)-3-(1-((1-acryloylpyrrolidin-2-yl)methoxy)isoquinolin-3-yl)-1H-1,2,4-triazol-5(4H)-one;
(S)-3-(1-((1-acryloylpyrrolidin-3-yl)amino)isoquinolin-3-yl)-1H-1,2,4-triazol-5(4H)-one;
(R)-3-(1((1-acryloylpyrrolidin-2-yl)methoxy)isoquinolin-3-yl)-1H-1,2,4-triazol-5(4H)-one;
(S)-3-(1-((1-methacryloylpyrrolidin-3-yl)amino)isoquinolin-3-yl)-1H-1,2,4-triazol-5(4H)-one;
(S)-3-(1-((1-acryloylpyrrolidin-3-yl)(methyl)amino)isoquinolin-3-yl)-1H-1,2,4-triazol-5(4H)-one;
(S)-3-(1-((1-methacryloylpyrrolidin-3-yl)oxy)isoquinolin-3-yl)-1H-1,2,4-triazol-5(4H)-one;
(S)-3-(1-(((1-acryloylpyrrolidin-3-yl)oxy)methyl)isoquinolin-3-yl)-1H-1,2,4-triazol-5(4H)-one;
(S,E)-5-(1-((1-(4-(dimethylamino)but-2-enoyl)pyrrolidin-3-yl)oxy)isoquinolin-3-yl)-2,4-dihydro-3H-1,2,4-triazol-3-one;
(S,E)-3-(1-((1-(but-2-enoyl)pyrrolidin-3-yl)amino)isoquinolin-3-yl)-1H-1,2,4-triazol-5(4H)-one;
(S)-3-(8-((1-acryloylpyrrolidin-3-yl)oxy)-1,7-naphthyridin-6-yl)-1H-1,2,4-triazol-5(4H)-one;
(S)-3-(8-((1-acryloylpyrrolidin-3-yl)amino)-1,7-naphthyridin-6-yl)-1H-1,2,4-triazol-5(4H)-one;
(S)-3-(1-((1-acryloylpyrrolidin-3-yl)oxy)-7-fluoroisoquinolin-3-yl)-1H-1,2,4-triazol-5(4H)-one;
3-(1-((trans-1-acryloyl-4-methylpyrrolidin-3-yl)oxy)isoquinolin-3-yl)-1H-1,2,4-triazol-5(4H)-one;
3-(1-(((3R,4S)-1-acryloyl-4-methylpyrrolidin-3-yl)oxy)isoquinolin-3-yl)-1H-1,2,4-triazol-5(4H)-one;
3-(1-(((3S,4R)-1-acryloyl-4-methylpyrrolidin-3-yl)oxy)isoquinolin-3-yl)-1H-1,2,4-triazol-5(4H)-one;
(S)-3-(1-((1-acryloylpyrrolidin-3-yl)oxy)-8-fluoroisoquinolin-3-yl)-1H-1,2,4-triazol-5(4H)-one;
(S)-3-(1-((1-acryloylpyrrolidin-3-yl)amino)-8-fluoroisoquinolin-3-yl)-1H-1,2,4-triazol-5(4H)-one;
(S)-3-(1-((1-acryloylpyrrolidin-3-yl)oxy)-7-chloroisoquinolin-3-yl)-1H-1,2,4-triazol-5(4H)-one;
(S)-3-(1-((1-acryloylpyrrolidin-3-yl)amino)-7-fluoroisoquinolin-3-yl)-1H-1,2,4-triazol-5(4H)-one;
(S)-3-(1-((1-acryloylpyrrolidin-3-yl)amino)-7-chloroisoquinolin-3-yl)-1H-1,2,4-triazol-5(4H)-one;
(S)-3-(1-((1-acryloylpyrrolidin-3-yl)oxy)-8-chloroisoquinolin-3-yl)-1H-1,2,4-triazol-5(4H)-one;
(S)-3-(1-((1-acryloylpyrrolidin-3-yl)amino)-8-chloroisoquinolin-3-yl)-1H-1,2,4-triazol-5(4H)-one;
(S)-3-(1-((1-acryloylpyrrolidin-3-yl)amino)-8-methoxyisoquinolin-3-yl)-1H-1,2,4-triazol-5(4H)-one;
(S)-3-(6-((1-acryloylpyrrolidin-3-yl)oxy)-4-methylpyridin-2-yl)-1H-1,2,4-triazol-5(4H)-one;
(S)-3-(6-((1-acryloylpyrrolidin-3-yl)oxy)pyridin-2-yl)-1H-1,2,4-triazol-5(4H)-one;
(S)-3-(6-((1-acryloylpyrrolidin-3-yl)oxy)-5-methylpyridin-2-yl)-1H-1,2,4-triazol-5(4H)-one;
(S)-5-(1-((1-(2-chloroacetyl)pyrrolidin-3-yl)oxy)isoquinolin-3-yl)-2,4-dihydro-3H-1,2,4-triazol-3-one;
(S)-5-(1-((1-(2-chloroacetyl)pyrrolidin-3-yl)amino)isoquinolin-3-yl)-2,4-dihydro-3H-1,2,4-triazol-3-one;
(S)-5-(1-((1-acryloylpiperidin-3-yl)oxy)isoquinolin-3-yl)-2,4-dihydro-3H-1,2,4-triazol-3-one;
(S)-5-(1-((1-acetylpyrrolidin-3-yl)oxy)isoquinolin-3-yl)-2,4-dihydro-3H-1,2,4-triazol-3-one;
(S)-5-(1-((1-propionylpyrrolidin-3-yl)oxy)isoquinolin-3-yl)-2,4-dihydro-3H-1,2,4-triazol-3-one;
a tautomer of any one of the aforementioned compounds;
a stereoisomer of any one of the aforementioned compounds or tautomers; and
a pharmaceutically acceptable salt of any one of the aforementioned compounds, tautomers or stereoisomers.

23. The method according to claim 1, further comprising administering to the subject at least one additional pharmacologically active agent.

24. The method according to claim 1, wherein the compound is (S)-3-(1-((1-acryloylpyrrolidin-3-yl)oxy)isoquinolin-3-yl)-1H-1,2,4-triazol-5(4H)-one, a tautomer thereof, or a pharmaceutically acceptable salt of the compound or tautomer.

25. The method according to claim 1, wherein the compound is (S)-3-(1-((1-acryloylpyrrolidin-3-yl)amino)isoquinolin-3-yl)-1H-1,2,4-triazol-5(4H)-one, a tautomer thereof, or a pharmaceutically acceptable salt of the compound or tautomer.

26. The method according to claim 1, wherein the compound is (S)-3-(8-((1-acryloylpyrrolidin-3-yl)oxy)-1,7-naphthyridin-6-yl)-1H-1,2,4-triazol-5(4H)-one, a tautomer thereof, or a pharmaceutically acceptable salt of the compound or tautomer.

27. The method according to claim 1, wherein the compound is (S)-3-(8-((1-acryloylpyrrolidin-3-yl)amino)-1,7-naphthyridin-6-yl)-1H-1,2,4-triazol-5(4H)-one, a tautomer thereof, or a pharmaceutically acceptable salt of the compound or tautomer.

28. The method according to claim 1, wherein the compound is (S)-3-(1-((1-acryloylpyrrolidin-3-yl)oxy)-8-fluoroisoquinolin-3-yl)-1H-1,2,4-triazol-5(4H)-one, a tautomer thereof, or a pharmaceutically acceptable salt of the compound or tautomer.

29. The method according to claim 1, wherein the compound is (S)-3-(1-((1-acryloylpyrrolidin-3-yl)amino)-8-fluoroisoquinolin-3-yl)-1H-1,2,4-triazol-5(4H)-one, a tautomer thereof, or a pharmaceutically acceptable salt of the compound or tautomer.

30. The method according to claim 1, wherein the compound is (S)-3-(1-((1-acryloylpyrrolidin-3-yl)oxy)-7-chloroisoquinolin-3-yl)-1H-1,2,4-triazol-5(4H)-one, a tautomer thereof, or a pharmaceutically acceptable salt of the compound or tautomer.

31. The method according to claim 1, wherein the compound is (S)-3-(1-((1-acryloylpyrrolidin-3-yl)amino)-7-chloroisoquinolin-3-yl)-1H-1,2,4-triazol-5(4H)-one, a tautomer thereof, or a pharmaceutically acceptable salt of the compound or tautomer.

32. The method according to claim 1, wherein the compound is (S)-3-(1-((1-acryloylpyrrolidin-3-yl)oxy)-8-chloroisoquinolin-3-yl)-1H-1,2,4-triazol-5(4H)-one, a tautomer thereof, or a pharmaceutically acceptable salt of the compound or tautomer.

33. The method according to claim 1, wherein the compound is (S)-3-(1-((1-acryloylpyrrolidin-3-yl)amino)-8-chloroisoquinolin-3-yl)-1H-1,2,4-triazol-5(4H)-one, a tautomer thereof, or a pharmaceutically acceptable salt of the compound or tautomer.

\* \* \* \* \*